US009932626B2

(12) United States Patent
Duffy et al.

(10) Patent No.: US 9,932,626 B2
(45) Date of Patent: Apr. 3, 2018

(54) DETECTION OF DNA OR RNA USING SINGLE MOLECULE ARRAYS AND OTHER TECHNIQUES

(71) Applicant: Quanterix Corporation, Lexington, MA (US)

(72) Inventors: David C. Duffy, Arlington, MA (US); Linan Song, Waltham, MA (US); Dandan Shan, Acton, MA (US); Mingwei Zhao, Wellesley, MA (US)

(73) Assignee: Quanterix Corporation, Lexington, MA (US)

( * ) Notice: Subject to any disclaimer, the term of this patent is extended or adjusted under 35 U.S.C. 154(b) by 0 days.

(21) Appl. No.: 14/761,271

(22) PCT Filed: Jan. 15, 2014

(86) PCT No.: PCT/US2014/011730
§ 371 (c)(1),
(2) Date: Jul. 15, 2015

(87) PCT Pub. No.: WO2014/113502
PCT Pub. Date: Jul. 24, 2014

(65) Prior Publication Data
US 2015/0353997 A1    Dec. 10, 2015

Related U.S. Application Data

(60) Provisional application No. 61/752,545, filed on Jan. 15, 2013.

(51) Int. Cl.
*C12Q 1/68*    (2006.01)
(52) U.S. Cl.
CPC .................. *C12Q 1/6837* (2013.01)

(58) Field of Classification Search
CPC .......... C12Q 1/68; C07H 21/02; C40B 30/04; G01N 21/06; Y10S 977/933
See application file for complete search history.

(56) References Cited

U.S. PATENT DOCUMENTS

| 3,712,986 A | 1/1973 | Collings |
| 4,200,110 A | 4/1980 | Peterson et al. |
(Continued)

FOREIGN PATENT DOCUMENTS

| AU | 199956253 B2 | 3/2000 |
| CN | 1635146 A | 7/2005 |
(Continued)

OTHER PUBLICATIONS

Song et al, Direct Detection of Bacterial Genomic DNA at Sub-Femtomolar Concentrations Using Single Molecule Arrays, 2013, Anal. Chem., 85, 1932-1939 (post art) (Year: 2013).*

(Continued)

*Primary Examiner* — Narayan Bhat
(74) *Attorney, Agent, or Firm* — Wolf, Greenfield & Sacks, P.C.

(57) ABSTRACT

Described herein are methods and systems for detecting DNA or RNA using single molecules array or other techniques. DNA or RNA from the sample may be fragmented and exposed to a first type of binding ligand and a second type of binding ligand that comprise nucleic acid sequences complimentary at least a portion of a sequence contained in the target DNA or RNA. At least a portion of the fragmented DNA or RNA associates with at least one of the first type of binding ligand and/or the second type of binding ligand, wherein the first type of binding ligand and second type of binding ligand comprises nucleic acid sequences complimentary to a different portions of a sequence contained in the DNA or RNA. A portion of the sample exposed to the
(Continued)

binding ligands is analyzed to determine the number of fragmented DNA or RNA sequences.

25 Claims, 24 Drawing Sheets

(56) References Cited

U.S. PATENT DOCUMENTS

| | | |
|---|---|---|
| 4,232,119 A | 11/1980 | Carlsson et al. |
| 4,631,211 A | 12/1986 | Houghten |
| 4,780,421 A | 10/1988 | Kameda et al. |
| 4,883,642 A | 11/1989 | Bisconte |
| 4,907,037 A | 3/1990 | Boisde et al. |
| 4,924,870 A | 5/1990 | Wlodarczyk et al. |
| 4,962,037 A | 10/1990 | Jett et al. |
| 5,026,159 A | 6/1991 | Allen et al. |
| 5,028,535 A | 7/1991 | Buechler et al. |
| 5,089,391 A | 2/1992 | Buechler et al. |
| 5,091,300 A | 2/1992 | Hurni et al. |
| 5,108,961 A | 4/1992 | Zhong et al. |
| 5,152,816 A | 10/1992 | Berkey |
| 5,190,857 A | 3/1993 | Allen et al. |
| 5,196,306 A | 3/1993 | Bobrow et al. |
| 5,244,636 A | 9/1993 | Walt et al. |
| 5,244,813 A | 9/1993 | Walt et al. |
| 5,250,264 A | 10/1993 | Walt et al. |
| 5,252,494 A | 10/1993 | Walt |
| 5,298,741 A | 3/1994 | Walt et al. |
| 5,315,375 A | 5/1994 | Allen |
| 5,320,814 A | 6/1994 | Walt et al. |
| 5,329,461 A | 7/1994 | Allen et al. |
| 5,374,395 A | 12/1994 | Robinson et al. |
| 5,405,783 A | 4/1995 | Pirrung et al. |
| 5,439,794 A | 8/1995 | Barton |
| 5,445,934 A | 8/1995 | Fodor et al. |
| 5,468,846 A | 11/1995 | Ichikawa et al. |
| 5,488,567 A | 1/1996 | Allen et al. |
| 5,512,490 A | 4/1996 | Walt et al. |
| 5,532,138 A | 7/1996 | Singh et al. |
| 5,532,379 A | 7/1996 | Fujimoto |
| 5,545,531 A | 8/1996 | Rava et al. |
| 5,583,001 A | 12/1996 | Bobrow et al. |
| 5,620,850 A | 4/1997 | Bamdad et al. |
| 5,633,972 A | 5/1997 | Walt et al. |
| 5,690,894 A | 11/1997 | Pinkel et al. |
| 5,700,637 A | 12/1997 | Southern |
| 5,731,158 A | 3/1998 | Bobrow et al. |
| 5,770,455 A | 6/1998 | Cargill et al. |
| 5,807,522 A | 9/1998 | Brown et al. |
| 5,814,524 A | 9/1998 | Walt et al. |
| 5,885,529 A | 3/1999 | Babson et al. |
| 5,900,481 A | 5/1999 | Lough et al. |
| 5,981,180 A | 11/1999 | Chandler et al. |
| 6,001,564 A | 12/1999 | Bergeron et al. |
| 6,007,690 A | 12/1999 | Nelson et al. |
| 6,013,445 A | 1/2000 | Albrecht et al. |
| 6,023,540 A | 2/2000 | Walt et al. |
| 6,133,436 A | 10/2000 | Koster et al. |
| 6,143,496 A | 11/2000 | Brown et al. |
| 6,156,270 A | 12/2000 | Buechler |
| 6,174,695 B1 | 1/2001 | Hammock et al. |
| 6,210,910 B1 | 4/2001 | Walt et al. |
| 6,266,459 B1 | 7/2001 | Walt et al. |
| 6,285,807 B1 | 9/2001 | Walt et al. |
| 6,327,410 B1 | 12/2001 | Walt et al. |
| 6,329,139 B1 | 12/2001 | Nova et al. |
| 6,368,874 B1 | 4/2002 | Gallop et al. |
| 6,377,721 B1 | 4/2002 | Walt et al. |
| 6,388,746 B1 | 5/2002 | Eriksson et al. |
| 6,396,995 B1 | 5/2002 | Stuelpnagel et al. |
| 6,406,845 B1 | 6/2002 | Walt et al. |
| 6,432,630 B1 | 8/2002 | Blankenstein |
| 6,482,593 B2 | 11/2002 | Walt et al. |
| 6,582,908 B2 | 6/2003 | Fodor et al. |
| 6,602,702 B1 | 8/2003 | McDevitt et al. |
| 6,620,584 B1 | 9/2003 | Chee et al. |
| 6,635,452 B1 | 10/2003 | Monforte et al. |
| 6,667,159 B1 | 12/2003 | Walt et al. |
| 6,713,309 B1 | 3/2004 | Anderson et al. |
| 6,714,303 B2 | 3/2004 | Ivarsson |
| 6,821,449 B2 | 11/2004 | Caplen et al. |
| 6,838,051 B2 | 1/2005 | Marquiss et al. |
| 6,858,394 B1 | 2/2005 | Chee et al. |
| 6,859,570 B2 | 2/2005 | Walt et al. |
| 6,878,345 B1 | 4/2005 | Astle |
| 6,929,924 B2 | 8/2005 | Bouanani et al. |
| 6,942,968 B1 | 9/2005 | Dickinson et al. |
| 6,943,034 B1 | 9/2005 | Winkler et al. |
| 6,991,939 B2 | 1/2006 | Walt et al. |
| 6,999,657 B2 | 2/2006 | Walt |
| 7,056,746 B2 | 6/2006 | Seul et al. |
| 7,060,431 B2 | 6/2006 | Chee et al. |
| 7,115,884 B1 | 10/2006 | Walt et al. |
| 7,211,390 B2 | 5/2007 | Rothberg et al. |
| 7,244,559 B2 | 7/2007 | Rothberg et al. |
| 7,250,267 B2 | 7/2007 | Walt et al. |
| 7,264,929 B2 | 9/2007 | Rothberg et al. |
| 7,348,181 B2 | 3/2008 | Walt et al. |
| 7,480,433 B2 | 1/2009 | Walt et al. |
| 7,572,581 B2 | 8/2009 | Gelfand et al. |
| 7,575,866 B2 | 8/2009 | Cornish et al. |
| 7,651,841 B2 | 1/2010 | Song et al. |
| 7,741,046 B2 | 6/2010 | Larsen et al. |
| 7,759,062 B2 | 7/2010 | Allawi et al. |
| 7,776,553 B2 | 8/2010 | Love et al. |
| 7,838,250 B1 | 11/2010 | Goix et al. |
| 8,222,047 B2 | 7/2012 | Duffy et al. |
| 8,236,574 B2 | 8/2012 | Duffy et al. |
| 8,415,171 B2 | 4/2013 | Rissin et al. |
| 8,460,878 B2 | 6/2013 | Walt et al. |
| 8,460,879 B2 | 6/2013 | Walt et al. |
| 8,492,098 B2 | 7/2013 | Walt et al. |
| 8,846,415 B2 | 9/2014 | Duffy et al. |
| 9,110,025 B2 | 8/2015 | Rissin et al. |
| 9,310,360 B2 | 4/2016 | Duffy et al. |
| 9,395,359 B2 | 7/2016 | Walt et al. |
| 9,482,662 B2 | 11/2016 | Duffy et al. |
| 9,551,663 B2 | 1/2017 | Rissin et al. |
| 9,678,068 B2 | 6/2017 | Duffy et al. |
| 2002/0009391 A1 | 1/2002 | Marquiss et al. |
| 2002/0090650 A1 | 7/2002 | Empedocles et al. |
| 2002/0122612 A1 | 9/2002 | Walt et al. |
| 2003/0027126 A1 | 2/2003 | Walt et al. |
| 2003/0091475 A1 | 5/2003 | Yu et al. |
| 2003/0096243 A1 | 5/2003 | Busa |
| 2003/0104361 A1 | 6/2003 | Weininger et al. |
| 2003/0129611 A1* | 7/2003 | Bao ............ C12Q 1/6818 435/6.11 |
| 2003/0143580 A1 | 7/2003 | Straus et al. |
| 2003/0198573 A1 | 10/2003 | Forood et al. |
| 2004/0038426 A1 | 2/2004 | Manalis |
| 2004/0043502 A1 | 3/2004 | Song et al. |
| 2004/0053322 A1 | 3/2004 | McDevitt et al. |
| 2004/0071599 A1 | 4/2004 | Rusch et al. |
| 2004/0072278 A1 | 4/2004 | Chou et al. |
| 2004/0086426 A1 | 5/2004 | Vann et al. |
| 2004/0101918 A1 | 5/2004 | Cauci |
| 2004/0142386 A1 | 7/2004 | Rigler et al. |
| 2004/0229253 A1* | 11/2004 | Hyldig-Nielsen ... C12Q 1/6818 435/6.12 |
| 2004/0248325 A1 | 12/2004 | Bukusoglu |
| 2004/0253624 A1 | 12/2004 | Smith et al. |
| 2004/0259237 A1 | 12/2004 | Kellogg et al. |
| 2005/0112634 A1 | 5/2005 | Woudenberg et al. |
| 2005/0112655 A1 | 5/2005 | Banerjee et al. |
| 2005/0129581 A1 | 6/2005 | McBride et al. |
| 2005/0130173 A1 | 6/2005 | Leamon et al. |
| 2005/0130188 A1 | 6/2005 | Walt et al. |
| 2005/0131650 A1 | 6/2005 | Andersson et al. |
| 2005/0164289 A1 | 7/2005 | Quate et al. |
| 2005/0221281 A1 | 10/2005 | Ho |
| 2005/0226780 A1 | 10/2005 | Sandell et al. |
| 2005/0244308 A1 | 11/2005 | Tanaami et al. |
| 2005/0266433 A1 | 12/2005 | Kapur et al. |

(56) References Cited

U.S. PATENT DOCUMENTS

| | | |
|---|---|---|
| 2006/0006067 A1 | 1/2006 | Unger |
| 2006/0013543 A1 | 1/2006 | Walt et al. |
| 2006/0040297 A1 | 2/2006 | Leamon et al. |
| 2006/0068409 A1 | 3/2006 | Phan et al. |
| 2006/0078998 A1 | 4/2006 | Puskas et al. |
| 2006/0084183 A1 | 4/2006 | Henricksen |
| 2006/0139635 A1 | 6/2006 | Kersey et al. |
| 2007/0040095 A1 | 2/2007 | Walt et al. |
| 2007/0059754 A1 | 3/2007 | Kordunsky et al. |
| 2007/0074972 A1 | 4/2007 | Nassef et al. |
| 2007/0116607 A1 | 5/2007 | Wang et al. |
| 2007/0259381 A1 | 11/2007 | Rissin et al. |
| 2007/0259385 A1 | 11/2007 | Rissin et al. |
| 2007/0259448 A1 | 11/2007 | Rissin et al. |
| 2008/0032324 A1 | 2/2008 | Walt et al. |
| 2008/0064113 A1 | 3/2008 | Goix et al. |
| 2008/0269069 A1 | 10/2008 | Bacher et al. |
| 2009/0036324 A1 | 2/2009 | Fan et al. |
| 2009/0087860 A1 | 4/2009 | Todd et al. |
| 2009/0142755 A1 | 6/2009 | Albitar |
| 2009/0149341 A1 | 6/2009 | Walt et al. |
| 2009/0156425 A1 | 6/2009 | Walt et al. |
| 2009/0170728 A1 | 7/2009 | Walt et al. |
| 2009/0239308 A1 | 9/2009 | Dube et al. |
| 2009/0254180 A1 | 10/2009 | Pazanowski et al. |
| 2009/0289834 A1 | 11/2009 | Devensky |
| 2009/0307772 A1 | 12/2009 | Markham et al. |
| 2010/0075355 A1 | 3/2010 | Duffy et al. |
| 2010/0075407 A1 | 3/2010 | Duffy et al. |
| 2010/0075439 A1 | 3/2010 | Duffy et al. |
| 2010/0075862 A1 | 3/2010 | Duffy et al. |
| 2010/0140289 A1 | 6/2010 | Knobel et al. |
| 2010/0189338 A1 | 7/2010 | Lin et al. |
| 2010/0192573 A1 | 8/2010 | Hamilton et al. |
| 2010/0204335 A1 | 8/2010 | Beddingfield et al. |
| 2010/0225913 A1 | 9/2010 | Trainer |
| 2010/0227379 A1 | 9/2010 | Wo et al. |
| 2010/0329929 A1 | 12/2010 | Goix et al. |
| 2011/0037463 A1 | 2/2011 | Bertacco et al. |
| 2011/0105348 A1* | 5/2011 | Hinnah ............... C12Q 1/6818 506/9 |
| 2011/0183330 A1 | 7/2011 | Lo et al. |
| 2011/0195852 A1 | 8/2011 | Walt et al. |
| 2011/0212462 A1 | 9/2011 | Duffy et al. |
| 2011/0212537 A1 | 9/2011 | Rissin et al. |
| 2011/0212848 A1 | 9/2011 | Duffy et al. |
| 2011/0229888 A1* | 9/2011 | Hengen ............... C12Q 1/6816 435/6.11 |
| 2011/0245097 A1 | 10/2011 | Rissin et al. |
| 2012/0183967 A1 | 7/2012 | Dressman et al. |
| 2012/0196774 A1 | 8/2012 | Fournier et al. |
| 2012/0214160 A1 | 8/2012 | Deng et al. |
| 2012/0277114 A1 | 11/2012 | Duffy et al. |
| 2012/0289428 A1 | 11/2012 | Duffy et al. |
| 2013/0165342 A1 | 6/2013 | Rissin et al. |
| 2013/0345078 A1 | 12/2013 | Walt et al. |
| 2014/0094386 A1 | 4/2014 | Wilson et al. |
| 2014/0227720 A1 | 8/2014 | Wilson et al. |
| 2014/0302532 A1 | 10/2014 | Wilson et al. |
| 2015/0233905 A1 | 8/2015 | Walt et al. |
| 2015/0355182 A1 | 12/2015 | Rissin et al. |
| 2016/0123669 A1 | 5/2016 | Rissin et al. |
| 2016/0258959 A1 | 9/2016 | Wilson et al. |
| 2017/0038390 A1 | 2/2017 | Walt et al. |
| 2017/0160292 A1 | 6/2017 | Wilson et al. |

FOREIGN PATENT DOCUMENTS

| | | |
|---|---|---|
| CN | 1950520 A | 4/2007 |
| CN | 101351564 A | 1/2009 |
| CN | 101529227 A | 9/2009 |
| CN | 101541974 A | 9/2009 |
| DE | 19540098 A1 | 4/1997 |
| EP | 0 805 215 A2 | 11/1997 |
| EP | 1 180 679 A1 | 2/2002 |
| EP | 1 259 810 B1 | 11/2006 |
| EP | 1 721 657 A1 | 11/2006 |
| EP | 2 267 451 A2 | 12/2010 |
| EP | 2 201 374 B1 | 10/2015 |
| JP | 2001-269196 A | 10/2001 |
| JP | 2002-506200 A | 2/2002 |
| JP | 2002-525587 A | 8/2002 |
| JP | 2002-526743 A | 8/2002 |
| JP | 2004-354164 A | 12/2004 |
| JP | 2005-518553 A | 6/2005 |
| JP | 2006-511792 A | 4/2006 |
| WO | WO 88/05533 A1 | 7/1988 |
| WO | WO 93/06121 A1 | 4/1993 |
| WO | WO 93/24517 A2 | 12/1993 |
| WO | WO 95/25116 A1 | 9/1995 |
| WO | WO 95/32425 A1 | 11/1995 |
| WO | WO 95/35506 A2 | 12/1995 |
| WO | WO 97/27326 A1 | 7/1997 |
| WO | WO 98/50782 A2 | 11/1998 |
| WO | WO 99/45357 A2 | 9/1999 |
| WO | WO 99/58948 A2 | 11/1999 |
| WO | WO 00/04372 A1 | 1/2000 |
| WO | WO 00/47996 A2 | 8/2000 |
| WO | WO 01/57520 A2 | 8/2001 |
| WO | WO 03/054142 A2 | 7/2003 |
| WO | WO 03/073817 A1 | 9/2003 |
| WO | WO 2004/065000 A1 | 8/2004 |
| WO | WO 2004/083443 A1 | 9/2004 |
| WO | WO 2005/019419 A2 | 3/2005 |
| WO | WO 2005/023414 A1 | 3/2005 |
| WO | WO 2005/033283 A2 | 4/2005 |
| WO | WO 2005/054431 A2 | 6/2005 |
| WO | WO 2006/007726 A1 | 1/2006 |
| WO | WO 2006/055739 A2 | 5/2006 |
| WO | WO 2006/078289 A2 | 7/2006 |
| WO | WO 2006/102297 A1 | 9/2006 |
| WO | WO 2006/108180 A2 | 10/2006 |
| WO | WO 2007/044091 A2 | 4/2007 |
| WO | WO 2007/044974 A2 | 4/2007 |
| WO | WO 2007/081385 A2 | 7/2007 |
| WO | WO 2007/081386 A2 | 7/2007 |
| WO | WO 2007/081387 A1 | 7/2007 |
| WO | WO 2007/084192 A2 | 7/2007 |
| WO | WO 2007/098148 A2 | 8/2007 |
| WO | WO 2007/114947 A2 | 10/2007 |
| WO | WO 2008/048371 A2 | 4/2008 |
| WO | WO 2009/029073 A1 | 3/2009 |
| WO | WO 2010/039180 A2 | 4/2010 |
| WO | WO 2001/109364 * | 9/2011 |
| WO | WO 2011/109364 A2 | 9/2011 |
| WO | WO 2011/109372 A1 | 9/2011 |
| WO | WO 2014/183096 A1 | 11/2014 |
| WO | WO 2016/115256 A1 | 7/2016 |
| WO | WO 2016/130923 A1 | 8/2016 |

OTHER PUBLICATIONS

International Search Report and Written Opinion dated May 13, 2014 for PCT/US14/11730.

International Preliminary Report on Patentability (Chapter II) dated Feb. 4, 2015 for PCT/US14/11730.

[No Author Listed], bioMérieux and Quanterix Sign Strategic Partnership in Ultrasensitive and Multiplex Immunoassays. Quanterix Press Release. Nov. 15, 2012. 2 pages.

[No Author Listed], Does Brain Hypoxia Help Kick Off Alzheimer's Pathology? Alzheimer Research Forum. Dec. 16, 2011. http://www.alzforum.org/new/detailprint.asp?id=3002 [last accessed Jan. 30, 2012]. 4 pages.

[No Author Listed], Novel test following prostate surgery could detect cancer recurrence earlier. AACR Press Release. Sep. 29, 2010. Last accessed at http://www.aacr.org/home/public--media/aacr-press-releases.aspx?d=2072 on Jan. 31, 2012. 2 pages.

[No Author Listed], Pittcon Announces 2010 Technical Program: Webcast of Selected Symposia. Press Release. Oct. 15, 2009. http://archive.constantcontact.com/fs033/1102032821298/archive/1102745632000.html [last accessed Jan. 31, 2012]. 2 pages.

(56) References Cited

OTHER PUBLICATIONS

[No Author Listed], Quanterix and STRATEC Announce Strategic Partnership. Quanterix Press Release. Aug. 16, 2011. 2 pages.
[No Author Listed], Quanterix Announces Commercial Availability of its Simoa Single Molecule Array Technology. Quanterix Press Release. Jul. 30, 2013. 2 pages.
[No Author Listed], Quanterix corporation awarded $185,000 grant from the National Cancer Institute. Quanterix Press Release. Sep. 30, 2008. Last accessed at http://www.quanterix.com/news/pressReleases/SBIR1Grant.html on Jan. 31, 2012. 1 page.
[No Author Listed], Quanterix corporation raises $15 million in series A financing. Quanterix Press Release. Aug. 25, 2008. Last accessed at http://www.quanterix.com/news/pressReleases/seriesAFunding.html on Jan. 31, 2012. 2 pages.
[No Author Listed], Quanterix Discovers Link Between Heart Attack-induced Hypoxia and Suspected Alzheimer's Disease Pathway. Quanterix Press Release. Apr. 12, 2011. Last accessed at http://www.quanterix.com/events-news/press-releases/item/146-quanterix-discovers-link-between-heart-attack-induced-hypoxia-and-suspected-alzheimer's-disease-pathway on Sep. 20, 2012.
[No Author Listed], Quanterix Launches Multiplexed Single Molecule Immunoassay Technology to Improve Diagnosis and Potential Treatment of Complex Diseases. Quanterix Press Release. Sep. 17, 2013. 2 pages.
[No Author Listed], Quanterix to Present Poster Session on Blood-based Brain Biomarker Measurements of Sports Related Brain Injury at Neuroscience. Quanterix Press Release. Nov. 4, 2013. 1 page.
[No Author Listed], Quanterix's Simoa technology to detect blood biomarker for concussion in hockey players. Quanterix Press Release. Mar. 14, 2014. 1 page.
[No Author Listed], Quanterix's Ultrasensitive Simoa™ Technology Forges New Ground with Direct Detection of Genomic DNA in Human Blood and River Water. Quanterix Press Release. Jan. 22, 2013. 2 pages.
[No Author Listed], Quanterix's Ultrasensitive Simoa™ Technology Demonstrates Equivalence with NAT and 3,000x Improvement in Sensitivity over Conventional Immunoassays for HIV Detection. Quanterix Press Release. Oct. 11, 2012. 1 page.
[No Author Listed], Scientific Principle of Simoa™ (Single Molecule Array) Technology. Whitepaper 1.0. Jul. 19, 2013. 2 pages.
[No Author Listed], Single molecule arrays for digital detection in complex samples. Quanterix Corporation. IQT Technology Focus Day. Mar. 25, 2010. PowerPoint presentation. 30 pages.
Adams et al., Encoded fiber-optic microsphere arrays for probing protein-carbohydrate interactions. Angewandte Chemie. 2003; 115:5475-5478.
Agrawal et al., Nanometer-scale mapping and single-molecule detection with color-coded nanoparticle probes. Proc Natl Acad Sci U S A. Mar. 4, 2008;105(9):3298-303. Epub Feb. 27, 2008.
Agrawal et al., Single-bead immunoassays using magnetic microparticles and spectral-shifting quantum dots. J Agric Food Chem. May 16, 2007; 55(10):3778-82. Epub Apr. 25, 2007.
Ahn et al., Detection of *Salmonella* spp. Using microsphere-based, fiber-optic DNA microarrays. Anal Chem. Aug. 1, 2005; 77(15):5041-7.
Ahn et al., Fiber-optic microarray for simultaneous detection of multiple harmful algal bloom species. Appl Environ Microbiol. Sep. 2006; 72(9):5742-9.
Albert et al., Automatic decoding of sensor types within randomly ordered, high-density optical sensor arrays. Anal Bioanal Chem. Apr. 2002; 373(8):792-802. Epub Jul. 27, 2002.
Albert et al., Cross-reactive chemical sensor arrays. Chem Rev. Jul. 12, 2000; 100(7):2595-626.
Albert et al., Information coding in artificial olfaction multisensor arrays. Anal Chem. Aug. 15, 2003; 75(16):4161-7.
Albert et al., Optical multibead arrays for simple and complex odor discrimination. Anal Chem. Jun. 1, 2001; 73(11):2501-8.
Angenendt et al., Subnanoliter enzymatic assays on microarrays. Proteomics. Feb. 2005;5(2):420-5.

Arnaud, Observing single enzymes at work. Chemical & Engineering News. Oct. 2007; 85(44): 8.
Beer et al., On-chip, real-time, single-copy polymerase chain reaction in picoliter droplets. Anal Chem. Nov. 15, 2007;79(22):8471-5. Epub Oct. 11, 2007. Abstract only.
Bencic-Nagale et al., Extending the longevity of fluorescence-based sensor arrays using adaptive exposure. Anal Chem. Oct. 1, 2005; 77(19):6155-62.
Bhat et al., Single molecule detection in nanofluidic digital array enables accurate measurement of DNA copy number. Anal Bioanal Chem. May 2009;394(2):457-67. Epub Mar. 15, 2009.
Biran et al., Optical imaging fiber-based live bacterial cell array biosensor. Anal Biochem. Apr. 1, 2003; 315(1):106-13.
Biran et al., Optical imaging fiber-based single live cell arrays: a high-density cell assay platform. Anal Chem. Jul, 1, 2002; 74(13):3046-54.
Blake et al., Phenotypic consequences of promoter-mediated transcriptional noise. Mol Cell. Dec. 28, 2006; 24(6):853-65.
Blicharz et al., Detection of inflammatory cytokines using a fiber optic microsphere immunoassay array. *Proc. SPIE.* 2006; 6380, 638010-1-638010-6.
Blicharz et al., Fiber-optic microsphere-based antibody array for the analysis of inflammatory cytokins in saliva. Anal. Chem. 2009;81(6):2106-14.
Blicharz et al., Use of colorimetric test strips for monitoring the effect of hemodialysis on salivary nitrite and uric acid in patients with end-stage renal disease: a proof of principle. Clin Chem. Sep. 2008; 54(9):1473-80. Epub Aug. 1, 2008.
Bourzac, Next-generation diagnostics: a startup can detect tiny traces of cancer markers in blood samples. Technol Rev. May 13, 2008. Last accessed at http://www.technologyreview.com/Biztech/20760/?a=f on Feb. 2, 2012. 2 pages.
Bowden et al., Development of a microfluidic platform with an optical imaging microarray capable of attomolar target DNA detection. Anal Chem. Sep. 1, 2005; 77(17):5583-8. Epub Aug. 4, 2005.
Boyden, The chemotactic effect of mixtures of antibody and antigen on polymorphonuclear leucocytes. J Exp Med. Mar. 1, 1962;115:453-66.
Brehm-Stecher et al., Single-cell microbiology: tools, technologies, and applications. Microbiol Mol Biol Rev. Sep. 2004; 68(3):538-59.
Brogan et al., Optical fiber-based sensors: application to chemical biology. Curr Opin Chem Biol. Oct. 2005; 9(5):494-500. Epub Aug. 24, 2005.
Bronk et al., Combined imaging and chemical sensing using a single optical imaging fiber. Anal Chem. Sep. 1, 1995; 67(17):2750-7.
Bronk et al., Fabrication of patterned sensor arrays with aryl azides on a polymer-coated imaging optical fiber bundle. Anal Chem. Oct. 15, 1994; 66(20):3519-20.
Burton et al., A microfluidic chip-compatible bioassay based on single-molecule detection with high sensitivity and multiplexing. Lab Chip. Apr. 7, 2010; 10(7):843-51. Epub Jan. 14, 2010.
Campian, Colored and fluorescent solid supports. Innovation and Perspectives in Solid Phase Synthesis. Ed. R. Epton, Mayflower Worldwide Limited, Birmingham. Ch. 77. 1994:469-472.
Chang et al., Digital ELISA of HIV P24 capsid protein with sensitivity of nucleic acid amplification tests. 2012 AACC Meeting. Los Angeles, CA. Abstract and Poster. 2012. 2 pages.
Chang et al., Prototype digital immunoassay for troponin I with sub-femtomolar sensitivity. 2013 AACC Meeting. Houston, TX. Abstract and Poster. 2013. 2 pages.
Chang et al., Simple diffusion-constrained immunoassay for p24 protein with the sensitivity of nucleic acid amplification for detecting acute HIV infection. J Virol Methods. Mar. 2013;188(1-2):153-60. doi: 10.1016/j.jviromet.2012.08.017. Epub Oct. 2, 2012.
Chang et al., Single molecule enzyme-linked immunosorbent assays: theoretical considerations. J Immunol Methods. Apr. 30, 2012;378(1-2):102-15. doi: 10.1016/j.jim.2012.02.011. Epub Apr. 30, 2013. 28 pages.
Chen et al., Microfabricated arrays of cylindrical wells facilitate single-molecule enzymology of alpha-chymotrypsin. Biotechnol Prog. Jul.-Aug. 2009; 25(4):929-37.
Chin et al., Editor's Choice: Distinctive individualism. Science. Apr. 4, 2008;320:21.

(56) References Cited

OTHER PUBLICATIONS

Chon et al., Characterization of single-cell migration using a computer-aided fluorescence time-lapse videomicroscopy system. Anal Biochem. Oct. 15, 1997;252(2):246-54.

Deutsch et al., Apparatus for high-precision repetitive sequential optical measurement of living cells. Cytometry. Jul. 1, 1994; 16(3):214-26.

Dicesare et al., Individual cell migration analysis using fiber-optic bundles. Anal Bioanal Chem. May 2005; 382(1):37-43. Epub Apr. 1, 2005.

Dickinson et al., A chemical-detecting system based on a cross-reactive optical sensor array. Nature. Aug. 22, 1996; 382(6593):697-700.

Dickinson et al., Convergent, self-encoded bead sensor arrays in the design of an artificial. Anal Chem. Jun. 1, 1999; 71(11):2192-8.

Dickinson et al., Current trends in 'artificial-nose' technology. Trends Biotechnol. Jun. 1998; 16(6):250-8.

Duffy et al., Detection of prostate specific antigen (PSA) in the serum of radical prostatectomy patients at femtogram per milliliter levels using digital ELISA (AccuPSATM) based on single molecule arrays (SiMoA). AACC Meeting Poster. 2010. 1 page.

Duffy, Immunoassays with Broad Dynamic Ranges based on Combining Digital and Digitally Enhanced Analog Detecion of Enzyme Labels. Oak Ridge Conference. Presentation. Apr, 15, 2011. 16 pages.

Duffy, Single Molecule Arrays (Simoa) for Ultrasensitive Protein Detection in Companion Diagnostics. Next Generation DX Summit. Aug. 22, 2012. PowerPoint presentation. 18 slides.

Duffy, Ultra-sensitive protein detection using single molecule arrays (Simoa): the potential for detecting single molecules of botulinum toxin. The Botulinum J. 2012;2(2):164-7.

Egner et al., Tagging in combinatorial chemistry: the use of coloured and flurorescent beads. Chem Commun. 1997; 735-736.

Eid et al., Real-time DNA sequencing from single polymerase molecules. Science. Jan. 2, 2009; 323(5910):133-8. Epub Nov. 20, 2008.

Ekins et al., Single-molecule ELISA. Clin Chem. Mar. 2011;57(3):372-5. Epub Oct. 13, 2010. Papers in press. Oct. 13, 2010. pp. 1-3.

English et al., Ever-fluctuating single enzyme molecules: Michaelis-Menten equation revisited. Nat Chem Biol. Feb. 2006; 2(2):87-94. Epub Dec. 25, 2005.

Epstein et al., Combinatorial decoding: an approach for universal DNA array fabrication. J Am Chem Soc. Nov. 12, 2003; 125(45):13753-9.

Epstein et al., Fluorescence-based nucleic acid detection and microarrays. Analytica Chimica Acta. 2002; 469:3-36.

Epstein et al., High-density fiber-optic genosensor microsphere array capable of zeptomole detection limits. Anal Chem. Apr. 15, 2002; 74(8):1836-40.

Epstein et al., High-density, microsphere-based fiber optic DNA microarrays. Biosens Bioelectron. May 2003; 18(5-6):541-6.

Epstein, et al., Fluorescence-based fibre optic arrays: a universal platform for sensing. Chem Soc Rev. Jul. 2003; 32(4):203-14.

Ferguson et al., A fiber-optic DNA biosensor microarray for the analysis of gene expression. Nat Biotechnol. Dec. 1996; 14(13):1681-4.

Ferguson et al., High-density fiber-optic DNA random microsphere array. *Anal Chem.* Nov. 15, 2000; 72(22):5618-24.

Ferguson et al., Simultaneous monitoring of pH, $CO_2$ and $O_2$ using an optical imaging fiber. Analytica Chimica Acta. 1997; 340(1-3):123-131.

Fister et al., Counting single chromophore molecules for ultrasensitive analysis and separations on microchip devices. Analytical Chemistry. 1998; 70:431-437.

Fulton et al., Advanced multiplexed analysis with the FlowMetrix system. Clin Chem. Sep. 1997; 43(9):1749-56.

Furka et al., General method for rapid synthesis of multicomponent peptide mixtures. Int J Pept Protein Res. Jun. 1991;37(6):487-93.

Gebel, Molecule counting made easy. Anal Chem. Sep. 1, 2009; 7130-7131.

Giaever et al., Micromotion of mammalian cells measured electrically. Proc Natl Acad Sci U S A. Sep. 1, 1991;88(17):7896-900.

Gorris et al., Analytical chemistry on the femtoliter scale. Angew Chem Int Ed. 2010; 49:2-18.

Gorris et al., Mechanistic aspects of horseradish peroxidase elucidated through single-molecule studies. J Am Chem Soc. May 6, 2009; 131(17):6277-82.

Gorris et al., Optical-fiber bundles. FEBS J. Nov. 2007; 274(21):5462-70. Epub Oct. 12, 2007.

Gorris et al., Stochastic inhibitor release and binding from single-enzyme molecules. Proc Natl Acad Sci U S A. Nov. 6, 2007; 104(45):17680-5. Epub Oct. 26, 2007.

Härma et al., Europium nanoparticles and time-resolved fluorescence for ultrasensitive detection of prostate-specific antigen. Clin Chem. Mar. 2001; 47(3):561-8.

Härma et al., Miniature single-particle immunoassay for prostate-specific antigen in serum using recombinant Fab fragments. Clin Chem. Nov. 2000; 46(11):1755-61.

Härma et al., Zeptomole detection sensitivity of prostate-specific antigen in a rapid microtitre plate assay using time-resolved fluorescence. Luminescence. Nov.-Dec. 2000;15(6):351-5.

Hashida et al., Immune complex transfer enzyme immunoassay that is more sensitive and specific than western blotting for detection of antibody immunoglobulin G to human immunodeficiency virus type 1 in serum with recombinant pol and gag proteins as antigens. Clin Diagn Lab Immunol. Sep. 1995; 2(5):535-41.

Haugland, Handbook: A Guide to Fluorescent Probes and Labeling Technologies. Invitrogen, Eugene, OR. Molecular Probes, US. pp. 473-538.

He et al., Selective encapsulation of single cells and subcellular organelles into picoliter- and femtoliter-volume droplets. Anal Chem. Mar. 15, 2005; 77(6):1539-44.

Healey et al., Fiberoptic DNA sensor array capable of detecting point mutations. Anal Biochem. Sep. 5, 1997; 251(2):270-9.

Healey et al., Multianalyte biosensors on optical imaging bundles. Biosens Bioelectron. 1997; 12(6):521-9.

Healey et al., Photodeposition of micrometer-scale polymer patterns on optical imaging fibers. Science. Aug. 25, 1995; 269(5227):1078-80.

Hindson et al., High-throughput droplet digital PCR system for absolute quantitation of DNA copy number. Anal Chem. Nov. 15, 2011;83(22):8604-10. Epub Oct. 28, 2011.

Hirano et al., A novel method for DNA molecular counting. Nucleic Acids Symp Ser. 2000;(44):157-8.

Hirschfeld, Remote and in-situ analysis. Anal Chem. 1986; 324:618-624.

Hunsaker et al., Nucleic acid hybridization assays employing dA-tailed capture probes. II. Advanced multiple capture methods. Anal Biochem. Sep. 1989; 181(2):360-70.

Johnson et al., Identification of multiple analytes using an optical sensor array and pattern recognition neural networks. Analytical Chemistry. 1997; 69(22):4641-4648.

Joos, Quanterix Web Symposium: Immunoassays in Multiplex for Biomarker Discovery and Validation. Presentation. Feb. 27, 2013. 43 pages.

Kiss et al., High-throughput quantitative polymerase chain reaction in picoliter droplets. Anal Chem. Dec. 1, 2008;80(23):8975-81.

Kremsky et al., Immobilization of DNA via oligonucleotides containing an aldehyde or carboxylic acid group at the 5' terminus. Nucleic Acids Res. Apr. 10, 1987; 15(7):2891-909.

Kuang et al., Living bacterial cell array for genotoxin monitoring. Anal Chem. May 15, 2004; 76(10):2902-9.

Kuang et al., Monitoring "promiscuous" drug effects on single cells of multiple cell types. *Anal Biochem.* Oct. 15, 2005; 345(2):320-5.

Kuang et al., Simultaneously monitoring gene expression kinetics and genetic noise in single cells by optical well arrays. Anal Chem. Nov. 1, 2004; 76(21):6282-6.

Lafratta et al., Very high density sensing arrays. Chem Rev. Feb. 2008; 108(2):614-37. Epub Jan. 30, 2008.

Lee et al., A fiber-optic microarray biosensor using aptamers as receptors. Anal Biochem. Jun. 15, 2000; 282(1):142-6.

(56) References Cited

OTHER PUBLICATIONS

Li et al., Detection of single-molecule DNA hybridization using enzymatic amplification in an array of femtoliter-sized reaction vessels. J Am Chem Soc. Sep. 24, 2008; 130(38):12622-3. Epub Sep. 3, 2008.
Li et al., Molecule by molecule direct and quantitative counting of antibody-protein complexes in solution. Anal Chem. Aug. 1, 2004; 76(15):4446-51.
Lu et al., Single-molecule enzymatic dynamics. Science. Dec. 4, 1998; 282(5395):1877-82.
Luo et al., Single-molecule and ensemble fluorescence assays for a functionally important conformational change in T7 DNA polymerase. Proc Natl Acad Sci U S A. Jul. 31, 2007; 104(31):12610-5. Epub Jul. 18, 2007.
Melin et al., Microfluidic large-scale integration: the evolution of design rules for biological automation. Annu Rev Biophys Biomol Struct. 2007; 36:213-31.
Michael et al., Combined imaging and chemical sensing of fertilization-induced acid release from single sea urchin eggs. Anal Biochem. Sep. 10, 1999; 273(2):168-78.
Michael et al., Randomly ordered addressable high-density optical sensor arrays. Anal Chem. Apr. 1, 1998; 70(7):1242-8.
Monk et al., Fabrication of gold microtubes and microwires in high aspect ratio capillary arrays. J Am Chem Soc. Sep. 22, 2004; 126(37):11416-7.
Monk et al., Optical fiber-based biosensors. Anal Bioanal Chem. Aug. 2004; 379(7-8):931-45. Epub Jun. 23, 2004.
Monk et al., Progress toward the dermination of $Sr^{2+}$ in highly basic solutions using imagining optical fiber sensor arrays. J. Mater. Chem. 2005; 15:4361-4366.
Morrison et al., Nanoliter high throughput quantitative PCR. Nucleic Acids Res. 2006;34(18):e123. Epub Sep. 25, 2006.
Munkholm et al., Polymer modification of fiber optic chemical sensors as a method of enhancing fluoescence signal for pH measurement. Anal Chem. 1986; 58:1427-1430.
Nagai et al., High-throughput PCR in silicon based microchamber array. Biosens Bioelectron. Dec. 2001; 16(9-12):1015-9.
Nalefski et al., Single-molecule detection for femtomolar quantification of proteins in heterogeneous immunoassays. Clin Chem. Nov. 2006; 52(11):2172-5.
Nam et al., Nanoparticle-based bio-bar codes for the ultrasensitive detection of proteins. Science. Sep. 26, 2003;301(5641):1884-6.
Niemeyer et al., Combination of DNA-directed immobilization and immuno-PCR: very sensitive antigen detection by means of self-assembled DNA-protein conjugates. Nucleic Acids Res. Aug. 15, 2003; 31(16):e90, 7 pages.
Okrongly, Single Molecule Enzyme Detection and Application to Immunoassay: Implications for Personalized Medicine. Abstract and Presentation. ISE International Conference. May 4, 2010. 24 pages.
Panova et al., In situ fluorescence imaging of localized corrosion with a pH-sensitive imaging fiber. Anal Chem. Apr. 15, 1997; 69(8):1635-41.
Pantano et al., Analytical applications of optical imaging fibers. Anal Chem. Aug. 1, 1995; 67(15):481A-487A.
Pantano et al., Ordered nanowell arrays. Chemistry of Materials. 1996;8: 2832-2835.
Pantano et al., Toward a near-field optical array. Rev. Sci. Instrum. 1997; 68(3): 1357-1359.
Peterson et al., Fiber optic pH probe for physiological use. Anal Chem. May 1980; 52(6):864-9.
Prabhakar et al., Simultaneous quantification of proinflammatory cytokines in human plasma using the LabMAP assay. J Immunol Methods. Feb. 1, 2002;260(1-2):207-18.
Preiser et al., Quantitative molecular virology in patient management. Journal of Clinical Pathology. 2000;53:76-83.
Qiu et al., Fluorescence single-molecule counting assays for high-sensitivity detection of cytokines and chemokines. Clin Chem. Nov. 2007; 53(11):2010-2.

Randle et al., Integrating molecular detection and response to create self-signalling antibodies. Biochem Biophys Res Commun. Nov. 12, 2004; 324(2):504-10.
Rissin et al., Attomolar detection of proteins in serum using single molecule enzyme-linked immunosorbent assays. Quanterix Corporation. Oak Ridge Conference, San Jose, CA. Poster. 2010. 1 page.
Rissin et al., Digital concentration readout of single enzyme molecules using femtoliter arrays and Poisson statistics. Nano Lett. Mar. 2006; 6(3):520-3.
Rissin et al., Digital readout of target binding with attomole detection limits via enzyme amplification in femtoliter arrays. J Am Chem Soc. May 17, 2006; 128(19):6286-7.
Rissin et al., Distinct and long-lived activity states of single enzyme molecules. J Am Chem Soc. Apr. 16, 2008; 130(15):5349-53. Epub Mar. 5, 2008.
Rissin et al., Duplexed sandwich immunoassays on a fiber-optic microarray. Anal Chim Acta. Mar. 30, 2006; 564(1):34-9. Epub Nov. 11, 2005.
Rissin et al., Immunoassays with broad dynamic ranges based on combining digital and digitally-enhanced analog detection of enzyme labels. Oak Ridge Conference. Poster 7 and Abstract. Apr. 14-15, 2011. 2 pages.
Rissin et al., Multiplexed single molecule immunoassays. Lab Chip. Aug. 7, 2013;13(15):2902-11. doi: 10.1039/c3lc50416f.
Rissin et al., Simultaneous detection of single molecules and singulated ensembles of molecules enables immunoassays with broad dynamic range. Anal Chem. Mar. 15, 2011;83(6):2279-85. Epub Feb. 23, 2011.
Rissin et al., Single-molecule enzyme-linked immunosorbent assay detects serum proteins at subfemtomolar concentrations. Nat Biotechnol. Jun. 2010; 28(6):595-9 and supplemental pages. Epub May 23, 2010.
Roeffaers et al., Single-molecule fluorescence spectroscopy in (bio)catalysis. Proc Natl Acad Sci U S A. Jul. 31, 2007; 104(31):12603-9. Epub Jul. 30, 2007.
Rondelez et al., Highly coupled ATP synthesis by F1-ATPase single molecules. Nature. Feb. 17, 2005; 433(7027):773-7.
Rondelez et al., Microfabricated arrays of femtoliter chambers allow single molecule enzymology. Nat Biotechnol. Mar. 2005; 23(3):361-5. Epub Feb. 20, 2005.
Rotman, Measurement of activity of single molecules of beta-D-galactosidase. Proc Natl Acad Sci U S A. Dec. 15, 1961; 47:1981-91.
Schauer et al., A cross-reactive, class-selective enzymatic array assay. J Am Chem Soc. Sep. 26, 2001; 123(38):9443-4.
Schmidinger, et al., Inhibitor and protein microarrays for activity-based recognition of lipolytic enzymes. Chembiochem. Mar. 2006; 7(3):527-34.
Schweitzer et al., Inaugural article: immunoassays with rolling circle DNA amplification: a versatile platform for ultrasensitive antigen detection. Proc Natl Acad Sci U S A. Aug 29, 2000; 97(18):10113-9.
Seydack, Nanoparticle labels in immunosensing using optical detection methods. Biosens Bioelectron. Jun. 15, 2005; 20(12):2454-69. Epub Dec. 16, 2004.
Shen et al. High-throughput SNP genotyping on universal bead arrays. Mutat Res. Jun. 3, 2005;573(1-2):70-82.
Shepard et al., Array-based binary analysis for bacterial typing. Anal Chem. Jan. 1, 2005; 77(1):319-26.
Song et al., Detecting biological warfare agents. Emerg Infect Dis. Oct. 2005; 11(10):1629-32.
Song et al., Direct Detection of Bacterial DNA and viral RNA at Subfemtomolar Concentrations Using Single Molecule Arrays (Simoa). 2013 Oakridge Conference. Baltimore, MD. Abstract and Poster. 2013. 2 pages.
Song et al., Direct detection of bacterial genomic DNA at sub-femtomolar concentrations using single molecule arrays. Anal Chem. Feb. 5, 2013;85(3):1932-9. doi: 10.1021/ac303426b. Epub Jan. 18, 2013. Supporting Information Included.
Song et al., Fiber-optic microsphere-based arrays for multiplexed biological warfare agent detection. Anal Chem. Feb. 15, 2006; 78(4):1023-33.

(56) References Cited

OTHER PUBLICATIONS

Song et al., Single molecule measurements of tumor necrosis factor α andinterleukin-6 in the plasma of patients with Crohn's disease. J Immunol Methods Sep. 30, 2011;372(1-2):177-86. Epub Jul. 27, 2011.
Soukka et al., Supersensitive time-resolved immunofluorometric assay of free prostate-specific antigen with nanoparticle label technology. Clin Chem. 2001; 47(7):1269-78.
Stamou et al., Self-assembled microarrays of attoliter molecular vessels. Angew Chem Int Ed Engl. Nov. 24, 2003; 42(45):5580-3.
Steemers et al., Multi-analyte sensing: from site-selective deposition to randomly ordered addressable optical sensors. Microchimica Acta. 1999; 131:99-105.
Steemers et al., Screening unlabeled DNA targets with randomly ordered fiber-optic gene arrays. Nat Biotechnol. Jan. 2000; 18(1):91-4.
Stitzel et al., Array-to-array transfer of an artificial nose classifier. Anal Chem. Nov. 1, 2001; 73(21):5266-71. Epub Sep. 28, 2001.
Subbaraman, Detecting single cancer molecules. Technol Rev. Jun. 3, 2010. Last accessed at http://www.technologyreview.com/biomedicine/25462/ on Jan. 31, 2012. 2 pages.
Sykes et al., Quantitation of targets for PCR by use of limiting dilution. Biotechniques. 1992;13(3):444-9.
Szunerits et al., Aluminum surface corrosion and the mechanism of inhibitors using pH and metal ion selective imaging fiber bundles. Analytical Chemistry. 2002;74(4): 886-94.
Szunerits et al., Fabrication of an optoelectochemical microring array. Analytical Chemistry. 2002; 74(7):1718-23.
Szunerits et al., Spatially resolved electrochemiluminescence on an array of electrode tips. Anal Chem. Sep. 1, 2003; 75(17):4382-8.
Szunerits et al., The use of optical fiber bundles combined with electrochemistry for chemical imaging. Chemphyschem. Feb. 17, 2003; 4(2):186-92. Epub Feb. 7, 2003.
Szurdoki et al., A duplexed microsphere-based fluorescent immunoassay. Anal Biochem. Apr. 15, 2001; 291(2):219-28.
Tam et al., An imaging fiber-based optical tweezer array for microparticle array assembly. Applied Physics Letters. 2004; 84(21):4289-4291.
Tam et al., Fabrication and optical characterization of imaging fiber-based nanoarrays. Talanta. Sep. 15, 2005; 67(3):498-502. Epub Jul. 27, 2005.
Tam et al., Parallel microparticle manipulation using an imaging fiber bundle-based optical tweezer array and a digital micromirror device. Applied Physics Letters. 2006; 89:194101/1-194101/3.
Tan et al., Monitoring the reactions of single enzyme molecules and single metal ions. Anal. Chem. 1997; 69:4242-4248.
Tanen et al., Development of an Ultrasensitive Digital Immunossay on the Single Molecule Array (SimoaTM) Platform. 2014 AAPS Annual Meeting. San Diego, CA. Abstract and Poster. Nov. 2-6, 2014. 2 pages.
Taylor et al., Application of high-density optical microwell arrays in a live-cell biosensing system. Anal Biochem. Feb. 15, 2000; 278(2):132-42.
Tessler et al., Protein quantification in complex mixtures by solid phase single-molecule counting. Anal Chem. Sep. 1, 2009; 81(17):7141-8.
Thaxton et al., Nanoparticle-based bio-barcode assay redefines "undetectable" PSA and biochemical recurrence after radical prostatectomy. Proc Natl Acad Sci U S A. Nov. 3, 2009;106(44):18437-42. Epub Oct. 19, 2009.
Timmerman, Quanterix CEO sets sight on early detection of cancer, neurological diseases in the blood. Xconomy. Jan. 19, 2010. Last accessed at http://www.xconomy.com/boston/2010/01/19/quanterix-ceo-sets-sight-on-early-detection-of-cancer-neurological-diseases-in-the-blood/ on Jan. 31, 2012. 4 pages.
Todd et al., Ultrasensitive flow-based immunoassays using single-molecule counting. Clin Chem. Nov. 2007; 53(11):1990-5. Epub Sep. 21, 2007.
Tromberg et al., Development of antibody-based fiber-optic sensors for detection of a benzo[a]pyrene metabolite. Anal Chem. Sep. 15, 1988; 60(18):1901-8.
Tsongalis, Branched DNA technology in molecular diagnostics. Am J Clin Pathol. Sep. 2006;126(3):448-53.
Ueberfeld et al., Reversible ratiometric probe for quantitative DNA measurements. Anal Chem. Feb. 15, 2004; 76(4):947-52. Epub Jan. 20, 2004.
Vo-Dinh et al., Phase-resolved fiber-optics fluoroimmunosensor. Applied Spectroscopy. 1990; 44(1):128-132.
Vogelstein et al., Digital PCR. Proc Natl Acad Sci U S A. Aug. 3, 1999;96(16):9236-41.
Walt et al., Biosensing with live cells using a high-density optical fiber array. Radiation Research. 2001; 156(4):442.
Walt et al., Microsensor arrays for saliva diagnostics. Ann N Y Acad Sci. Mar. 2007; 1098:389-400.
Walt et al., Optical sensor arrays for odor recognition. Biosens Bioelectron. Sep. 15, 1998; 13(6):697-9.
Walt et al., Ultrasensitive detection of proteins using single molecule arrays (SiMoA). Presented Mar. 1, 2010. Pittcon. Abstract and PowerPoint presentation. 32 pages.
Walt, An array of solutions, fiber arrays contribute to studies of individual cellular behavior and response. SPIE'S oemagazine. 2005; 19-21.
Walt, Fiber optic array biosensors. Biotechniques. Nov. 2006; 41(5):529, 531, 533, 535 passim.
Walt, Fiber optic imaging sensors. Accounts of Chemical Research. 1998; 31:267-278.
Walt, Imaging optical sensor arrays. Curr Opin Chem Biol. Oct. 2002; 6(5):689-95.
Walt, Optical methods for single molecule detection and analysis. Anal Chem. Feb. 5, 2013;85(3):1258-63. doi: 10.1021/ac3027178. Epub Dec. 19, 2012.
Walt, Techview: molecular biology. Bead-based fiber-optic arrays. Science. Jan. 21, 2000; 287(5452):451-2.
Wang et al., Quantification of protein based on single-molecule counting by total internal reflection fluorescence microscopy with adsorption equilibrium. Anal Chim Acta. May 2, 2007; 590(1):104-9. Epub Mar. 15, 2007.
Warren et al., Transcription factor profiling in individual hematopoietic progenitors by digital RT-PCR. Proc Natl Acad Sci U S A. Nov. 21, 2006;103(47):17807-12. Epub Nov. 10, 2006.
Whitaker et al., Fiber-based single cell analysis of reporter gene expression in yeast two-hybrid systems. Anal Biochem. Jan. 1, 2007; 360(1):63-74. Epub Oct. 30, 2006.
Whitaker et al., Multianalyte single-cell analysis with multiple cell lines using a fiber-optic array. Anal Chem. Dec. 1, 2007; 79(23):9045-53. Epub Nov. 1, 2007.
White et al., An olfactory neuronal network for vapor recognition in an artificial nose. Biol Cybern. Apr. 1998; 78(4):245-51.
White et al., Rapid analyte recognition in a device based on optical sensors and the olfactory system. Analytical Chemistry. 1996; 68(13):2191-2202.
Wilson et al., Development of AccuPSA™, a novel digital immunoassay for sub-femtomolar measurement of PSA in post radical prostatectomy patients. AACR Molecular diagnostics in Cancer Therapeutic Development Abstract and Poster. 2011. 1 page.
Wilson et al., Fifth-generation digital immunoassay for prostate-specific antigen by single molecule array technology. Clin Chem. Dec. 2011;57(12):1712-21. Epub Oct. 13, 2011.
Wilson et al., Simoa™ HD-1: a fully automated digital immunoassay analyzer capable of single molecule counting, sub-femtomolar sensitivity, and multiplexing. 2014 AACC Meeting. Chicago, IL. Abstract and Poster. 2014. 2 pages.
Wilson, Serum Measurement of Hypoxia-Induced Amyloid Beta 1-42 Following Resuscitation from Cardiac Arrest. Abstract and Poster. American Academy of Neurology Annual Meeting. Apr. 9, 2011. 2 pages.
Wu et al., Development and preliminary clinical validation of a high sensitivity assay for cardiac troponin using a capillary flow (single molecule) fluorescence detector. Clin Chem. Nov. 2006; 52(11):2157-9.

(56) References Cited

OTHER PUBLICATIONS

Xie et al., Optical studies of single molecules at room temperature. Annu Rev Phys Chem. 1998; 49:441-80.

Xie et al., Single gold nanoparticles counter: an ultrasensitive detection platform for one-step homogeneous immunoassays and DNA hybridization assays. J Am Chem Soc. Sep. 9, 2009;131(35):12763-70.

Xue et al., Differences in the chemical reactivity of individual molecules of an enzyme. Nature. Feb. 23, 1995; 373(6516):681-3.

Yan et al., Analyzing polyubiquitin chains upon ubiquitin activating enzyme inhibition from cell culture & tumor lysates using the Quanterix's single molecule array (Simoa) technology. 2013 Society for the Laboratory Automation & Screening Annual Meeting. Orlando, FL. Abstract and Poster. 2013. 2 pages.

Young et al., Integrating high-content screening and ligand-target prediction to identify mechanism of action. Nat Chem Biol. Jan. 2008; 4(1):59-68. Epub Dec. 9, 2007.

Ke et al., Improving precision of proximity ligation assay by amplified single molecule detection. PLoS One. Jul. 16, 2013;8(7):e69813. doi: 10.1371/journal.pone.0069813. 5 pages.

\* cited by examiner

```
  1 tgtctcgata tgatagtctg caacgattca tgttgtaggc tatttaattt tacaaataag
 61 gctaaatata taagttctga caccyaaaat atagaaaata cataaaagta agtatagtta
121 ttttattata attattaaat ttttattaat taattgtaaa aatgtagaat tataattaat
181 taacgtttaa tattaaaatt aactaaaaag aaagaggtgt tagttatgac agaatactta
241 ttaagtgctg gcatatgtat ggcaattgtt tcaatattac ttatagggat ggctatcagt
301 aatgtttcga aagggcaata cgcaaagagg ttttctcttt tcgctactag ttgcttagtg
361 ttaactttag ttgtagtttc aagtctaagt a/gctcagcaa atgcatcaca aacagataac
421 ggcgtaaata gaagtggttc tgaagatcca acagtatata gtgcaacttc aactaaaaaa
481 ttacataaag aacctgcgac tttaattaaa gcgattgatg gtgatacggt taattaatg
541 tacaaaggtc aaccaatgac attcagacta ttattgtttg atacacctga aacaaagcat
601 cctaaaaaag gtgtagagaa atatggtcct gaagcaagtg catttacgaa aaaaatggta
661 gaaaatgcaa agaaaattga agtcgagttt gacaaaggtc aaagaactga taaatatgga
721 cgtggcttag cgtatattta tgctgatgga aaatggtaa acgaa/gctt agttcgtcaa
781 ggcttggcta aagttgctta tgtttacaaa cctaacaata cacatgaaca acatttaaga
841 aaaagtgaag cacaagcgaa aaaagagaaa ttaaatattt ggagcgaaga caacgctgat
901 tcaggtcaat aatgctcatt gtaaaagtgt cactgctgct agtggcactt ttataatttt
961 tagatc (SEQ ID NO: 50)
``` a/gct - cutting site for AluI capture probes
detection probes for fragment 1
detection probes for fragment 2
detection probes for fragment 3

Target sequence (1 kbp) cloned into pUC-57 vector, ~2.7 kbp

Fig. 3

DETECTION OF DNA OR RNA USING SINGLE MOLECULE ARRAYS AND OTHER TECHNIQUES

CROSS-REFERENCE TO RELATED APPLICATIONS

This application is a national stage filing under 35 U.S.C. § 371 of international application PCT/US2014/011730, filed Jan. 15, 2014, which claims priority under 35 U.S.C. § 119(e) to U.S. Provisional Application Ser. No. 61/752,545, filed Jan. 15, 2013, the contents of each of which are incorporated by reference herein in their entirety.

FIELD OF THE INVENTION

Described herein are methods and systems for detecting DNA or RNA using single molecules array or other techniques in a fluid sample. In some cases, a measure of the concentration of the DNA or RNA in the fluid sample is determined.

BACKGROUND OF THE INVENTION

The sensitive measurement of nucleic acids (NAs) is important in a number of fields such as clinical diagnostics, environmental monitoring, detection of biological threats, and food safety. The detection and quantification of NAs at low concentrations from viruses and bacteria is especially important for the early diagnosis of infectious diseases and testing of blood supplies.

The gold standard method for detecting DNA is the polymerase chain reaction (PCR). PCR is now capable of routinely detecting <100 copies of NA per sample (volume ~5 µL), and real time PCR assays for HIV, for example, are capable of detecting down to 20 copies of viral RNA per mL. PCR is based on the exponential amplification of target molecules by repeated cycles of molecular replication. PCR has proven to be robust as well as sensitive, and has found widespread use in clinical diagnostics and research. PCR does, however, have drawbacks—primarily from the reliance on polymerases—that limit its usefulness in some applications. First, polymerases are susceptible to inhibition from sample components that can result in false negative results in clinical, environmental, food, and forensic samples. As a result, PCR requires careful sample preparation to purify DNA in order for the amplification reaction to be performed. DNA purification makes automation of PCR more complex, with each type of sample often requiring a different preparation method. Second, PCR can be prone to false positive results from erroneous amplification of non-target sequences. Third, PCR is relatively expensive compared to other sensitive analytical techniques, such as immunoassays. Methods that do not rely on the replication of DNA, i.e., that directly detect the target molecules without polymerases, are promising alternatives to PCR.

Accordingly, improved methods are needed.

SUMMARY

In some embodiments, a method for determining detecting or measuring the concentration of DNA or RNA molecules in sample is provided comprising fragmenting DNA or RNA from a sample to form fragmented DNA or RNA sequences; exposing the fragmented DNA or RNA sequences to at least a first type of capture object and a second type of capture object, wherein at least a portion of the fragmented DNA or RNA associates with the least one of the first type of capture object and the second type of capture objection object, wherein the first type of capture object comprises a first capture probe comprising a first nucleic acid sequence complimentary to a portion of a sequence contained in the DNA or RNA and the second type of capture object comprises a second capture probe comprising a second nucleic acid sequence complimentary to a portion of a sequence contained in the DNA or RNA, wherein the first sequence and the second sequence are different; and analyzing a portion of the sample from the exposing step to determine the number of fragmented DNA or RNA sequences associated with at least one of the first type of capture object and the second type of capture object.

In some embodiments, a method for determining detecting or measuring the concentration of DNA or RNA molecules in a sample is provided comprising fragmenting DNA or RNA from the sample to form fragmented DNA or RNA sequences; exposing the fragmented DNA or RNA sequences to at least a first type of binding ligand and a second type of binding ligand, wherein at least a portion of the fragmented DNA or RNA associates with at least one of the first type of binding ligand and/or the second type of binding ligand, wherein the first type of binding ligand comprises a first nucleic acid sequence complimentary to a first portion of a sequence contained in the DNA or RNA and second type of binding ligand comprises a second nucleic acid sequence complimentary to a second portion of a sequence contained in the DNA or RNA, wherein the first nucleic acid sequence and the second nucleic acid sequence are different; and analyzing a portion of the sample from the exposing step to determine the number of fragmented DNA or RNA sequences associated at least one of the first type of binding ligand and the second type of binding ligand, wherein the first type of binding ligand and the second type of binding ligand produce substantially similar signals.

BRIEF DESCRIPTION OF THE DRAWINGS

Other aspects, embodiments, and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

FIG. 3 depicts an exemplary sequence design for detecting a gene using multiple capture probes attached to four separate bead populations and multiple biotinylated detection probes, according to some embodiments;

DETAILED DESCRIPTION

Figure 1:
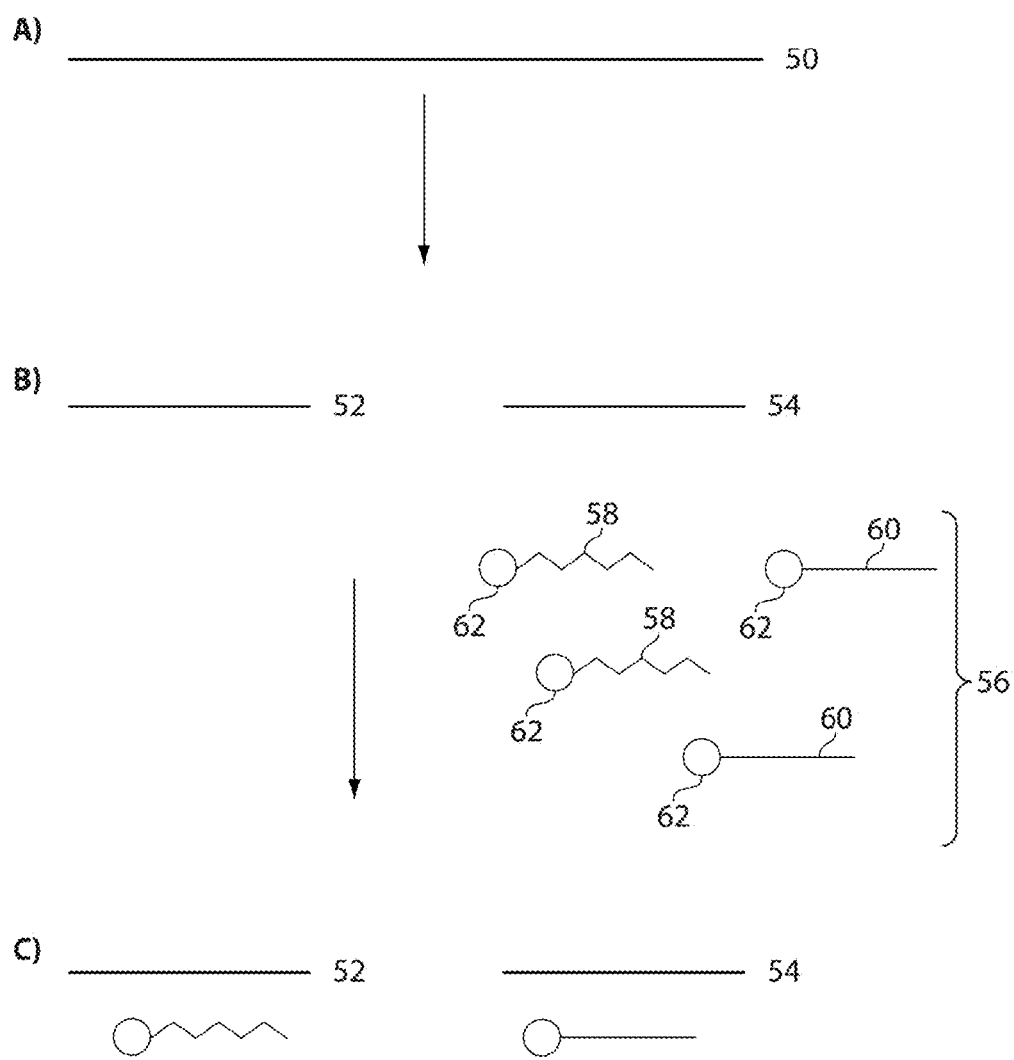
FIG. 1 depicts a non-limiting example of a method utilizing a plurality of types of capture probes, according to some embodiments.

Described herein are methods and systems that may in certain embodiments be employed for the detection and/or quantification of DNA or RNA in a sample. The subject matter of the present invention involves, in some cases, interrelated products, alternative solutions to a particular problem, and/or a plurality of different uses of one or more systems and/or articles.

In some embodiments, methods based on the direct detection of single DNA and/or RNA molecules derived from DNA and/or RNA (e.g., genomic DNA and/or RNA) are provided (e.g., without use of PCR or another amplification technique). In other embodiments, DNA and/or RNA may be detected, in part, using amplification techniques.

Single molecule assays for direct detection and quantification of analyte molecules using the single molecule array technology are known in the art. Exemplary single molecule array assay technology that is suitable for adaption for use in certain embodiments of the presently described assays and methods has been described previously, for example, see U.S. Pat. No. 8,460,879 (Ser. No. 11/707,385), issued Jun. 11, 2013, entitled "METHODS AND ARRAYS FOR TARGET ANALYTE DETECTION AND DETERMINATION OF TARGET ANALYTE CONCENTRATION IN SOLUTION", by Walt et al.; U.S. Pat. No. 8,460,878 (Ser. No. 11/707,383), issued Jun. 11, 2013, entitled "METHODS AND ARRAYS FOR DETECTING CELLS AND CELLULAR COMPONENTS IN SMALL DEFINED VOLUMES", by Walt et al.; U.S. Pat. No. 8,492,098 (Ser. No. 11/707,384), issued Jul. 23, 2013, entitled "METHODS AND ARRAYS FOR TARGET ANALYTE DETECTION AND DETERMI- NATION OF REACTION COMPONENTS THAT AFFECT A REACTION", by Walt et al.; International Patent Publication No. WO 2009/029073 (International Patent Application No. PCT/US2007/019184), filed Aug. 30, 2007, entitled "METHODS OF DETERMINING THE CONCENTRATION OF AN ANALYTE IN SOLUTION", by Walt et al.; U.S. Patent Application Publication No. US-2010-0075862 (Ser. No. 12/236,484), filed Sep. 23, 2008, entitled "HIGH SENSITIVITY DETERMINATION OF THE CONCENTRATION OF ANALYTE MOLECULES OR PARTICLES IN A FLUID SAMPLE", by Duffy et al.; U.S. Pat. No. 8,222,047 (Ser. No. 12/236,486), issued Jul. 17, 2012, entitled "ULTRA-SENSITIVE DETECTION OF MOLECULES ON SINGLE MOLECULE ARRAYS", by Duffy et al.; U.S. Patent Application Publication No. US-2010-0075439 (Ser. No. 12/236,488), filed Sep. 23, 2008, entitled "ULTRA-SENSITIVE DETECTION OF MOLECULES BY CAPTURE-AND-RELEASE USING REDUCING AGENTS FOLLOWED BY QUANTIFICATION", by Duffy et al.; International Patent Publication No. WO2010/039179 (International Patent Application No. PCT/US2009/005248), filed Sep. 22, 2009, entitled "ULTRA-SENSITIVE DETECTION OF MOLECULES OR ENZYMES", by Duffy et al.; U.S. Patent Application Publication No. US-2010-0075355 (Ser. No. 12/236,490), filed Sep. 23, 2008, entitled "ULTRA-SENSITIVE DETECTION OF ENZYMES BY CAPTURE-AND-RELEASE FOLLOWED BY QUANTIFICATION", by Duffy et al.; U.S. Pat. No. 8,236,574 (Ser. No. 12/731,130), issued Aug. 7, 2012, entitled "ULTRA-SENSITIVE DETECTION OF MOLECULES OR PARTICLES USING BEADS OR OTHER CAPTURE OBJECTS", by Duffy et al.; International Patent Publication No. WO2011/109364 (International Patent Application No. PCT/US2011/026645), filed Mar. 1, 2011, entitled "ULTRA-SENSITIVE DETECTION OF MOLECULES OR PARTICLES USING BEADS OR OTHER CAPTURE OBJECTS", by Duffy et al.; International Patent Publication No. WO2011/109372 (International Patent Application No. PCT/US2011/026657), filed Mar. 1, 2011, entitled "ULTRA-SENSITIVE DETECTION OF MOLECULES USING DUAL DETECTION METHODS", by Duffy et al.; U.S. Patent Application Publication No. US 2011-0212462 (Ser. No. 12/731,135), filed Mar. 24, 2010, entitled "ULTRA-SENSITIVE DETECTION OF MOLECULES USING DUAL DETECTION METHODS", by Duffy et al.; International Patent Publication No. WO2011/109379 (International Patent Application No. PCT/US2011/026665), filed Mar. 1, 2011, entitled "METHODS AND SYSTEMS FOR EXTENDING DYNAMIC RANGE IN ASSAYS FOR THE DETECTION OF MOLECULES OR PARTICLES", by Rissin et al.; U.S. Pat. No. 8,415,171 (Ser. No. 12/731,136), issued Apr. 9, 2013, entitled "METHODS AND SYSTEMS FOR EXTENDING DYNAMIC RANGE IN ASSAYS FOR THE DETECTION OF MOLECULES OR PARTICLES", by Duffy et al.; U.S. patent application Ser. No. 13/035,472, filed Feb. 25, 2011, entitled "SYSTEMS, DEVICES, AND METHODS FOR ULTRA-SENSITIVE DETECTION OF MOLECULES OR PARTICLES", by Fournier et al.; U.S. Patent Application No. US 2011-0245097 (Ser. No. 13/037,987), filed Mar. 1, 2011, entitled "METHODS AND SYSTEMS FOR EXTENDING DYNAMIC RANGE IN ASSAYS FOR THE DETECTION OF MOLECULES OR PARTICLES", by Rissin et al.; each herein incorporated by reference.

In certain embodiments, the invention involves a plurality of methods for determining detecting or measuring the concentration of DNA or RNA molecules in a sample. In certain embodiments, the DNA or RNA from the sample may be fragmented to form fragmented DNA or RNA sequences. The DNA or RNA sequences are exposed to at least a first type of binding ligand and a second type of binding ligand. The binding ligands comprise nucleic acid sequences complimentary at least a portion of a sequence contained in the target DNA or RNA. In certain embodiments, at least a portion of the fragmented DNA or RNA associates with at least one of the first type of binding ligand and/or the second type of binding ligand, wherein the first type of binding ligand comprises a first nucleic acid sequence complimentary to a first portion of a sequence contained in the DNA or RNA and second type of binding ligand comprises a second nucleic acid sequence complimentary to a second portion of a sequence contained in the DNA or RNA, wherein the first nucleic acid sequence and the second nucleic acid sequence are different. In order to detect and/or quantify the target DNA or RNA, certain embodiments involve analyzing a portion of the sample exposed to the binding ligands to determine the number of fragmented DNA or RNA sequences associated with at least one of the first type of binding ligand and the second type of binding ligand. To facilitate detection and/or quantitation of the DNA or RNA associating with the two or more types of binding ligands employed, in certain embodiments, the first type of binding ligand and the second type of binding ligand may produce substantially similar signals, e.g. electromagnetic emission signals of substantially similar wavelength.

As is apparent from the references referred to above describing exemplary single molecule array assay formats, as well as from the exemplary embodiments illustrated in the figures and described below, there are a variety of ways in which assays employing the inventive techniques may be performed. For example, in one set of embodiments, the assays are performed with the target DNA or RNA and the binding ligands free in solution. In certain such assays, hybridized complexes of the binding ligands (in the form of detection probes as used herein) and target nucleic acid molecules/fragments may be spatially partitioned and detected/quantified. Such a format is illustrated, for example, in FIG. 4 and described in more detail below. In another set of embodiments, the binding ligands (in the form of capture probes as used herein) are immobilized with respect to capture objects. In certain such assays, hybridized complexes capture probes and target nucleic acid molecules/fragments may be spatially segregated by spatially partitioning the capture objects on which they are carried, which may then be and detected/quantified. Such a format is illustrated, for example, in FIG. 1 and described in more detail below. In yet other assays, additional efficiency and sensitivity may be derived by using both binding ligands in the form of capture probes immobilized to capture objects as well as binding ligands in the form of detection probes free in solution. In certain such assays, the detection probe binding ligands may carry or associate with a signaling entity to facilitate detection/quantitation (see e.g. FIGS. 2 and 5). In some embodiments, multiple types of detection probes are used in conjunction with one or more types of capture probes, or alternatively, multiple types of capture probes are used in conjunction with one or more types of detection probes. In some cases, steps may be taken to reduce or minimize background signals related to the non-specific binding of capture probes with detection probes, which may lead to false positives.

In some embodiments, the assay involves the formation of hybridized complex(es) through capturing the target DNA or RNA on a capture object (e.g., beads such as magnetic beads, particles, etc.) via sequence-specific capture probes. Detection probes (e.g., biotinylated detection probes) may be associated with the captured DNA or RNA. The detection probes may be detected directly or indirectly. For example, in some cases, the detection probes may be labeled with an enzyme (e.g., via associating streptavidin conjugated with beta-galactosidase to the biotin). A signal can then be generated by exposing the labeled detection probes to an enzymatic substrate (e.g., converting a substrate of beta-galactosidase such as resorufin-β-D-galactopyranoside) which is converted into a product (e.g., a fluorescent product) that is detectable on single molecule arrays. The arrays can then be analyzed to detect and/or quantify the DNA or RNA in the sample. For example, the resulting signals can be reported as averaged enzymes per bead (AEB), which is associated with the number of hybridized complex on beads, thus the concentrations of target nucleic acids in solution. Single molecule assay are described in more detail herein.

In some embodiments, certain methods provided herein for determining a measure of the concentration of DNA or RNA in a sample utilize one or more sets (e.g., a plurality of sets) of binding ligands or probes which target the same DNA or RNA. The use of one or more (e.g. multiple) sets of binding ligands can aid in improving the sensitivity and/or accuracy of the concentration measurement determination.

In some cases, a set of probes, herein referred to as capture probes, is used to capture the target DNA or RNA on a solid or otherwise fluid immiscible support (capture object). Generally, the capture probes are immobilized with respect to capture objects, which can aid in the spatial separation of the target DNA or RNA. In some embodiments, a set of capture probes comprises two or more types of capture probes, wherein each type of capture probe includes a complimentary sequence to the target DNA or RNA, and each complimentary sequence for each type of capture probe is different from the other types of capture probes.

Alternatively or in addition, in some cases, a set of probes is used to detect the DNA or RNA, herein referred to as detection probes. In some embodiments, a set of detection probes comprises two or more types of detection probes, wherein each type of detection probe includes a complimentary sequence to the DNA or RNA, and each complimentary sequence for each type of detection probe is different from the other types of detection probes. The use of multiple types of capture probes and/or detection probes can provide in certain embodiments a number of advantages as compared to methods employing only a single type of capture probe and/or detection probe, as described herein.

In some embodiments, for each target nucleic acid of interest, two sets of probes are prepared, e.g., a set of capture probes and a set of detection probes. Each probe set contains multiple (e.g., 25- to 50-base) synthetic oligonucleotide sequences complementary to different sites of the target DNA or RNA. Oligonucleotide probes may be selected to be specific to the target DNA or RNA and have similar melting temperature. Each capture probe may be associated with a capture object. For example, each capture object may be modified with an amino group at 5' end and individually conjugated to carboxylated magnetic beads via a carbodiimide EDC coupling reaction. The different capture probe-conjugated capture objects can then be pooled for capturing the same target DNA or RNA molecules through hybridizing with different complementary sequences spanning the target DNA or RNA. Each capture probe can be paired with multiple detection probes that hybridize and span contiguous sequences of the target DNA or RNA that is usually downstream of the binding site of the capture probe. Each detection probe may be detected directly or indirectly. For example, each detection probe can be modified with a component which binds an enzyme, for example, each detection probe can be modified with biotin moieties at its 5' end that binds to streptavidin conjugated beta-galactosidase for signal generation. The biotinylated detection probes can be mixed at equal molar concentrations to generate a pool of detection probe for the target DNA or RNA.

According to some aspects, the target nucleic acids may be present in the context of chromosomes. Detection of such target molecules may be complicated by the secondary structures of the target itself. Prior to being captured on capture objects such as magnetic beads, the target nucleic acids may be generally fragmented into relatively shorter fragments. This may reduce the steric hindrance caused by secondary structures for better capture efficiency. During the process of breaking the target DNA or RNA into smaller fragments, there are chances that the cutting sites are within the sequences to which the capture probe and/or detection probe is complementary, thus the capture efficiency may be reduced if using only one capture probe for the target. Employing multiple types of capture and/or detection probes can minimize the negative effect due to such occurrence, by hybridizing to the intact complementary sequences at different sites at least some of which would be intact. In addition, each of several fragments derived from a single larger target molecule may be captured by using multiple capture probes with optimized selection of targeting sites, thus the overall detection efficiency could be enhanced as compared to using a single capture probe, thereby improving the detection sensitivity for the target DNA or RNA.

In some embodiments, certain methods and systems described herein may be used to detect and/or quantify multiple types of DNA or RNA molecules in a sample. In such embodiments, multiple types of capture probes and/or multiple types of detection probes may be provided for each target DNA or RNA molecule. For example, in one embodiment, a first type and a second type of DNA or RNA molecules are targeted for detection/quantification. The assay for such an embodiment may comprise a first type of capture probe, a first type of detection probe, and a second type of detection probe, each comprising a sequence complimentary to the first type of DNA or RNA molecule, and a second type of capture probe, a third type of detection probe, and a fourth type of detection probe, each comprising a sequence complimentary to the second type of DNA or RNA molecule. Those of ordinary skill in the art will be able to apply the teaching herein to assays fir detecting more than two types of DNA or RNA molecules and/or those utilizing more than one type of capture probes per type of DNA or RNA molecule and/or to assays one or more than two types of detection probes per type of DNA or RNA molecule. In certain cases, two to one hundred types, or two to twenty types, or two to ten types of DNA or RNA molecules are detected/quantified, wherein for each type of DNA or RNA, at least one set of detection probes (e.g., comprising at least a first type and a second type of detection probe) and/or at least one set of capture probes (e.g., comprising a first type and a second type of capture probe) are utilized.

Capture Probes and Capture Objects

Detection of target nucleic acids via formation of a hybridized complex on solid support such as plates, slides, or microspheres has been previously reported, where for each target DNA or RNA, one pair of probes that contains a capture probe and a detection probe/signal probe, is used hybridizing the complementary sequences of the target nucleic acids.

In certain embodiments, instead of using only one type of capture probe, multiple types of binding ligands in the form of capture probes are used for each target DNA or RNA. This can provide many benefits, including, but not limited to, improve capturing efficiency, thus enabling better sensitivity for detecting or quantifying nucleic acids. Additional advantages are described herein.

In some embodiments, a method for detecting or determining a measure of the concentration of DNA or RNA molecules in sample is provided. In some cases, the method comprises fragmenting DNA or RNA from a sample to form fragmented DNA or RNA sequences. Methods for fragmenting DNA or RNA are known in the art and are described herein. The fragmented DNA or RNA may be exposed to a number of types of capture probes (e.g., two types, three types, four types, etc.). For example, the fragmented DNA or RNA sequences may be exposed to at least a first type of capture probe comprising a first nucleic acid sequence complimentary to a portion of a sequence detection probe and a second type of capture probe comprising a second nucleic acid sequence complimentary to a portion of a sequence detection probe, wherein at least a portion of the fragmented DNA or RNA associates with the least one of the first type of capture probe or the second type of capture probe. In some embodiments, the first sequence and the second sequence are different. The first type of capture probe may be immobilized with respect to a first type of capture object and the second type of capture probe may be immobilized with respect to a second type of capture object. A portion of the sample exposed to the capture probes (and capture objects) as described above may be analyzed to determine the number of fragmented DNA or RNA sequences associated at least one of the first type of capture probe or capture object or the second type of capture probe or capture object. The first type of capture probe and/or capture object and the second type of capture probe and/or capture object may produce substantially similar signals. Alternatively, the first type of capture probe and/or capture object and the second type of capture probe and/or capture object may produce different signals, as described herein.

A non-limiting example of a method comprising multiple types of capture objects is depicted in FIG. 1. A sample comprising a plurality of DNA or RNA molecule is provided. For simplicity, step A depicts only a single DNA or RNA molecule, 50. The DNA or RNA molecule is fragmented, for example, into first fragment 52 and second fragment 54 (step B). The DNA or RNA fragments (e.g., 52 and 54) are then exposed to a plurality of binding ligands in the form of capture probes, 56, comprising first type of capture probe 58 and second type of capture probe 60, wherein first type of capture probe 58 comprises a sequence which is complimentary to a sequence of first fragment 52 and second type of capture probe 60 comprises a sequence which is complimentary to a sequence of second fragment 54. First fragment 52 associate with a first type of capture probe and second fragment 54 associates with second type of capture probe (e.g., see step C). The capture probes may be associated with a capture object (e.g., bead 62) as shown in step B and C. The sample may then be analyzed to determine quantify the DNA or RNA molecules in the fluid sample, as described in more detail herein.

It should be understood that while some of the embodiments described herein employ multiple types of capture probes/objects which target a single type of DNA or RNA molecule, in some embodiments, only single type of capture probe/object for each type of DNA or RNA molecule is employed. For example, in some cases, for a single type of DNA or RNA molecule, only a single type of capture probe/object and multiple types of detection probe binding ligands are utilized.

In embodiments where more than two types of capture probes are employed, the third and following capture probes may each contain a nucleic acid sequence complimentary to a different portion of a sequence detection probe, and the sequences of each of the third and following capture probes may be different than every other sequence contained in a different type of capture probe. In some embodiments, three types of capture probes are employed, wherein the first type of capture probe comprises a first nucleic acid sequence complimentary to a portion of a sequence detection probe, the second type of capture probe comprises a second nucleic acid sequence complimentary to a different portion of a sequence detection probe, and the third type of capture probe comprises a third nucleic acid sequence complimentary to a different portion of a sequence detection probe. In some embodiments, the first sequence, the second sequence, and the third sequence differ from each other. In some cases, a fourth type of capture probe is also employed comprising a fourth nucleic acid sequence complimentary to a different portion of a sequence detection probe. In some cases, the fourth sequence differs from the first sequence, the second sequence, and the third sequence. Those of ordinary skill in the art will be able to apply these teaches to embodiments where more than four types of capture probes are employed, for example, fix types, six types, seven types, eight types, etc. Each capture probe may be associated with a capture object, as described herein.

Figure 2A:
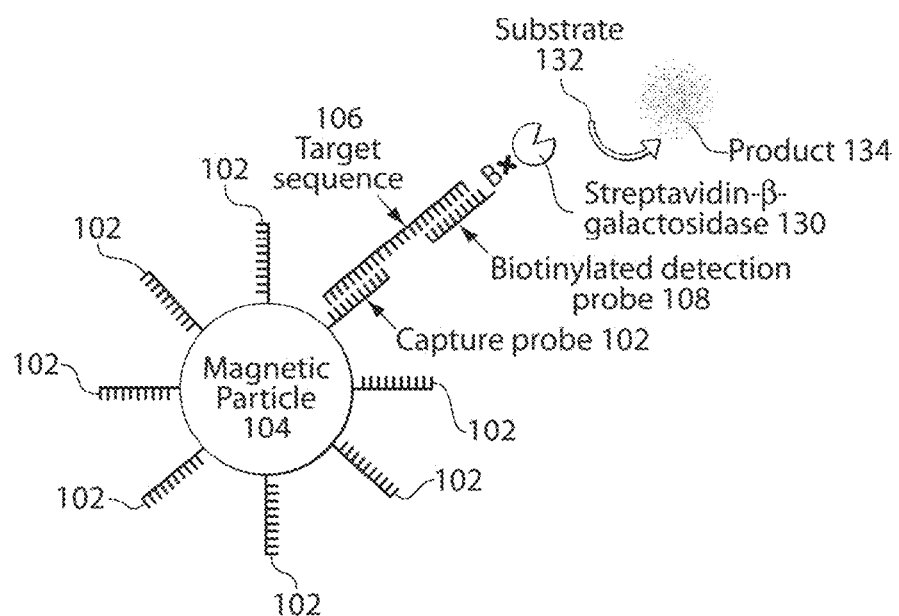
FIG. 2 depicts A) a convention approach to single molecule arrays DNA assay using a single capture probe and B) an approach according to an exemplary embodiment of the present invention using multiple types of capture probes on separate beads to capture different fragments from the same DNA molecule.
Figure 2B:
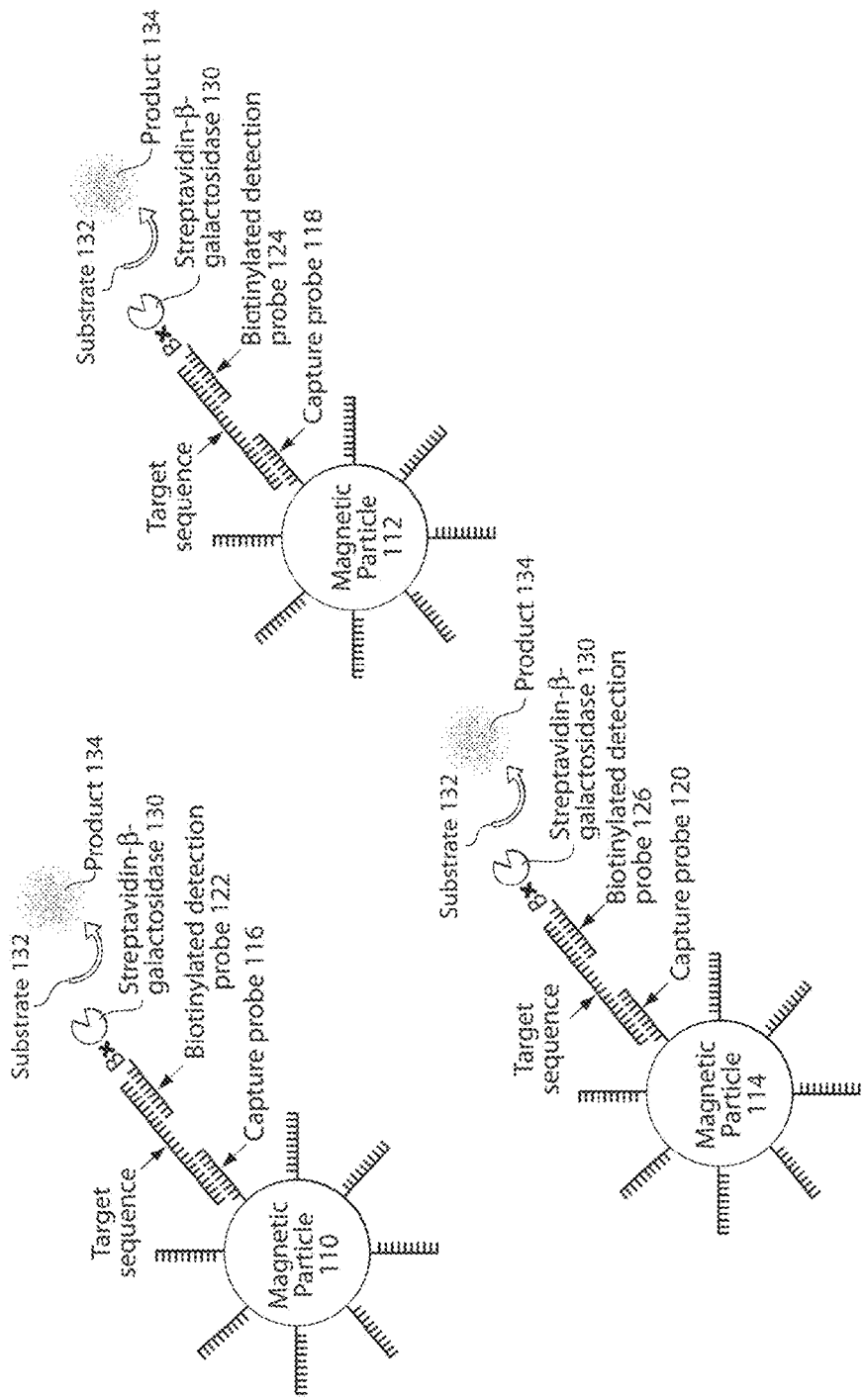
Figures 1, 4:
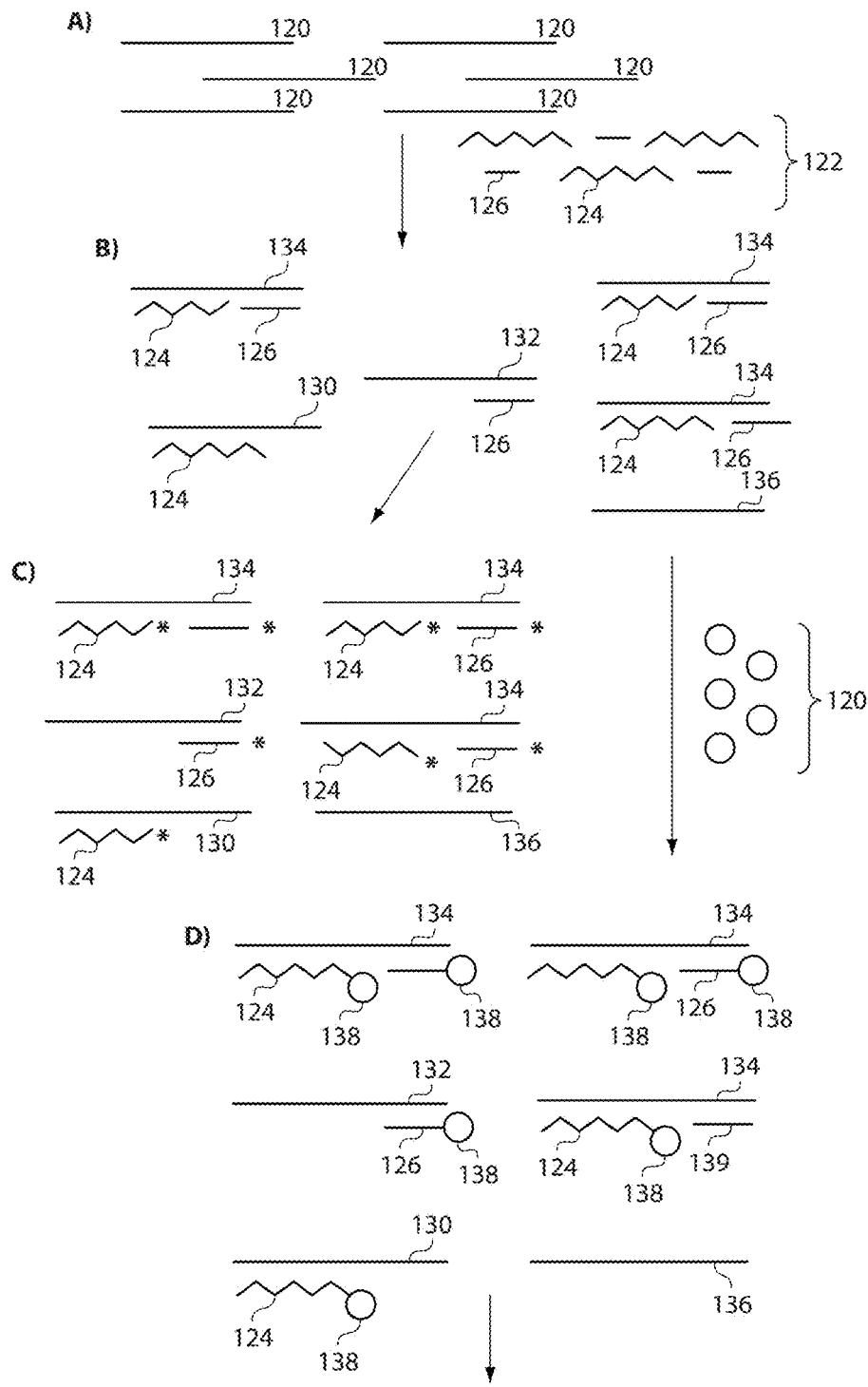
FIG. 4 depicts a non-limiting example of a method utilizing a plurality of types of detection probes, according to some embodiments.
Figures 2, 4:
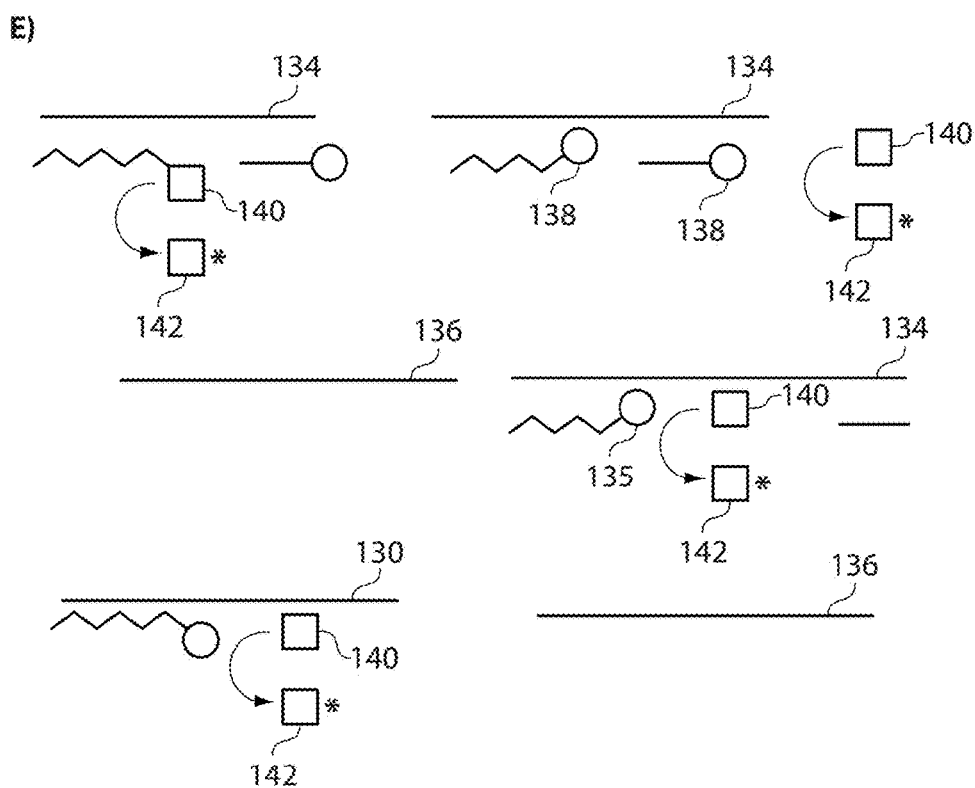

As yet another example, FIG. 2 shows a schematic of A) a prior art method and B) a method according an embodiment of the invention employing both capture probe binding ligands and detection probe binding ligands (described in more detail below. FIG. 2A depicts plurality of capture probes 102 which are immobilized with respect to single capture object 104 which is utilized in an assay for detecting a single fragment of a DNA or RNA molecule (e.g., 106) and wherein a single type of detection probe 108 is employed. In contrast, in FIG. 2B, three types of capture objects are employed (e.g., 110, 112, and 114). Each type of capture object comprises a different capture probe (e.g., 116, 118, and 120), wherein each type of capture probe comprises a sequence which is complimentary to a particular portion of the fragmented DNA or RNA. In this Figure, three different types of detection probes (e.g., 122, 124, and 126) are also employed, each comprising a sequence which is complimentary to a particular fragment of the fragmented DNA or RNA. FIG. 3 gives an illustrative sequence design used to detect a gene from *S. aureus* using this approach. Those of ordinary skill in the art will understand that any other number of detections probes may be used, for example, one type, two types, four types, etc., as described herein. In this embodiment, the detection probes are exposed to and associated with an enzyme (e.g., streptavidin-β-galactosidase, 130), and the same is then exposed to an enzymatic substrate (e.g., 132) which produces a detectable product (e.g., 134), as described in more detail herein.

Those of ordinary skill in the art will be able to prepare and select appropriate capture probes to be used in connection with the methods described herein. The capture probes generally comprise synthetic oligonucleotide sequences complementary to different sites of the target DNA or RNA. In some cases, each type of capture probe is selected to have a synthetic oligonucleotide sequences complementary to a particular fragment of the target DNA or RNA, wherein the target DNA or RNA is fragmented prior to exposure to the capture probes. In some cases, the oligonucleotide probes may be selected to be specific to the target DNA or RNA and have similar melting temperature. The capture probes may be of any suitable length, for example, 25-50 bases may be typical, although capture probe lengths could be as short as 5 bases (e.g., limited, in part, due to by binding affinity) or as long as 100 bases (e.g., limited, in part, due to the formation of competing secondary structures).

In some embodiments, each capture probe is associated with a capture object. The capture objects may be configured to be able to be spatially segregated from each other, that is, the capture objects may be provided in a form such that the capture objects are capable of being spatially separated into a plurality of locations. For example, the plurality of capture objects may comprise a plurality of beads (which can be of any shape, e.g., sphere-like, disks, rings, cube-like, etc.), a dispersion or suspension of particulates (e.g., a plurality of particles in suspension in a fluid), nanotubes, particles, or the like. In some embodiments, the plurality of capture objects is insoluble or substantially insoluble in the solvent(s) or solution(s) utilized in the assay. In some cases, the capture objects are solid or substantially solid (e.g., is essentially free of pores), however, in some cases, the plurality of capture objects may be porous or substantially porous, hollow, partially hollow, etc. The plurality of capture objects may be non-absorbent, substantially non-absorbent, substantially absorbent, or absorbent. In some cases, the capture objects may comprise a magnetic material, which as described herein, may facilitate certain aspect of the assay (e.g., washing step). In some cases, a capture object surface may also comprise a protective or passivating layer that can reduce or minimize non-specific binding events (e.g., analyte molecules, detection probes, enzyme conjugate, etc.). The capture object may also comprise a liposome or other similar article.

Those of ordinary skill in the art will be aware of methods and systems for associating a capture probe with a capture object. The portion of the capture object which comprises a plurality of capture probes may be selected or configured based upon the physical shape/characteristics and properties of the capture objects (e.g., size, shape), and the format of the assay. In some embodiments, substantially all of the outer surfaces of the capture objects comprise a plurality of capture probes. In some cases, the capture probes are associated with a capture object (e.g., become immobilized with respect to) via formation of at least one chemical bond and/or physical adsorption, or combination thereof. Non-limiting examples of types of chemical bonds include ionic bonds, covalent bonds (e.g., carbon-carbon, carbon-oxygen, oxygen-silicon, sulfur-sulfur, phosphorus-nitrogen, carbon-nitrogen, metal-oxygen, or other covalent bonds), hydrogen bonds (e.g., between hydroxyl, amine, carboxyl, thiol, and/or similar functional groups), dative bonds (e.g., complexation or chelation between metal ions and monodentate or multidentate ligands), Van der Waals interactions, or the like.

The plurality of capture objects (e.g., beads) for DNA or RNA capture may be of any suitable size or shape. Non-limiting examples of suitable shapes include spheres, cubes, ellipsoids, tubes, sheets, and the like. In certain embodiments, the average diameter (if substantially spherical) or average maximum cross-sectional dimension (for other shapes) of a capture object may be greater than about 0.1 um (micrometer), greater than about 1 um, greater than about 10 um, greater than about 100 um, greater than about 1 mm, or the like. In other embodiments, the average diameter of a capture object or the maximum dimension of a capture object in one dimension may be between about 0.1 um and about 100 um, between about 1 um and about 100 um, between about 10 um and about 100 um, between about 0.1 um and about 1 mm, between about 1 um and about 10 mm, between about 0.1 um and about 10 um, or the like. The "average diameter" or "average maximum cross-sectional dimension" of a plurality of capture objects, as used herein, is the arithmetic average of the diameters/maximum cross-sectional dimensions of the capture objects. Those of ordinary skill in the art will be able to determine the average diameter/maximum cross-sectional dimension of a population of capture objects, for example, using laser light scattering, microscopy, sieve analysis, or other known techniques. For example, in some cases, a Coulter counter may be used to determine the average diameter of a plurality of beads.

The capture objects for DNA or RNA capture may be fabricated from one or more suitable materials, for example, plastics or synthetic polymers (e.g., polyethylene, polypropylene, polystyrene, polyamide, polyurethane, phenolic polymers, or nitrocellulose etc.), naturally derived polymers (latex rubber, polysaccharides, polypeptides, etc.), composite materials, ceramics, silica or silica-based materials, carbon, metals or metal compounds (e.g., comprising gold, silver, steel, aluminum, copper, etc.), inorganic glasses, silica, and a variety of other suitable materials. Non-limiting examples of potentially suitable configurations include beads (e.g., magnetic beads), tubes (e.g., nanotubes), plates, disks, dipsticks, or the like.

In some cases, the capture objects may be selected such that the capture object itself is detectable by the system. This may be useful in embodiments where the fraction or percentage of capture objects associated with an DNA or RNA molecules or fragment is to be determined (e.g., when the total number of capture objects interrogated and detected is used to determine the fraction of capture objects associated with an DNA or RNA molecules or fragment). For example, a capture object may be characterized as having an emission or absorption spectrum that can be exploited for detection so that capture objects may be interrogated to determine which spatial location contains a capture object. The properties of the emission spectrum (e.g., wavelength(s), intensity, etc.), may be selected such that the emission produced by the capture objects does not substantially alter and/or interfere with any other emission from components used in the assay (e.g., the emission of any labels used to determine the presence or absence of an DNA or RNA molecule or fragment). In some cases, dye molecules may be associated with a capture object using the capture probes present on the surface of the capture object (e.g., a dye molecule may associate via a bond or interaction with a capture probe). In some cases, between about 1 and about 50,000, or between about 1000 and about 50.000, or between about 1000 and about 20.000, or between about 10,000 and about 20,000, or between about 1,000 and about 10,000, or between about 10,000 and about 30,000, or between about 1 and about 10,000 dye molecules (e.g., fluorescent dye molecules) are associated with each capture object. In some cases, dye molecules might first be associated with the capture object, before the capture probes are attached to the capture object. This approach reduces the chances that the affinity of the capture probes is reduced by attachment of dye molecules. In some cases, dye molecules are attached to an inert, "blocking" protein (e.g., bovine serum albumin) and the dye-labeled inert protein is used to block the beads after capture probes are attached to the capture object. It should be understood, that in some cases, the capture objects may be detected and quantified using white light (e.g., as described herein, for example using bright field, dark field and/or phase contrast imaging).

In some embodiments, each of the plurality of types of capture object to be associated with a single type of DNA or RNA molecule or DNA or RNA fragments from a single DNA or RNA may be detectable using substantially similar techniques and/or emit substantially similar signals. In some embodiments, the signals are indistinguishable. For example, the signal from a first type of capture object comprising a first type of capture probe (e.g., comprising a first nucleic acid sequence complimentary to a portion of a sequence detection probe) and a second type of capture object comprising a second type of capture probe (e.g., comprising a second nucleic acid sequence complimentary to a portion of a sequence detection probe) may be indistinguishable. In embodiments where two or more types of DNA or RNA molecules are to be detected, the types of capture objects comprising capture probes complimentary to each type of DNA or RNA molecule may produce substantially similar signals. For example, a first type of capture object and a second type of capture object may be provided to capture a first type of DNA or RNA molecule wherein the first type of capture object and the second type of capture object produce substantially similar signals, and a third type of capture object and a fourth type of capture object may be provided to capture a second type of DNA or RNA molecule wherein the third type of capture object and the fourth type of capture object produce substantially similar signals. The signals may be produce via association with or incorporation into the capture object of a dye or other detectable entity, as described in more detail herein.

In some embodiments, at least some of the target DNA or RNA molecules or fragments will be captured by a capture probe and become immobilized with respect to a capture object (e.g., bead). In some cases, the target DNA or RNA molecules or fragments are provided in a manner (e.g., at a concentration) such that a statistically significant fraction of the beads associate with a single target DNA or RNA molecule or fragment and a statistically significant fraction of the beads do not associate with any DNA or RNA molecules or fragments. At least some of the plurality of beads (e.g., those associated with a single DNA or RNA molecule or fragment or not associated with any DNA or RNA molecules or fragments) may then be spatially separated/segregated into a plurality of assay sites (e.g., of an assay consumable). The assay sites may optionally be exposed to a variety of reagents and/or washed. Alternatively, the plurality of capture objects may be exposed to reagents (e.g., DNA or RNA molecules or fragments, detection probes, etc.), followed by washing of the capture objects prior to spatially separation/segregation. At least some of the assay sites may then be addressed to determine the number of assay sites containing a DNA or RNA molecule or fragment. In some cases, the number of assay sites containing a bead not associated with a DNA or RNA molecule or fragment, the number of assay sites not containing a bead, and/or the total number of assay sites addressed may also be determined. Such determination(s) may then be used to determine a measure of the concentration of DNA or RNA molecules in the fluid sample. In some cases, more than one DNA or RNA molecule or fragment may associate with a bead and/or more than one bead may be present in an assay site. In some cases, the plurality DNA or RNA molecules or fragments may be exposed to at least one additional reaction component prior to, concurrent with, and/or following spatially separating at least some of the DNA or RNA molecules or fragments into a plurality of locations.

In some embodiments, the methods and systems described in International Patent Publication No. WO2011/109364 (International Patent Application No. PCT/US2011/026645), filed Mar. 1, 2011, entitled "ULTRA-SENSITIVE DETECTION OF MOLECULES OR PARTICLES USING BEADS OR OTHER CAPTURE OBJECTS", by Duffy et al., herein incorporated by reference may be adapted and used for detection and quantitation in certain embodiments of the presently described methods. In some cases, the exposing step comprises spatially segregating at least a portion of the DNA or RNA fragments into a plurality of separate locations. In some cases, the exposing comprises immobilizing the DNA or RNA fragments with respect to a plurality of capture objects such that at least some of the capture objects associate with at least one DNA or RNA fragments and a statistically significant fraction of the capture objects do not associate with any DNA or RNA fragments; and spatially segregating at least a portion of the capture objects subjected to the immobilizing step into a plurality of separate locations. In some cases, in an analyzing step, the number of locations containing a capture object that includes a detection probe is determined. In some cases, the plurality of locations comprises a plurality of reaction vessels. In some cases, the average volume of the plurality of reaction vessels is between about 10 attoliters and about 100 picoliters, or between about 1 femtoliter and about 1 picoliter. In some embodiments, between about 1,000 and about 1,000,000 locations are employed. Additional details and variations are described herein.

There are a number of benefits of using multiple types of capture probes for each target DNA or RNA molecule, particularly when the target is present in chromosomal DNA or RNA where fragmentation of the target may be necessary prior to detection. For example, in some cases, for target nucleic acids that are of great length, the presence of inherent secondary structures might create steric hindrance that blocks the availability of the binding sites to certain capture probes and can adversely affect the hybridization for the target to be captured. The risk of such events can be reduced by using multiple capture probes that hybridize to different binding sites on the target, thus the capture efficiency of the target can be improved. As another example, when target fragmentation is utilized to obtain smaller fragments, especially via random sonication, for more efficient hybridization, there are chances that the cutting sites are within the sequences to which a given capture probe is complementary to, thus reducing the capture efficiency of the target. Employing multiple capture probes can minimize the negative effect due to such occurrence, by providing the ability of multiple capture probes to hybridize to the intact complementary sequences at different sites instead. As yet another example, multiple capture probes can be selected that are complementary to the sequences at different locations along the target such that each or multiple fragments generated either via enzymatic digestion or random sonication can be all captured. In this way, one target molecule can become multiple molecules that can be detected, thus increasing the concentration of the detectable target.

Detection Probes

In certain embodiments of the inventive assays, binding ligands in the form of detection probes are used to facilitate signal generation, in addition to or as an alternative to using capture probes or multiple types of capture probes as described above. In certain such embodiments, for each captured target DNA or RNA, multiple detection probes (e.g., biotinylated detection probes) are used instead of using only one detection probe. This may also, particularly in combination with the use of multiple capture probes, further improve the overall detection efficiency, and thus achieve better sensitivity for detecting or quantifying nucleic acids. Other advantages are described herein.

Fragmented DNA or RNA in target samples may in certain embodiments of the assay methods described may be exposed to a number of types of detection probes (e.g., two types, three types, four types, etc.). For example, the fragmented DNA or RNA sequences may be exposed to at least a first type of detection probe and a second type of detection probe, wherein at least a portion of the fragmented DNA or RNA associates with at least one of the first type of detection probe and/or the second type of detection probe. The first type of detection probe may comprise a first nucleic acid sequence complimentary to a first portion of a sequence detection probe molecule or fragment and second type of detection probe may comprise a second nucleic acid sequence complimentary to a second portion of a sequence detection probe molecule or fragment. In some embodiments, the first nucleic acid sequence and the second nucleic acid sequence are different. The exposing may occur following exposure and/or immobilization with respect to one or more types of capture probes (e.g., associated with a capture object), as described herein. A portion of the sample exposed to the detections probes may be analyzed to determine the number of fragmented DNA or RNA sequences associated at least one of the first type of detection probe or the second type of detection probe, wherein the first type of detection probe and the second type of detection probe produce substantially similar signals. In some embodiments, the signal detected from the first type of detection probe and signal detected from the second type of detection probe are indistinguishable. Alternatively, the first type of detection probe and the second type of detection probe may produce different signals.

In embodiments where more than two types of detection probes are employed, the third and subsequent detection probes may each contain a nucleic acid sequence complimentary to a different portion of a sequence contained in the target DNA or RNA. The sequences of each of the third and subsequent detection probes may be different than every other sequence contained in a different type of detection probe. In some embodiments, three types of detection probes are employed, wherein the first type of detection probe comprises a first nucleic acid sequence complimentary to a portion of a sequence detection probe, the second type of detection probe comprises a second nucleic acid sequence complimentary to a portion of a sequence detection probe, and the third type of detection probe comprises a third nucleic acid sequence complimentary to a portion of a sequence detection probe. In some embodiments, the first sequence, the second sequence, and the third sequence differ from each other. In some cases, a fourth type of detection probe is also employed comprising a fourth nucleic acid sequence complimentary to a portion of a sequence detection probe. In some cases, the fourth sequence differs from the first sequence, the second sequence, and the third sequence. Those of ordinary skill in the art will be able to apply these teaches to embodiments where more than four types of detection probe are employed, for example, fix types, six types, seven types, eight types, etc. In some cases, two types of detection probes are employed, each comprising a sequence complimentary to a portion of a sequence detection probe. In some cases, three types of detection probes are employed, each comprising a sequence complimentary to a portion of a sequence detection probe molecules or fragments. In some cases, four types of detection probes are employed, each comprising a sequence complimentary to a portion of a sequence detection probe. In some cases, five types of detection probes are employed, each comprising a sequence complimentary to a portion of a sequence detection probe. In some cases, two to ten, or two to seven, or two to five types, or three to ten, or three to seven, or three to five types of detection probes are employed, each comprising a sequence complimentary to a portion of a sequence detection probe. In some embodiments, the signal detected from each type of detection probe is substantially similar. In general, in embodiments in which the signal detected from multiple types of signaling binding ligands (e.g. detection probes and/or certain capture probes/objects) is substantially similar, each type of binding ligand produces signals comprising emission of electromagnetic energy differing in wavelength from other types of binding ligands by not more than 50 nm, optionally by not more than 40 nm, optionally by not more than 30 nm, optionally by not more than 20 nm, optionally by not more than 10 nm, optionally by not more than 5 nm, and optionally by not more than 1 nm. In some cases, the signal detected from each type of detection probe is indistinguishable.

A non-limiting example of a method comprising multiple types of detection probes is depicted in FIG. 4. In the illustrated embodiment, the assay is performed in solution without target capture by capture probes carried by capture objects. In alternative embodiments described below, both capture probes/objects and detection probes may be employed together to further enhance efficiency and/or sensitivity. A sample comprising a plurality of DNA or RNA molecules or fragments 120 is provided, as depicted in step A. Generally, DNA or RNA molecule is fragmented prior to the method and a plurality of DNA or RNA fragments 120 are provided. The DNA or RNA molecules or fragments are exposed to plurality of types of detection probes 122, as shown in step B. In this cases, plurality of types of detection probes 122 comprise first type of detection probe 124 and second type of detection probe 126. The DNA or RNA molecules or fragments are exposed to plurality of detection probes 122 under conditions so that, on average, at least one of the first type of detection probe or at least one of the second type of detection probe associates with each DNA or RNA molecule or fragment. For example, as shown in step B, some of the DNA or RNA molecules or fragments associate with only the first type of detection probe (e.g., 130), some of the DNA or RNA molecules or fragments associate with only the second type of detection probe (e.g., 132), and some of the DNA or RNA molecules associate with both the first type and the second type of detection probes (e.g., 134). In some cases, some of the DNA or RNA molecules or fragments might not associate with any detection probes (e.g., 136 in step B). The sample may then be analyzed to determine the presence or absence of the detection probes (e.g., following spatial separation of the DNA or RNA molecules or fragments into a plurality of locations, as described herein). The detection probes may be detected directly, as shown in step C, wherein each of the detection probes emits a detectable single (e.g., as indicated by the stars). Alternatively, the detection probes may be detected indirectly. For example, the sample may be exposed to a plurality of secondary binding ligands (e.g., 138), wherein at least some of the detection probes (e.g., associated with a DNA or RNA molecule or fragment) associate with a secondary binding ligand (e.g., see step D). In some cases, all or substantially all of the detection probes associate with a secondary binding ligand. In some cases, however, a portion of the detection probes do not associate with any secondary binding ligands (e.g., see detection probe 139 in step D). The secondary binding ligands may be detected directly, wherein each of the secondary binding ligands emits a detectable signal. Alternatively, as shown in step E, the secondary binding ligands may be detected indirectly, wherein the sample is exposed to a precursor labeling agent (e.g., 140) which is converted to a labeling agent (e.g., 142) upon exposure to a secondary binding ligand.

As noted above, the detection probes may be detected directly or indirectly. In the case of direct detection, a detection probe comprises a molecule or moiety that may be directly interrogated and/or detected (e.g., a fluorescent entity, nanoparticle, etc.). If a first non-limiting case of indirect detection, a detection probe may comprise a converting agent which can convert a precursor labeling agent into a labeling agent, wherein the labeling agent is detectable. In another non-limiting case of indirect detection, a secondary binding ligand is used for determining the presence of the detection probe, wherein the secondary binding ligand associates with the detection probe. The secondary binding ligand may be detected either directly or indirectly. For example, the secondary binding ligand may be detected directly when it comprises at least one molecule or moiety that can be directly interrogate and/or detected (e.g., the secondary binding ligand comprises a detectable molecule or moiety such as a fluorescent entity, nanoparticle, etc.). In the case of indirect detection, the secondary binding ligand may comprise a converting agent (e.g., an enzymatic component) that can convert a precursor labeling agent into a labeling agent (e.g., an agent that is detected in an assay). A "precursor labeling agent" is any molecule, particle, or the like, that can be converted to a labeling agent upon exposure to a suitable converting agent (e.g., an enzymatic component). A "labeling agent" is any molecule, particle, or the like, that facilitates detection, by acting as the detected entity, using a chosen detection technique. A measure of the concentration of DNA or RNA molecule or fragment in the fluid sample may be determined based at least in part by determining the number of locations containing a labeling agent (e.g., by relating the number of locations containing a labeling agent to the number of locations containing a DNA or RNA molecule or fragment (or number of capture objects associated with at least one DNA or RNA molecule or fragment to total number of capture objects for assays that employ capture objects and probes as described above to facilitate target capture, partitioning, and/or detection and quantitation)). In some embodiments, the secondary binding ligand comprises an enzymatic component, wherein the enzymatic component converts a precursor labeling agent (e.g., enzymatic substrate) to a labeling agent (e.g., fluorescent product).

In some embodiments, each type of detection probe comprises a moiety which can bind a secondary binding ligand. In some cases, each detection probe comprises only a single moiety which can bind a secondary binding ligand. For example, each detection probe may comprise a single biotin moiety, wherein the biotin moiety can be associated with an secondary binding ligand comprising a moiety which binds biotin (e.g., streptavidin) and an enzymatic component. The secondary binding ligand may then be detected via exposure to a precursor labeling agent (e.g., enzymatic substrate) which is converted into a labeling agent.

In some cases, the inventors have found that using multiple detection probes that each include only a single moiety which can bind an secondary binding ligand on each detection probe improves the sensitivity of the assay over using a single detection probe comprising multiple moieties, but having the same total number of moieties. Without wishing to be bound by theory, this may be due to maximizing the opportunity for the binding of the secondary binding ligand to the moiety by spatially separating the moieties without having secondary structures of using one, larger detection probe. In some embodiments, the method employs a small number of type of detection probes (e.g., 2-10, or 2-7, or 2-5, or 3-10, or 3-7, or 3-5 types of detection probes), wherein each detection probe comprises only a single moiety which can bind a secondary binding ligand. In certain embodiments, the method employs 2-10, or 2-7, or 2-5, or 3-10, or 3-7, or 3-5 types of detection probes, wherein each detection probe comprises a single biotin moiety.

In some embodiments, the secondary binding ligand comprises an enzymatic component (e.g., horseradish peroxidase, beta-galactosidase, alkaline phosphatase, etc.), wherein the secondary binding ligand associates with at least some of the detection probes. A precursor labeling agent may then be provided, wherein the precursor labeling agent is converted to a labeling agent upon exposure to the enzymatic component. In a particular embodiment, each type of detection probe comprises biotin. The detection probe may be detected by first exposing it to a secondary binding ligand comprising streptavidin and an enzymatic component, following by exposure to a precursor labeling agent which is converted to a labeling agent upon exposure to the enzymatic component.

Figure 5A:
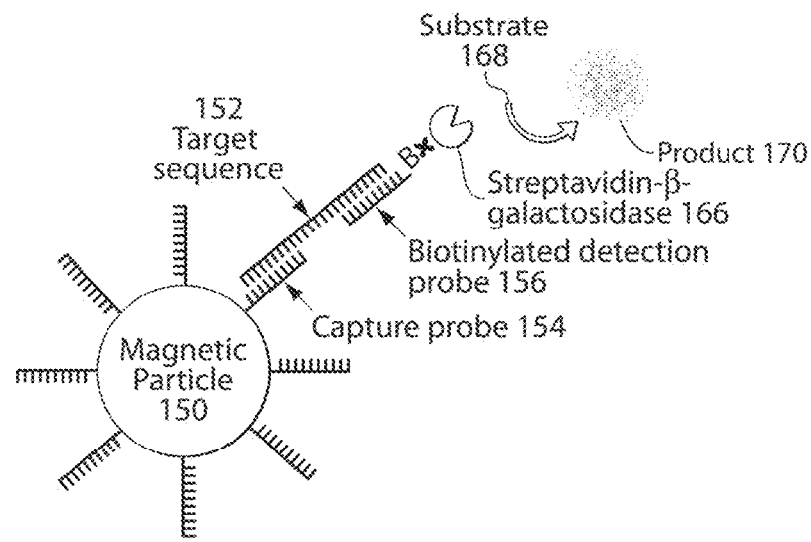
FIG. 5 depicts A) a convention approach using a single biotinylated probe to form a "sandwich" and B) an approach according to an exemplary embodiment of the present invention using multiple types of biotinylated detection probes to form the sandwich.
Figure 5B:
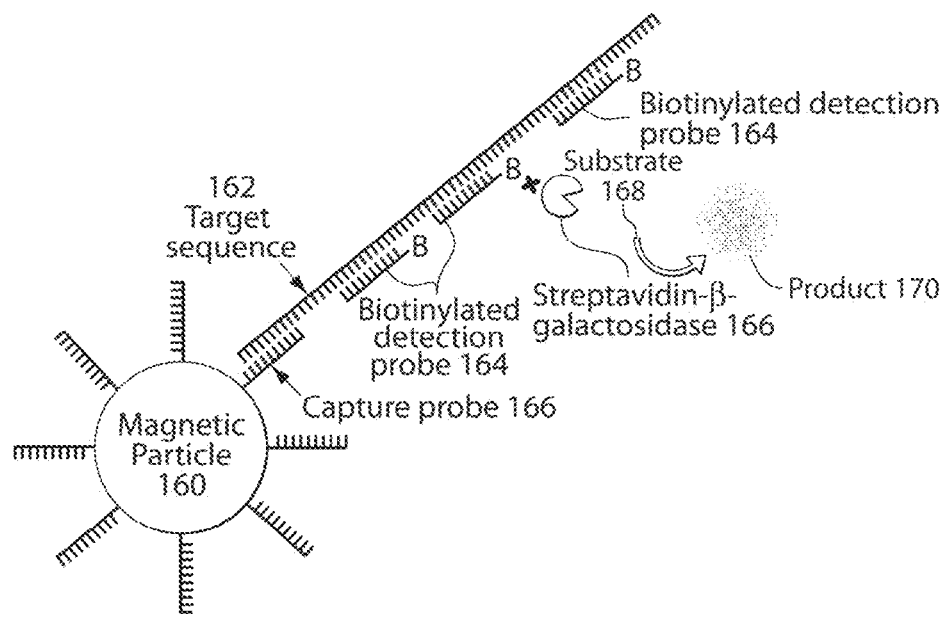
Figure 6:
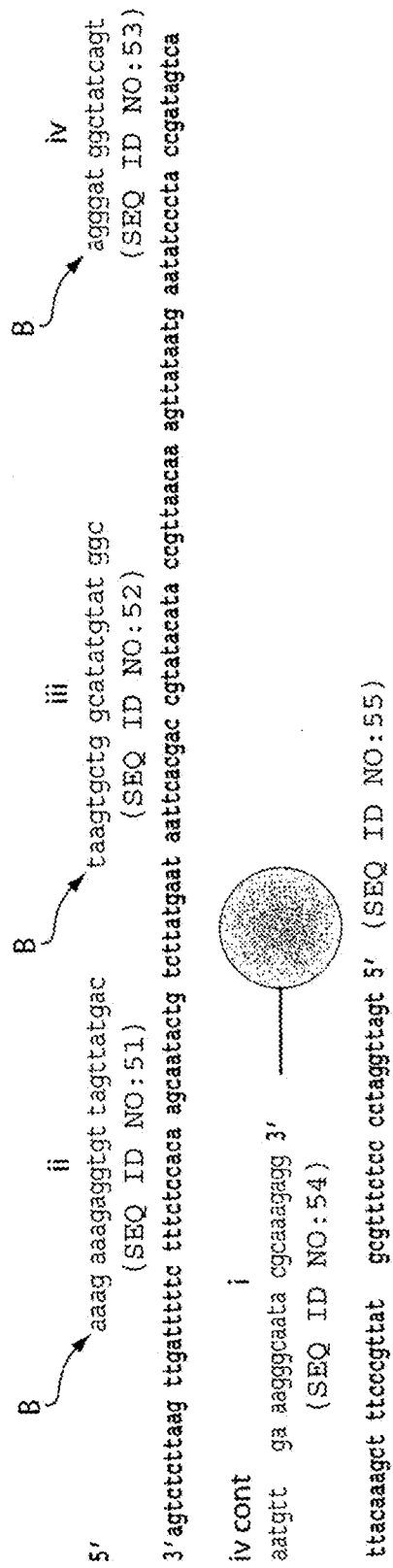
FIG. 6 depicts an exemplary sequence design for detecting a target fragment of a gene (black sequence) using a single capture probe (sequence i) attached to a bead and multiple biotinylated detection probes (sequences ii, iii, and iv) according to some embodiments.

Another non-limiting example of a method is shown in FIG. 5 utilizing both capture probes and objects as well as detection probes, wherein FIG. 5 shows a schematic of A) a prior art method utilizing only a single type of detection probes (i.e. capture and detection sequence) and B) a method according to an embodiment of the present invention using a plurality of types of detection probe (and optionally also a variety of types of capture probe—not illustrated). FIG. 5A depicts a single detection probe being employed for a single fragment of the DNA or RNA molecules. In contrast, in FIG. 5B, three types of detection probes are employed, each comprising a sequence which is complimentary to a particular sequence of the fragmented DNA or RNA. The detection probes may be detected directly or indirectly, as described in more detail herein. In FIG. 5, the detection probes are detected indirectly, in that the detection probes are exposed to and associated with an enzyme (e.g., streptavidin-β-galactosidase, 166), and the same is then exposed to an enzymatic substrate (e.g., 168) which produces a detectable product (e.g., 170). FIG. 6 gives an illustrative sequence design used to detect a gene fragment of S. aureus using this approach.

Those of ordinary skill in the art will be able to prepare and select appropriate detection probes to be used in connection with the methods described herein. The detection probes generally comprise a synthetic oligonucleotide sequences complementary to different sites of the target DNA or RNA. In some cases, each type of detection probe is selected to have a synthetic oligonucleotide sequences complementary to a particular fragment of the target DNA or RNA, wherein the target DNA or RNA is fragmented prior to exposure to the detection probes. In some cases, the oligonucleotide probes may be selected to be specific to the target DNA or RNA and have similar melting temperature. The capture probes may be of any suitable length, for example, 18-30 bases may be typical, although detection probe lengths could be as short as 5 bases (e.g., limited, in part, by binding affinity) or as long as 100 bases (e.g., limited, in part, by the formation of competing secondary structures).

The assay methods and systems may employ a variety of different components, steps, and/or other aspects that will be known and understood by those of ordinary skill in the art. For example, a method may further comprise determining at least one background signal determination (e.g., and further comprising subtracting the background signal from other determinations), wash steps, and the like. In some cases, the assays or systems may include the use of at least one detection probe, as described herein. In some cases, the measure of the concentration of DNA or RNA molecules in a fluid sample is based at least in part on comparison of a measured parameter to a calibration curve.

In certain embodiments, solubilized, or suspended precursor labeling agents may be employed, wherein the precursor labeling agents are converted to labeling agents which are insoluble in the liquid and/or which become immobilized within/near the location (e.g., within the reaction vessel in which the labeling agent is formed). Such precursor labeling agents and labeling agents and their use are described in commonly owned U.S. Patent Application Publication No. US-2010-0075862 (Ser. No. 12/236,484), filed Sep. 23, 2008, entitled "HIGH SENSITIVITY DETERMINATION OF THE CONCENTRATION OF ANALYTE MOLECULES OR PARTICLES IN A FLUID SAMPLE", by Duffy et al., incorporated herein by reference.

In some embodiments, the methods may be carried out using the methods and systems described in International Patent Publication No. WO2011/109364 (International Patent Application No. PCT/US2011/026645), filed Mar. 1, 2011, entitled "ULTRA-SENSITIVE DETECTION OF MOLECULES OR PARTICLES USING BEADS OR OTHER CAPTURE OBJECTS", by Duffy et al., herein incorporated by reference. In some cases, the exposing step comprises spatially segregating at least a portion of the DNA or RNA fragments into a plurality of separate locations. In some cases, the exposing comprises immobilizing the DNA or RNA fragments with respect to a plurality of capture objects such that at least some of the capture objects associate with at least one DNA or RNA fragments and a statistically significant fraction of the capture objects do not associate with any DNA or RNA fragments; and spatially segregating at least a portion of the capture objects subjected to the immobilizing step into a plurality of separate locations. In some cases, in the analyzing step, the number of said locations containing a capture object that includes a detection probe is determined. In some cases, the plurality of locations comprises a plurality of reaction vessels. In some cases, the average volume of the plurality of reaction vessels is between about 10 attoliters and about 100 picoliters, or between about 1 femtoliter and about 1 picoliter. In some embodiments, between about 1,000 and about 1,000,000 locations are employed. Additional details and variations are described herein.

There are many benefits to using multiple types of detection probes for each RNA/DNA (e.g., using single molecule array nucleic acid assays). For example, the detection efficiency of fragmented target DNA or RNA may be improved. Target nucleic acids with greater length may be digested into smaller fragments prior to detection, either with random sonication or enzymatic digestion, to reduce steric hindrance that could affect hybridization efficiency. Furthermore, for assays using both capture probes and detection probes, during fragmentation of the target DNA or RNA, the binding sites complementary to the capture and detection probes could be possibly separated into two fragments, which may prevent the formation of the hybridized complex via cooperative hybridization when using a single detection probe for the captured target DNA or RNA. As a result, the captured target nucleic acids may not be detected. Having more detection probes available for each capture probe can minimize the occurrence of such events, and enable the captured target to be detected at higher efficiency to improve the overall detection sensitivity. As another example, the enzymatic labeling efficiency of the hybridized complex on beads may be enhanced. The detection efficiency of hybridized complexes formed on beads is determined in part by the extent of those complexes that could be bound by streptavidin conjugated beta-galactosidase via the biotin-streptavidin interaction. It has been demonstrated previously that increasing the number of biotins conjugated to the detection antibody in a single molecule array protein assay can improve the detection efficiency of the sandwiched immunocomplex on beads. Usually, a detection antibody with 6 to 10 biotins gives the best signal-to-noise ratio, thus leading to the improved sensitivity for protein detection. Similarly, using multiple detection oligonucleotide probes, compared to only one detection probe, for each captured target DNA or RNA on beads can introduce more biotins on the hybridized complex, which can in turn facilitate the complex to be bound by streptavidin conjugated beta-galactosidase, thus improve the overall detection efficiency of the target DNA or RNA.

General Methods and Systems

It should be understood that the methods described herein for detecting and/or quantifying DNA or RNA in a fluid sample is not limited to the particular detection/quantification assay methods and/or systems described herein. Methods and/or systems which employ single molecule techniques are known in the art, for example, as described in U.S. Pat. No. 8,460,879 (Ser. No. 11/707,385), issued Jun. 11, 2013, entitled "METHODS AND ARRAYS FOR TARGET ANALYTE DETECTION AND DETERMINATION OF TARGET ANALYTE CONCENTRATION IN SOLUTION", by Walt et al.; U.S. Pat. No. 8,460,878 (Ser. No. 11/707,383), issued Jun. 11, 2013, entitled "METHODS AND ARRAYS FOR DETECTING CELLS AND CELLULAR COMPONENTS IN SMALL DEFINED VOLUMES", by Walt et al.; U.S. Pat. No. 8,492,098 (Ser. No. 11/707,384), issued Jul. 23, 2013, entitled "METHODS AND ARRAYS FOR TARGET ANALYTE DETECTION AND DETERMINATION OF REACTION COMPONENTS THAT AFFECT A REACTION", by Walt et al.; International Patent Publication No. WO 2009/029073 (International Patent Application No. PCT/US2007/019184), filed Aug. 30, 2007, entitled "METHODS OF DETERMINING THE CONCENTRATION OF AN ANALYTE IN SOLUTION", by Walt et al.; U.S. Patent Application Publication No. US-2010-0075862 (Ser. No. 12/236,484), filed Sep. 23, 2008, entitled "HIGH SENSITIVITY DETERMINATION OF THE CONCENTRATION OF ANALYTE MOLECULES OR PARTICLES IN A FLUID SAMPLE", by Duffy et al.; U.S. Pat. No. 8,222,047 (Ser. No. 12/236,486), issued Jul. 17, 2012, entitled "ULTRA-SENSITIVE DETECTION OF MOLECULES ON SINGLE MOLECULE ARRAYS", by Duffy et al.; U.S. Patent Application Publication No. US-2010-0075439 (Ser. No. 12/236,488), filed Sep. 23, 2008, entitled "ULTRA-SENSITIVE DETECTION OF MOLECULES BY CAPTURE-AND-RELEASE USING REDUCING AGENTS FOLLOWED BY QUAN- TIFICATION", by Duffy et al.; International Patent Publication No. WO2010/039179 (International Patent Application No. PCT/US2009/005248), filed Sep. 22, 2009, entitled "ULTRA-SENSITIVE DETECTION OF MOLECULES OR ENZYMES", by Duffy et al.; U.S. Patent Application Publication No. US-2010-0075355 (Ser. No. 12/236,490), filed Sep. 23, 2008, entitled "ULTRA-SENSITIVE DETECTION OF ENZYMES BY CAPTURE-AND-RELEASE FOLLOWED BY QUANTIFICATION", by Duffy et al.; U.S. Pat. No. 8,236,574 (Ser. No. 12/731,130), issued Aug. 7, 2012, entitled "ULTRA-SENSITIVE DETECTION OF MOLECULES OR PARTICLES USING BEADS OR OTHER CAPTURE OBJECTS", by Duffy et al.; International Patent Publication No. WO2011/109364 (International Patent Application No. PCT/US2011/026645), filed Mar. 1, 2011, entitled "ULTRA-SENSITIVE DETECTION OF MOLECULES OR PARTICLES USING BEADS OR OTHER CAPTURE OBJECTS", by Duffy et al.; International Patent Publication No. WO2011/109372 (International Patent Application No. PCT/US2011/026657), filed Mar. 1, 2011, entitled "ULTRA-SENSITIVE DETECTION OF MOLECULES USING DUAL DETECTION METHODS", by Duffy et al.; U.S. Patent Application Publication No. US 2011-0212462 (Ser. No. 12/731,135), filed Mar. 24, 2010, entitled "ULTRA-SENSITIVE DETECTION OF MOLECULES USING DUAL DETECTION METHODS", by Duffy et al.; International Patent Publication No. WO2011/109379 (International Patent Application No. PCT/US2011/026665), filed Mar. 1, 2011, entitled "METHODS AND SYSTEMS FOR EXTENDING DYNAMIC RANGE IN ASSAYS FOR THE DETECTION OF MOLECULES OR PARTICLES", by Rissin et al.; U.S. Pat. No. 8,415,171 (Ser. No. 12/731,136), issued Apr. 9, 2013, entitled "METHODS AND SYSTEMS FOR EXTENDING DYNAMIC RANGE IN ASSAYS FOR THE DETECTION OF MOLECULES OR PARTICLES", by Duffy et al.; U.S. patent application Ser. No. 13/035,472, filed Feb. 25, 2011, entitled "SYSTEMS, DEVICES, AND METHODS FOR ULTRA-SENSITIVE DETECTION OF MOLECULES OR PARTICLES", by Fournier et al.; U.S. Patent Application No. US 2011-0245097 (Ser. No. 13/037,987), filed Mar. 1, 2011, entitled "METHODS AND SYSTEMS FOR EXTENDING DYNAMIC RANGE IN ASSAYS FOR THE DETECTION OF MOLECULES OR PARTICLES", by Rissin et al.; each herein incorporated by reference. Any of which, and others, could potentially be employed to practice the current invention and/or could benefit from utilizing the methods described in the context of the present invention.

If some embodiments, the methods employed have low limits of detection and/or limits of quantification as compared to bulk analysis techniques (e.g., ELISA methods). The terms "limit of detection" (or LOD) and "limit of quantification" (or LOQ) are given their ordinary meaning in the art. The LOD refers to the lowest analyte concentration likely to be reliably distinguished from background noise and at which detection is feasible. The LOD as used herein is defined as three standard deviations (SD) above background noise. The LOQ refers to the lowest concentration at which the analyte can not only be reliably detected but at which some predefined goals for bias and imprecision are met. Generally, as is used herein, the LOQ refers to the lowest concentration above the LOD wherein the coefficient of variation (CV) of the measured concentrations is less than about 20%.

In some cases, an assay method employed has a limit of detection and/or a limit of quantification of less than about or about 500 pg/mL, less than about or about 250 pg/mL, less than about or about 100 pg/mL, less than about or about 50 pg/mL, less than about or about 40 pg/mL, less than about or about 30 pg/mL, less than about or about 20 pg/mL, less than about or about 10 pg/mL, less than about or about 5 pg/mL, less than about or about 4 pg/mL, less than about or about 3 pg/mL, less than about or about 2 pg/mL, less than about or about 1 pg/mL, less than about or about 0.8 pg/mL, less than about or about 0.7 pg/mL, less than about or about 0.6 pg/mL, less than about or about 0.5 pg/mL, less than about or about 0.4 pg/mL, less than about or about 0.3 pg/mL, less than about or about 0.2 pg/mL, less than about or about 0.1 pg/mL, less than about or about 0.05 pg/mL, less than about or about 0.04 pg/mL, less than about or about 0.02 pg/mL, less than about or about 0.01 pg/mL, or less. In some cases, an assay method employed has a limit of quantification and/or a limit of detection between about 100 pg/mL and about 0.01 pg/mL, between about 50 pg/mL and about 0.02 pg/mL, between about 25 pg/mL and about 0.02 pg/mL, between about 10 pg/mL and about 0.02 pg/mL. As will be understood by those of ordinary skill the art, the LOQ and/or LOD may differ for each assay method and/or each DNA or RNA determined with the same assay.

In some embodiments, the concentration of DNA or RNA in the fluid sample that may be substantially accurately determined is less than about or about 5000 fM, less than about or about 3000 fM, less than about or about 2000 fM, less than about or about 1000 fM, less than about or about 500 fM, less than about or about 300 fM, less than about or about 200 fM, less than about or about 100 fM, less than about or about 50 fM, less than about or about 25 fM, less than about or about 10 fM, less than about or about 5 fM, less than about or about 2 fM, less than about or about 1 fM, less than about or about 0.5 fM, less than about or about 0.1 fM, or less. In some embodiments, the concentration of DNA or RNA in the fluid sample that may be substantially accurately determined is between about 5000 fM and about 0.1 fM, between about 3000 fM and about 0.1 fM, between about 1000 fM and about 0.1 fM, between about 1000 fM and about 1 fM, between about 100 fM and about 1 fM, between about 100 fM and about 0.1 fM, or the like. The concentration of DNA or RNA in a fluid sample may be considered to be substantially accurately determined if the measured concentration of the DNA or RNA in the fluid sample is within about 10% of the actual (e.g., true) concentration of the DNA or RNA in the fluid sample. In certain embodiments, the measured concentration of the DNA or RNA in the fluid sample may be within about 5%, within about 4%, within about 3%, within about 2%, within about 1%, within about 0.5%, within about 0.4%, within about 0.3%, within about 0.2% or within about 0.1%, of the actual concentration of the DNA or RNA in the fluid sample. In some cases, the measure of the concentration determined differs from the true (e.g., actual) concentration by no greater than about 20%, no greater than about 15%, no greater than 10%, no greater than 5%, no greater than 4%, no greater than 3%, no greater than 2%, no greater than 1%, or no greater than 0.5%. The accuracy of the assay method may be determined, in some embodiments, by determining the concentration of DNA or RNA in a fluid sample of a known concentration using the selected assay method.

In some embodiments, an assay method employs a step of spatially segregating DNA or RNA molecules or fragments into a plurality of locations to facilitate detection/quantification, such that each location comprises/contains either zero or one or more DNA or RNA molecules or fragments, optionally fragmented. Additionally, in some embodiments, the locations may be configured in a manner such that each location can be individually addressed. In some embodiments, a measure of the concentration of DNA or RNA molecules in a fluid sample may be determined by detecting DNA or RNA molecules or fragments immobilized with respect to a binding surface having affinity for at least one type of DNA or RNA molecule or fragment. The binding surface may comprise a plurality of capture probes associated with a surface. In some cases, the binding surface comprises a plurality of capture objects, each comprising a plurality of a single type of capture probe. As described above, a plurality of types of capture probes may be employed, each comprising a plurality of a single type of capture probe, wherein each type of capture probe differs from the other types of capture probes. In certain embodiments the binding surface may form (e.g., a surface of a well/reaction vessel on a substrate) or be contained within (e.g., a surface of a capture object, such as a bead, contained within a well) one of a plurality of locations (e.g., a plurality of wells/reaction vessels) on a substrate (e.g., plate, dish, chip, optical fiber end, etc.). At least a portion of the locations may be addressed and a measure indicative of the number/percentage/fraction of the locations containing at least one DNA or RNA molecule or fragment may be made. In some cases, based upon the number/percentage/fraction, a measure of the concentration of DNA or RNA molecules in the fluid sample may be determined. The measure of the concentration of DNA or RNA molecules in the fluid sample may be determined by a digital analysis method/system optionally employing Poisson distribution adjustment and/or based at least in part on a measured intensity of a signal, as will be known to those of ordinary skill in the art. In some cases, the assay methods and/or systems may be automated.

Additional details of exemplary, non-limiting assay methods which comprise one or more steps of spatially segregating DNA or RNA molecules or fragments will now be described. In certain embodiments, a method for detection and/or quantifying DNA or RNA molecules in a sample comprises immobilizing a plurality of DNA or RNA molecules or fragments with respect to a plurality of capture objects (e.g., beads) that each include a binding surface having affinity for at least one type of DNA or RNA molecules or fragments. For example, the capture objects may comprise a plurality of beads comprising a plurality of capture probes (e.g., nucleic acid sequence(s) having specific affinity for a DNA or RNA molecule or fragment. However, in some embodiments, no capture objects are employed. As described herein, in some embodiments, a plurality of types of capture objects may be provided, each comprising a plurality of a unique type of capture probes (e.g., nucleic acid sequence having specific affinity for a DNA or RNA molecule or fragment. At least some of the capture objects (e.g., at least some associated with at least one DNA or RNA molecule or fragment) may be spatially separated/segregated into a plurality of locations, and at least some of the locations may be addressed/interrogated (e.g., using an imaging system). A measure of the concentration of DNA or RNA molecules in the fluid sample may be determined based on the information received when addressing the locations (e.g., using the information received from the imaging system and/or processed using a computer implemented control system). In some cases, a measure of the concentration may be based at least in part on the number of locations determined to contain a capture object that is or was associated with at least one DNA or RNA molecule or fragment. In other cases and/or under differing conditions, a measure of the concentration may be based at least in part on an intensity level of at least one signal indicative of the presence of a plurality of DNA or RNA molecule or fragment and/or capture objects associated with a DNA or RNA molecule or fragment at one or more of the addressed locations.

In some embodiments, the number/percentage/fraction of locations containing a capture object but not containing a DNA or RNA molecule or fragment may also be determined and/or the number/percentage/fraction of locations not containing any capture object may also be determined. In such embodiments, a measure of the concentration of DNA or RNA molecules in the fluid sample may be based at least in part on the ratio of the number of locations determined to contain a capture object associated with a DNA or RNA molecule or fragment to the total number of locations determined to contain a capture object not associated with a DNA or RNA molecule or fragment, and/or a measure of the concentration of DNA or RNA molecules in the fluid sample may be based at least in part on the ratio of the number of locations determined to contain a capture object associated with a DNA or RNA molecule or fragment to the number of locations determined to not contain any capture objects, and/or a measure of the concentration of DNA or RNA molecule or fragment in the fluid sample may be based at least in part on the ratio of the number of locations determined to contain a capture object associated with a DNA or RNA molecule or fragment to the number of locations determined to contain a capture object. In yet other embodiments, a measure of the concentration of DNA or RNA molecules in a fluid sample may be based at least in part on the ratio of the number of locations determined to contain a capture object and a DNA or RNA molecule or fragment to the total number of locations addressed and/or analyzed.

In certain embodiments, at least some of the plurality of capture objects (e.g., at least some associated with at least one DNA or RNA molecule or fragment) are spatially separated into a plurality of locations, for example, a plurality of reaction vessels in an array format. The plurality of reaction vessels may be formed in, on and/or of any suitable material, and in some cases, the reaction vessels can be sealed or may be formed upon the mating of a substrate with a sealing component, as discussed in more detail below. In certain embodiments, especially where quantization of the capture objects associated with at least one DNA or RNA molecule or fragment is desired, the partitioning of the capture objects can be performed such that at least some (e.g., a statistically significant fraction; e.g., as described in International Patent Application No. PCT/US2011/026645, filed Mar. 1, 2011, published as WO 2011/109364 on Sep. 9, 2011, entitled "ULTRA-SENSITIVE DETECTION OF MOLECULES OR PARTICLES USING BEADS OR OTHER CAPTURE OBJECTS", by Duffy et al.) of the reaction vessels comprise at least one or, in certain cases, only one capture object associated with at least one DNA or RNA molecule or fragment and at least some (e.g., a statistically significant fraction) of the reaction vessels comprise an capture object not associated with any DNA or RNA molecules or fragment. The capture objects associated with at least one DNA or RNA molecule or fragment may be quantified in certain embodiments, thereby allowing for the detection and/or quantification of DNA or RNA molecules in the fluid sample by techniques described in more detail herein.

An exemplary assay method may proceed as follows. A sample fluid containing or suspected of containing DNA or RNA molecules or fragments is provided. The DNA or RNA molecules are exposed to at least one of a plurality of types of detection probes or a plurality of types of capture probes.

An assay consumable comprising a plurality of assay sites is exposed to the sample fluid. In some cases, the DNA or RNA molecules or fragments are provided in a manner (e.g., at a concentration) such that a statistically significant fraction of the assay sites contain a single DNA or RNA molecule or fragment and a statistically significant fraction of the assay sites do not contain any DNA or RNA molecules or fragments. The assay sites may optionally be exposed to a variety of reagents (e.g., using a reagent loader) and or rinsed. The assay sites may then optionally be sealed and imaged (see, for example, U.S. patent application Ser. No. 13/035,472, filed Feb. 25, 2011, entitled "SYSTEMS, DEVICES, AND METHODS FOR ULTRA-SENSITIVE DETECTION OF MOLECULES OR PARTICLES", by Fournier et al.). The images are then analyzed (e.g., using a computer implemented control system) such that a measure of the concentration of the DNA or RNA molecules in the fluid sample may be obtained, based at least in part, by determination of the number/fraction/percentage of assay sites which contain a DNA or RNA molecule or fragment and/or the number/fraction/percentage of sites which do not contain any DNA or RNA molecules or fragments. In some cases, the DNA or RNA molecules or fragments are provided in a manner (e.g., at a concentration) such that at least some assay sites comprise more than one DNA or RNA molecule or fragment. In such embodiments, a measure of the concentration of DNA or RNA molecules in the fluid sample may be obtained at least in part on an intensity level of at least one signal indicative of the presence of a plurality of DNA or RNA molecules or fragments at one or more of the assay sites.

Figure 7:
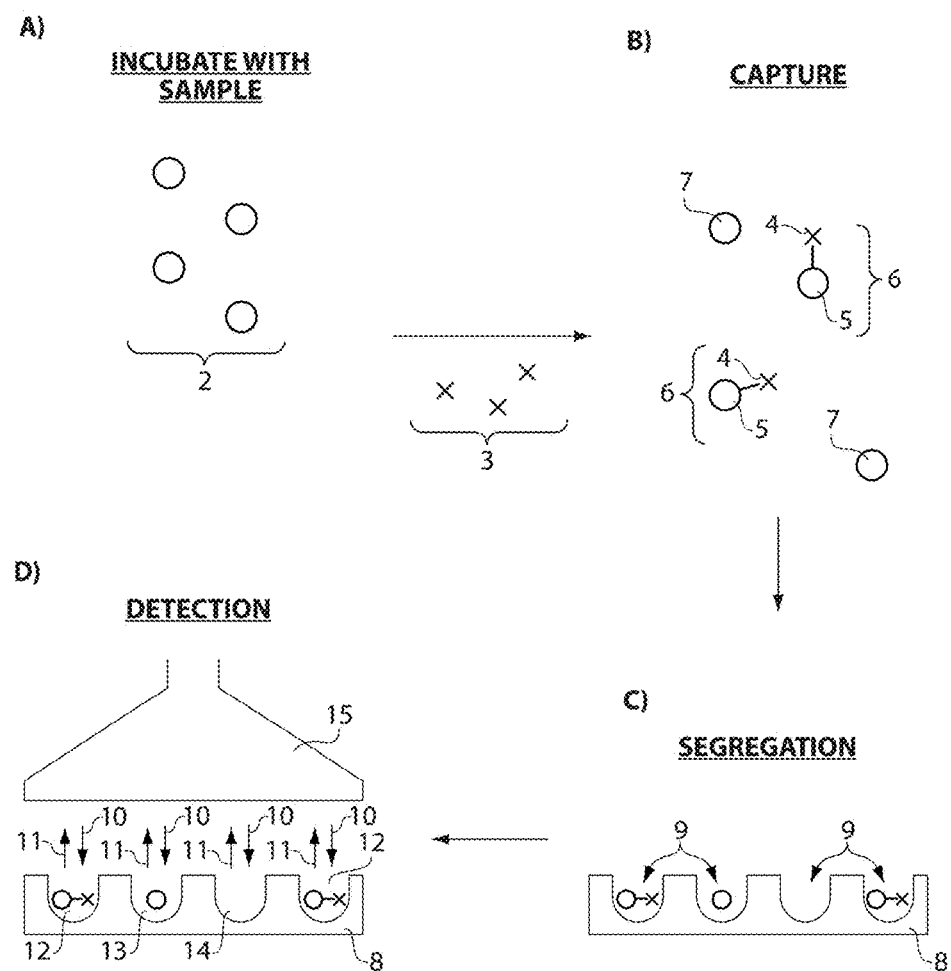
FIGS. 7 and 8 depict non-limiting assay methods, according to some embodiments.

An exemplary embodiment of an assay method that may be used in certain embodiments of the invention is illustrated in FIG. 7. A plurality of capture objects 2, are provided (step (A)). In this particular example, the plurality of capture objects comprises a plurality of beads. The plurality of capture objects may comprise a plurality of types, wherein each type may comprise a sequence complimentary to the DNA or RNA molecules or fragments, as described herein. The beads are exposed to a fluid sample containing a plurality of DNA or RNA molecules or fragments 3 (e.g., beads 2 are incubated with DNA or RNA molecules or fragments 3). At least some of the DNA or RNA molecules or fragments are immobilized with respect to a bead. In this example, the DNA or RNA molecules or fragments are provided in a manner (e.g., at a concentration) such that a statistically significant fraction of the beads associate with a single DNA or RNA molecule or fragment and a statistically significant fraction of the beads do not associate with any DNA or RNA molecules or fragments. For example, as shown in step (B), DNA or RNA molecule or fragment 4 is immobilized with respect to bead 5, thereby forming complex 6, whereas some beads 7 are not associated with any DNA or RNA molecules or fragments. It should be understood, in some embodiments, more than one DNA or RNA molecule or fragment may associate with at least some of the beads, as described herein. The sample may optionally then be expose to one or more types of detection probes, wherein at least some of the DNA or RNA molecules or fragments associate with at least one detection probe. At least some of the plurality of beads (e.g., those associated with a single DNA or RNA molecule or fragment or not associated with any DNA or RNA molecules or fragments) may then be spatially separated/segregated into a plurality of locations. As shown in step (C), the plurality of locations is illustrated as substrate 8 comprising a plurality of wells/reaction vessels 9. In this example, each reaction vessel comprises either zero or one beads. At least some of the reaction vessels may then be addressed (e.g., optically or via other detection means) to determine the number of locations containing a DNA or RNA molecule or fragment, for example, via detection of a detection probe. For example, as shown in step (D), the plurality of reaction vessels are interrogated optically using light source 15, wherein each reaction vessel is exposed to electromagnetic radiation (represented by arrows 10) from light source 15. The light emitted (represented by arrows 11) from each reaction vessel is determined (and/or recorded) by detector 15 (in this example, housed in the same system as light source 15). The number of reaction vessels containing a DNA or RNA molecule or fragment (e.g., reaction vessels 12) is determined based on the light detected from the reaction vessels. In some cases, the number of reaction vessels containing a bead not associated with a DNA or RNA molecule or fragment (e.g., reaction vessel 13), the number of wells not containing a bead (e.g., reaction vessel 14) and/or the total number of wells addressed may also be determined. Such determination(s) may then be used to determine a measure of the concentration of DNA or RNA molecules in the fluid sample.

Figure 8:
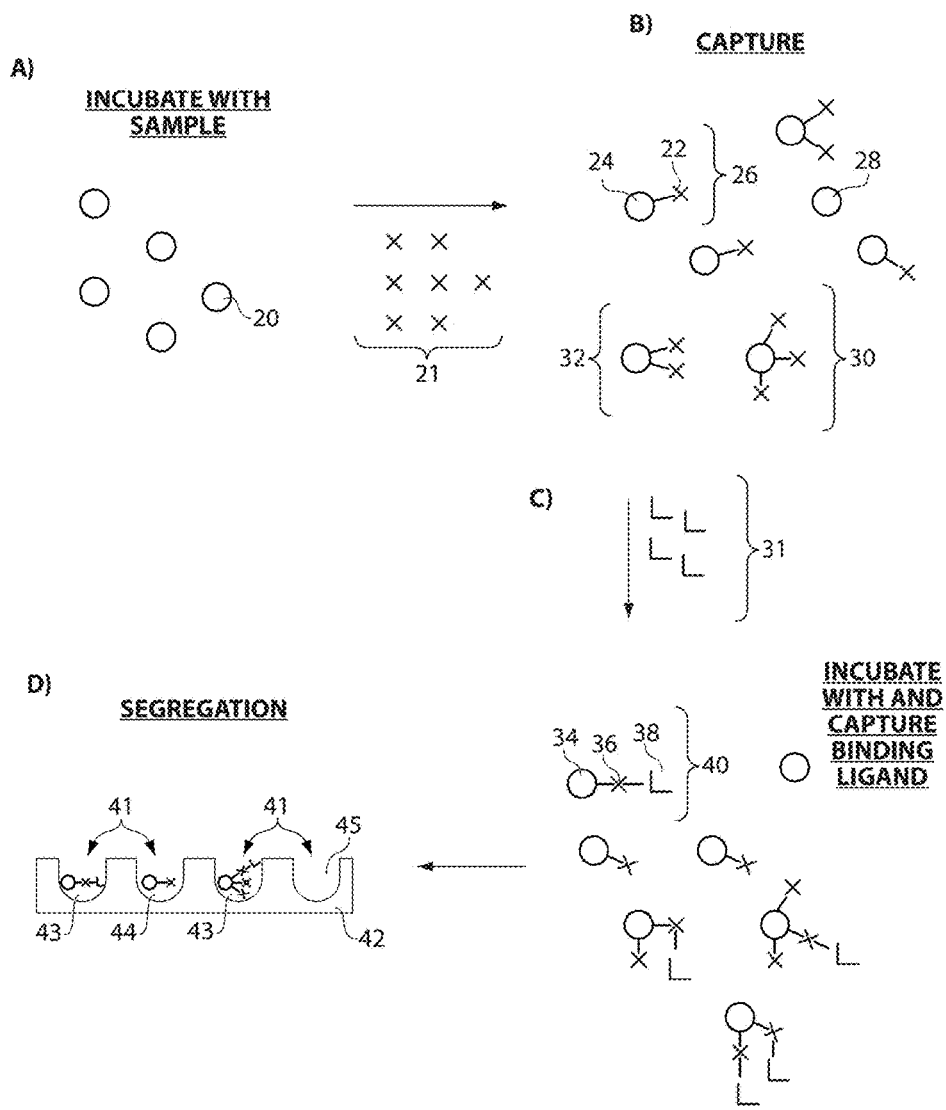

A non-limiting example of an embodiment where a capture object is associated with more than one DNA or RNA molecule or fragment is illustrated in FIG. 8. A plurality of capture objects 20 are provided (step (A)). In this example, the plurality of capture objects comprises a plurality of beads. The plurality of beads is exposed to a fluid sample containing plurality of DNA or RNA molecules or fragments 21 (e.g., beads 20 are incubated with DNA or RNA molecules or fragments 21). At least some of the DNA or RNA molecules or fragments are immobilized with respect to a bead. For example, as shown in step (B), DNA or RNA molecule or fragment 22 is immobilized with respect to bead 24, thereby forming complex 26. Also illustrated is complex 30 comprising a bead immobilized with respect to three DNA or RNA molecules or fragments and complex 32 comprising a bead immobilized with respect to two DNA or RNA molecules or fragments. Additionally, in some cases, some of the beads may not associate with any DNA or RNA molecules or fragments (e.g., bead 28). The plurality of beads from step (B) is exposed to a plurality of detection probes 31. The plurality of detection probes may comprise a plurality of types, wherein each type comprises a sequence complimentary to the DNA or RNA molecule or fragment, as described herein. As shown in step (C), a detection probe associates with some of the DNA or RNA molecules or fragments immobilized with respect to a bead. For example, complex 40 comprises bead 34, DNA or RNA molecules or fragments 36, and detection probe 38. The detection probes are provided in a manner such that a statistically significant fraction of the beads comprising at least one DNA or RNA molecule or fragment become associated with at least one detection probe (e.g., one, two, three, etc.) and a statistically significant fraction of the beads comprising at least one DNA or RNA molecule or fragment do not become associated with any detection probes. At least a portion of the plurality of beads from step (C) is then spatially separated into a plurality of locations. As shown in step (D), in this example, the locations comprise a plurality of reaction vessels 41 on a substrate 42. The plurality of reaction vessels may be exposed to the plurality of beads from step (C) such at each reaction vessel contains zero or one beads. The substrate may then be analyzed to determine the number of reaction vessels containing a detection probe (e.g., reaction vessels 43), wherein in the number may be related to a measure of the concentration of DNA or RNA molecules in the fluid sample. In some cases, the number of reaction vessels containing a bead and not containing a detection probe (e.g., reaction vessel 44), the number of reaction vessels not containing a bead (e.g., reaction vessel 45), and/or the total number of reaction vessels addressed/analyzed may also be determined. Such determination(s) may then be used to determine a measure of the concentration of DNA or RNA molecule or fragments in the fluid sample.

In some embodiments, a measure of the concentration of DNA or RNA molecules in the fluid sample may be determined at least in part using a calibration curve developed using samples containing known concentrations of target analyte molecules. In some cases, a measure of the concentration of DNA or RNA molecules in the fluid sample may be determined at least in part by comparison of a measured parameter to a calibration standard. In some cases, a calibration curve may be prepare, wherein the total measured signal is determined for a plurality of samples comprising the DNA or RNA molecule at a known concentration using a substantially similar assay format. For example, the number and/or fraction of locations that comprise a DNA or RNA molecule or fragment (e.g., based on a binary read-out; optionally associated with a capture probe or capture object), or alternatively, the total intensity of the array, may be compared to a calibration curve to determine a measure of the concentration of the DNA or RNA molecule in the fluid sample. The calibration curve may be produced by completing the assay with a plurality of standardized samples of known concentration under similar conditions used to analyze test samples with unknown concentrations. A calibration curve may relate the number or fraction of the locations determined to contain a DNA or RNA molecule or fragment (and/or detection probe) with a known concentration of the DNA or RNA molecule, or alternatively to the number or fraction of capture objects associated with a DNA or RNA molecule or fragment. The assay may then be completed on a sample containing the DNA or RNA molecule or fragment in an unknown concentration, and number/fraction of locations or capture objects determined to contain or be associated with an DNA or RNA molecule or fragment (and/or detection probe) may be compared to the calibration curve, (or a mathematical equation fitting same) to determine a measure of the concentration of the DNA or RNA molecules in the fluid sample.

In some embodiments, a plurality of locations may be addressed and/or a plurality of capture objects and/or species/molecules/particles of interest may be detected substantially simultaneously. "Substantially simultaneously" when used in this context, refers to addressing/detection of the locations/capture objects/species/molecules/particles of interest at approximately the same time such that the time periods during which at least two locations/capture objects/species/molecules/particles of interest are addressed/detected overlap, as opposed to being sequentially addressed/detected, where they would not. Simultaneous addressing/detection can be accomplished by using various techniques, including optical techniques (e.g., CCD detector). Spatially segregating capture objects/species/molecules/particles into a plurality of discrete, resolvable locations, according to some embodiments facilitates substantially simultaneous detection by allowing multiple locations to be addressed substantially simultaneously. For example, for embodiments where individual species/molecules/particles are associated with capture objects that are spatially segregated with respect to the other capture objects into a plurality of discrete, separately resolvable locations during detection, substantially simultaneously addressing the plurality of discrete, separately resolvable locations permits individual capture objects, and thus individual species/molecules/particles (e.g., DNA or RNA molecule or fragment) to be resolved. For example, in certain embodiments, individual molecules/particles of a plurality of molecules/particles are partitioned across a plurality of reaction vessels such that each reaction vessel contains zero or only one species/molecule/particle. In some cases, at least about 80%, at least about 85%, at least about 90%, at least about 95%, at least about 96%, at least about 97%, at least about 98%, at least about 99%, at least about 99.5% of all species/molecules/particles are spatially separated with respect to other species/molecules/particles during detection. A plurality of species/molecules/particles may be detected substantially simultaneously within a time period of less than about 1 second, less than about 500 milliseconds, less than about 100 milliseconds, less than about 50 milliseconds, less than about 10 milliseconds, less than about 1 millisecond, less than about 500 microseconds, less than about 100 microseconds, less than about 50 microseconds, less than about 10 microseconds, less than about 1 microsecond, less than about 0.5 microseconds, less than about 0.1 microseconds, or less than about 0.01 microseconds, less than about 0.001 microseconds, or less. In some embodiments, the plurality of species/molecules/particles may be detected substantially simultaneously within a time period of between about 100 microseconds and about 0.001 microseconds, between about 10 microseconds and about 0.01 microseconds, or less.

In some embodiments, the locations are optically interrogated. The locations exhibiting changes in their optical signature may be identified by a conventional optical train and optical detection system. Depending on the detected species (e.g., type of fluorescence entity, etc.) and the operative wavelengths, optical filters designed for a particular wavelength may be employed for optical interrogation of the locations. In embodiments where optical interrogation is used, the system may comprise more than one light source and/or a plurality of filters to adjust the wavelength and/or intensity of the light source. In some embodiments, the optical signal from a plurality of locations is captured using a CCD camera.

In some embodiments of the present invention, the plurality of reaction vessels may be sealed (e.g., after the introduction of the DNA or RNA molecules or fragments, detection probes, and/or precursor labeling agent), for example, through the mating of the second substrate and a sealing component. Non-limiting examples films that a sealing component may comprise include solid films (e.g., of a compliant material), fluid films (e.g., of fluids substantially immiscible with sample fluid contained in the assay sites), or the like. The sealing of the reaction vessels may be such that the contents of each reaction vessel cannot escape the reaction vessel during the remainder of the assay. In some cases, the reaction vessels may be sealed after the addition of the DNA or RNA molecules or fragments and, optionally, at least one type of precursor labeling agent to facilitate detection of the DNA or RNA molecules or fragments. For embodiments employing precursor labeling agents, by sealing the contents in some or each reaction vessel, a reaction to produce the detectable labeling agents can proceed within the sealed reaction vessels, thereby producing a detectable amount of labeling agents that is retained in the reaction vessel for detection purposes.

In some embodiments, the sealing component may be a fluid. The fluid comprising the sealing component is advantageously substantially immiscible with the fluid contained in the assay sites. As used herein, a "fluid" is given its ordinary meaning, i.e., a liquid or a gas. The fluid may have any suitable viscosity that permits flow. If two or more fluids are present, the fluids may each be substantially miscible or substantially immiscible. In some cases, the fluid(s) comprising the sealing component can miscible or partially miscible with the assay sample fluid at equilibrium, but may be selected to be substantially immiscible with the assay sample fluid within the time frame of the assay or interaction. Those of ordinary skill in the art can select suitable sealing fluids, such as fluids substantially immiscible with sample fluids, using contact angle measurements or the like, to carry out the techniques of the invention. In some cases, the sample fluid and/or rinsing fluid and/or reagent fluid is an aqueous solution and the sealing component comprises a non-aqueous fluid. Non-limiting examples of potentially suitable non-aqueous fluids include fluorous liquids, oils (e.g., mineral oils, fluorinated oils), ferrofluids, non-aqueous polymer solutions (e.g., thickeners), and the like. In other cases, the sample fluid and/or rinsing fluid and/or reagent fluid is a non-aqueous solution and the sealing component comprising an aqueous fluid. In some cases, the sample fluid is a hydrogel whose viscosity changes upon temperature or other physicochemical triggers.

The plurality of locations may be formed may be formed using a variety of methods and/or materials. In some embodiments, the plurality of locations comprises a plurality of reaction vessels/wells on a substrate. In some cases, the plurality of reaction vessels is formed as an array of depressions on a first surface. In other cases, however, the plurality of reaction vessels may be formed by mating a sealing component comprising a plurality of depressions with a substrate that may either have a featureless surface or include depressions aligned with those on the sealing component. Any of the device components, for example, the substrate or sealing component, may be fabricated from a compliant material, e.g., an elastomeric polymer material, to aid in sealing. The surfaces may be or made to be hydrophobic or contain hydrophobic regions to minimize leakage of aqueous samples from the microwells. The reactions vessels, in certain embodiments, may be configured to receive and contain only a single capture object.

In some embodiments, the reaction vessels may all have approximately the same volume. In other embodiments, the reaction vessels may have differing volumes. The volume of each individual reaction vessel may be selected to be appropriate to facilitate any particular assay protocol. For example, in one set of embodiments where it is desirable to limit the number of capture objects used for DNA or RNA molecule or fragment capture contained in each vessel to a small number, the volume of the reaction vessels may range from attoliters or smaller to nanoliters or larger depending upon the nature of the capture objects, the detection technique and equipment employed, the number and density of the wells on the substrate and the expected concentration of capture objects in the fluid applied to the substrate containing the wells. In one embodiment, the size of the reaction vessel may be selected such only a single capture object used for DNA or RNA molecule or fragment capture can be fully contained within the reaction vessel (see, for example, U.S. patent application Ser. No. 12/731,130, filed Mar. 24, 2010, published as US-2011-0212848 on Sep. 1, 2011, entitled "ULTRA-SENSITIVE DETECTION OF MOLECULES OR PARTICLES USING BEADS OR OTHER CAPTURE OBJECTS", by Duffy et al.; International Patent Application No. PCT/US2011/026645, filed Mar. 1, 2011, published as WO 2011/109364 on Sep. 9, 2011, entitled "ULTRA-SENSITIVE DETECTION OF MOLECULES OR PARTICLES USING BEADS OR OTHER CAPTURE OBJECTS", by Duffy et al., each herein incorporated by reference).

In some embodiments, the reaction vessels may have a volume between about 1 femtoliter and about 1 picoliter, between about 1 femtoliters and about 100 femtoliters, between about 10 attoliters and about 100 picoliters, between about 1 picoliter and about 100 picoliters, between about 1 femtoliter and about 1 picoliter, or between about 30 femtoliters and about 60 femtoliters. In some cases, the reaction vessels have a volume of less than about 1 picoliter, less than about 500 femtoliters, less than about 100 femtoliters, less than about 50 femtoliters, or less than about 1 femtoliter. In some cases, the reaction vessels have a volume of about 10 femtoliters, about 20 femtoliters, about 30 femtoliters, about 40 femtoliters, about 50 femtoliters, about 60 femtoliters, about 70 femtoliters, about 80 femtoliters, about 90 femtoliters, or about 100 femtoliters.

The total number of locations and/or density of the locations employed in an assay (e.g., the number/density of reaction vessels in an array) can depend on the composition and end use of the array. For example, the number of reaction vessels employed may depend on the number of types of DNA or RNA molecules or fragments and/or detection probes employed, the suspected concentration range of the assay, the method of detection, the size of the capture objects, the type of detection entity (e.g., free labeling agent in solution, precipitating labeling agent, etc.). Arrays containing from about 2 to many billions of reaction vessels (or total number of reaction vessels) can be made by utilizing a variety of techniques and materials. Increasing the number of reaction vessels in the array can be used to increase the dynamic range of an assay or to allow multiple samples or multiple types of DNA or RNA molecules or fragments to be assayed in parallel. The array may comprise between one thousand and one million reaction vessels per sample to be analyzed. In some cases, the array comprises greater than one million reaction vessels. In some embodiments, the array comprises between about 1,000 and about 50,000, between about 1,000 and about 1,000,000, between about 1,000 and about 10,000, between about 10,000 and about 100,000, between about 100,000 and about 1,000,000, between about 100,000 and about 500,000, between about 1,000 and about 100,000, between about 50,000 and about 100,000, between about 20,000 and about 80,000, between about 30,000 and about 70,000, between about 40,000 and about 60,000 reaction vessels. In some embodiments, the array comprises about 10,000, about 20,000, about 50,000, about 100,000, about 150,000, about 200,000, about 300,000, about 500,000, about 1,000,000, or more, reaction vessels.

The array of reaction vessels may be arranged on a substantially planar surface or in a non-planar three-dimensional arrangement. The reaction vessels may be arrayed in a regular pattern or may be randomly distributed. In a specific embodiment, the array is a regular pattern of sites on a substantially planar surface permitting the sites to be addressed in the X-Y coordinate plane.

In some embodiments, the reaction vessels are formed in a solid material. As will be appreciated by those in the art, the number of potentially suitable materials in which the reaction vessels can be formed is very large, and includes, but is not limited to, glass (including modified and/or functionalized glass), plastics (including acrylics, polystyrene and copolymers of styrene and other materials, polypropylene, polyethylene, polybutylene, polyurethanes, cyclic olefin copolymer (COC), cyclic olefin polymer (COP), Teflon®, polysaccharides, nylon or nitrocellulose, etc.), elastomers (such as poly(dimethyl siloxane) and polyurethanes), composite materials, ceramics, silica or silica-based materials (including silicon and modified silicon), carbon, metals, optical fiber bundles, or the like. In general, the substrate material may be selected to allow for optical detection without appreciable autofluorescence. In certain embodiments, the reaction vessels may be formed in a flexible material.

A reaction vessel in a surface (e.g., substrate or sealing component) may be formed using a variety of techniques known in the art, including, but not limited to, photolithography, stamping techniques, molding techniques, etching techniques, or the like. As will be appreciated by those of the ordinary skill in the art, the technique used can depend on the composition and shape of the supporting material and the size and number of reaction vessels.

In a particular embodiment, an array of reaction vessels is formed by creating microwells on one end of a fiber optic bundle and utilizing a planar compliant surface as a sealing component. In certain such embodiments, an array of reaction vessels in the end of a fiber optic bundle may be formed as follows. First, an array of microwells is etched into the end of a polished fiber optic bundle. Techniques and materials for forming and etching a fiber optic bundle are known to those of ordinary skill in the art. For example, the diameter of the optical fibers, the presence, size and composition of core and cladding regions of the fiber, and the depth and specificity of the etch may be varied by the etching technique chosen so that microwells of the desired volume may be formed. In certain embodiments, the etching process creates microwells by preferentially etching the core material of the individual glass fibers in the bundle such that each well is approximately aligned with a single fiber and isolated from adjacent wells by the cladding material. Potential advantages of the fiber optic array format is that it can produce thousands to millions of reaction vessels without complicated microfabrication procedures and that it can provide the ability to observe and optically address many reaction vessels simultaneously.

Each microwell may be aligned with an optical fiber in the bundle so that the fiber optic bundle can carry both excitation and emission light to and from the wells, enabling remote interrogation of the well contents. Further, an array of optical fibers may provide the capability for simultaneous or non-simultaneous excitation of molecules in adjacent vessels, without signal "cross-talk" between fibers. That is, excitation light transmitted in one fiber does not escape to a neighboring fiber.

Alternatively, the equivalent structures of a plurality of reaction vessels may be fabricated using other methods and materials that do not utilize the ends of an optical fiber bundle as a substrate. For example, the array may be a spotted, printed or photolithographically fabricated substrate produced by techniques known in the art; see for example WO95/25116; WO95/35505; PCT US98/09163; U.S. Pat. Nos. 5,700,637, 5,807,522, 5,445,934, 6,406,845, and 6,482,593. In some cases, the array may be produced using molding, embossing, and/or etching techniques as will be known to those of ordinary skill in the art.

In some embodiments, the plurality of locations may not comprise a plurality of reaction vessels/wells. For example, in embodiments where capture objects are employed, a patterned substantially planar surface may be employed and the patterned areas form a plurality of locations. In some cases, the patterned areas may comprise substantially hydrophilic surfaces which are substantially surrounded by substantially hydrophobic surfaces. In certain embodiments, a plurality of capture objects (e.g., beads) may be substantially surrounded by a substantially hydrophilic medium (e.g., comprising water), and the beads may be exposed to the patterned surface such that the beads associate in the patterned areas (e.g., the hydrophilic locations on the surface), thereby spatially segregating the plurality of beads. For example, in one such embodiment, a substrate may be or include a gel or other material able to provide a sufficient barrier to mass transport (e.g., convective and/or diffusional barrier) to prevent capture objects used for DNA or RNA molecule or fragment capture and/or precursor labeling agent and/or labeling agent from moving from one location on or in the material to another location so as to cause interference or cross-talk between spatial locations containing different capture objects during the time frame required to address the locations and complete the assay. For example, in one embodiment, a plurality of capture objects is spatially separated by dispersing the capture objects on and/or in a hydrogel material. In some cases, a precursor labeling agent may be already present in the hydrogel, thereby facilitating development of a local concentration of the labeling agent (e.g., upon exposure to a detection probe or DNA or RNA molecule or fragment carrying an enzymatic component). As still yet another embodiment, the capture objects may be confined in one or more capillaries. In some cases, the plurality of capture objects may be absorbed or localized on a porous or fibrous substrate, for example, filter paper. In some embodiments, the capture objects may be spatially segregated on a uniform surface (e.g., a planar surface), and the capture objects may be detected using precursor labeling agents which are converted to substantially insoluble or precipitating labeling agents that remain localized at or near the location of where the corresponding capture object is localized. The use of such substantially insoluble or precipitating labeling agents is described herein. In some cases, single DNA or RNA molecules or fragments may be spatially segregated into a plurality of droplets. That is, single DNA or RNA molecules or fragments may be substantially contained in a droplet containing a first fluid. The droplet may be substantially surrounded by a second fluid, wherein the second fluid is substantially immiscible with the first fluid.

In some embodiments, during the assay, at least one washing step may be carried out. In certain embodiments, the wash solution is selected so that it does not cause appreciable change to the configuration of the capture objects and/or DNA or RNA molecules or fragments and/or does not disrupt any specific binding interaction between at least two components of the assay (e.g., a capture probe and a DNA or RNA molecule or fragment). In other cases, the wash solution may be a solution that is selected to chemically interact with one or more assay components. As will be understood by those of ordinary skill in the art, a wash step may be performed at any appropriate time point during the inventive methods. For example, a plurality of capture objects may be washed after exposing the capture objects to one or more solutions comprising DNA or RNA molecules or fragments, detection probes, precursor labeling agents, or the like. As another example, following immobilization of the DNA or RNA molecules or fragments with respect to a plurality of capture objects, the plurality of capture objects may be subjected to a washing step thereby removing any DNA or RNA molecules or fragments not specifically immobilized with respect to a capture object.

Other assay methods in addition to those described herein are known in the art and may be used in connection with the inventive methods. For example, various analyzers are commercially available for the determination of the concentration of DNA or RNA molecules or fragments.

Those of ordinary skill in the art will be aware of suitable techniques and systems for generating single stranded (ss) DNA from double stranded (ds) DNA, or making sure that RNA does not have hybridized secondary structures, an important step in promoting binding to the capture and detection probes. In some embodiments, ss DNA or RNA may be generated by exposure to heat (melting). In other embodiments, single stranded DNA or RNA may be generated by exposure to low pH (e.g., by adding concentrated NaOH) or high pH (e.g., by addition of concentrated HCl, optionally followed by neutralizing (e.g., by addition of HCl or NaOH, respectively). ss DNA may also be generated by exposure to low salt conditions (e.g., deionized water). Enzymes, e.g., helicases, may also be used to generate single stranded DNA. Organic solvents may also be used to generate ss DNA from ds DNA, for examples, formamide, dimethyl sulfoxide, methanol, ethanol, n-propanol, isopropanol, 1,4-dioxane, glycerol, and ethylene glycol.

The following examples are included to demonstrate various features of the invention. Those of ordinary skill in the art should, in light of the present disclosure, appreciate that many changes can be made in the specific embodiments which are disclosed while still obtaining a like or similar result without departing from the scope of the invention as defined by the appended claims. Accordingly, the following examples are intended only to illustrate certain features of the present invention, but do not necessarily exemplify the full scope of the invention.

Example 1

According to some aspects, methods for the sensitive measurement of genomic DNA based on the direct detection of single molecules of DNA in arrays of femtoliter wells are provided. The method may begin by generating short fragments of DNA from large, double-stranded molecules of genomic DNA using either restriction enzymes or sonication. Single-stranded fragments can then be generated by melting the duplex, and these fragments can be hybridized to complementary biotinylated detection probes and capture probes on paramagnetic beads. The resulting DNA complexes can then be labeled with an enzyme (streptavidin-β-galactosidase), and single enzymes associated with these complexes on beads may be detected in single molecule arrays. DNA concentration can be quantified by determining the average number of enzymes per bead via Poisson statistics (digital) or the average bead intensity (analog). In some cases, the single molecule array DNA assay was used to detect genomic DNA purified from S. aureus with an average limit of detection (LOD) of 0.07 fM, or 2,100 DNA molecules per 50 µL sample. This assay to detected S. aureus spiked into: a) whole blood, with an average LOD of 1,100 bacteria per 25 µL sample (0.074 fM); and, b) water from the Charles River, with an LOD of 1,300 bacteria per 50 µL sample (0.042 fM). Bacteria were detected in river water without prior purification of DNA.

In some embodiments, single molecule array technology can be used to detect genomic ds-DNA in complex samples at low concentrations without molecular replication. In some cases, a single molecule array assay is based on capturing small numbers of target molecules on a large excess of paramagnetic beads, and labeling the captured molecules with an enzyme using a sandwich assay based on the enzyme-linked immunosorbent assay (ELISA). Individual beads are then isolated in microwells in the presence of enzyme substrate, sealed, and arrays of microwells are imaged at the emission wavelength of the fluorescent enzymatic product. The fraction of beads with a fluorescent signal is then determined by counting, and can be related to the target concentration via Poisson statistics. At low concentrations, where there are fewer labeled target molecules than beads, the majority of active beads are associated with single molecules.

Experimental Section

General.

The materials used for assays, and the methods for preparing beads are described in herein.

Preparation of Target DNA and Bacteria.

Staphylococcus aureus (S. aureus, ATCC No. 25923) was obtained from ATCC. Samples of the strain were resuspended from frozen aliquots and grown at 37° C. for 48 h. Subcultures were performed prior to cell count estimation and purification. The number of cells was determined using a Beckman Coulter counter, and aliquots, each containing approximately $10^9$ cells, were taken from the subculture tubes. Genomic DNA from cultured bacteria was purified using the DNeasy Blood and Tissue kit (Qiagen). Two DNA plasmids were also prepared that contained sequences from S. aureus. A full-length 966-bp PCR amplicon of the target gene (nuc; GeneBank: v01281.1) encoding nuclease for S. aureus was cloned into pUC57-Kan vector (GENEWIZ, Inc.). A short target sequence (152 bp) of the nuc gene was cloned into pcDNA 3.1(−) (GENEWIZ, Inc.). The purities of DNA samples were characterized using gel electrophoresis, and concentrations of DNA were determined using optical density on a NanoDrop (Thermo Scientific).

Sequence Design.

Array Designer 4 (Premier Biosoft) was used to design sequences for sets of capture and detection probes. Each probe was 25-50 bases long and complementary to different sites of the target. Probe sequences were carefully selected to be specific to the target and have similar melting temperatures. Capture probes were modified with an amino group at the 5' end for immobilization to carboxyl-presenting paramagnetic beads. Detection probes were modified with biotin at the 3' end. The specific sequences used are provided in Tables 1, 2, and 3.

Fragmentation, Capture, and Labeling of Target DNA.

Samples of genomic DNA or plasmids were fragmented into smaller sizes (200-1000 bp) by physical shearing using an Adaptive Focused Acoustics™ (AFA) sonicator (Covaris, Inc.), or via digestion using restriction enzymes. The restriction enzymes EcoRI and BamHI were used to specifically fragment the plasmid pcDNA 3.1 (−) with 152 bp-long sequence inserted. EcoRI, XhoI, and AluI were used to fragment the plasmid pUC57-Kan with the 966-bp target gene inserted. DraI and AluI were used to fragment genomic DNA from S. aureus. Fragmented DNA samples were diluted two-fold with hybridization buffer (10×SSC+20% dextran+0.2% Tween-20), and mixed with biotinylated detection probes. The mixed DNA samples and detection probes were heated at 95° C. for 7 min, quickly cooled on ice, and hybridized with capture beads for 1.5 h at 42° C. After hybridization, the capture beads were washed four times with 0.2×SSC and 0.1% Tween-20, and then incubated with a solution of ~200 pM streptavidin-β-galactosidase (SβG) for 30 min at 23° C. The enzyme-labeled capture beads were washed eight times with 5×PBS and 0.1% Tween-20, and loaded into arrays of femtoliter wells as described previously.

Detection.

The experimental methods and image analyses used to detect single enzymes on isolated paramagnetic beads using single molecule array assays have been described elsewhere. The total assay time for 48 samples was ~5.5 h based on serial sonication of individual samples on the AFA sonicator. Detection using real-time PCR is described in the herein.

Clinical and Environmental Samples.

Normal human whole blood samples were obtained from Bioreclamation (Westbury, N.Y.). Cultured bacteria were spiked into blood samples at different concentrations. The MolYsis Complete-5 kit was used to isolate and extract the bacterial genomic DNA from human blood. Cultured bacteria were spiked into samples of water from the Charles River (Boston, Mass.). The spiked water samples were sonicated to release and fragment genomic DNA for direct detection via a single molecule array assay without any further sample pre-treatment.

Results and Discussion

Method for Detecting Double-Stranded DNA Using a Single Molecule Array Assay.

Figure 9:
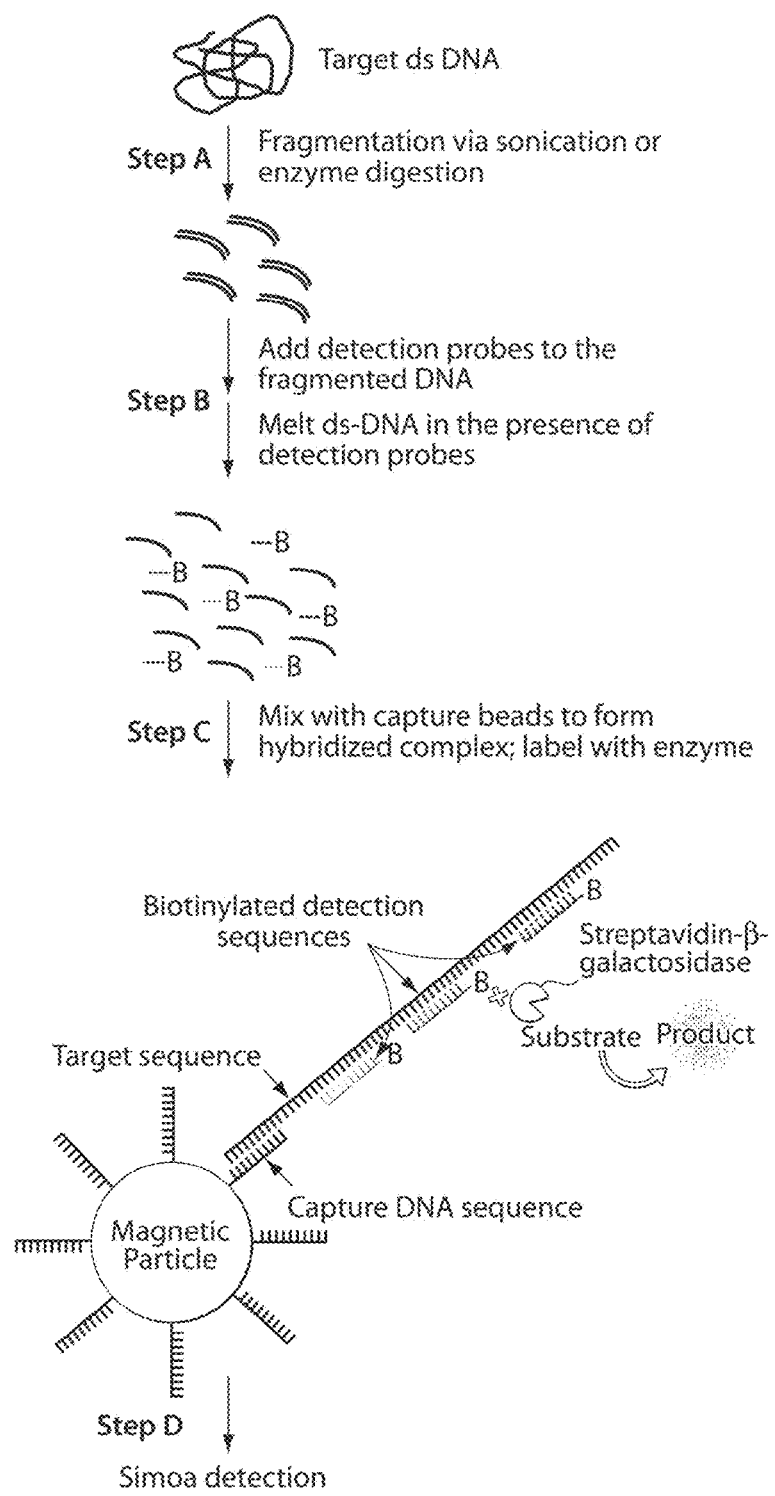
FIG. 9 provides a schematic of a process for the direct detection of genomic, double-stranded DNA using a single molecule assay, according to some embodiments.

FIG. 9 shows the process for detecting ds-DNA using a single molecule array assay. This process involves: a) the conversion of genomic DNA in a sample to a form—short, single-stranded fragments of DNA—that is suitable for detection by a single molecule array assay; and b) the capture, labeling, and detection of these fragments using a single molecule array assay. First, sample preparation is performed to isolate the DNA for further processing (e.g., removal of red and white blood cells). Second, the large ds-DNA (kilobase pairs (kbp) to megabase pairs (Mbp)) are fragmented into shorter strands of ds-DNA (<1,000 bp, and typically 200-800 bp) (step A in FIG. 9). Fragmentation is achieved using either restriction enzymes that generate well-defined fragments depending on the target sequence, or physical fragmentation using sonication that generates more heterogeneous, random fragments. Third, the short ds-DNA strands are converted to short ss-DNA fragments by melting the duplex; this step is performed in the presence of multiple different biotinylated detection probes (step B in FIG. 9). Fourth, the mixtures of ss-DNA fragments and biotinylated detection probes are incubated with paramagnetic beads that present capture probes. The pooled population of capture beads contains 3-4 sub-populations of beads with different sequences that bind to different target sequences. This approach ensures that as many fragmented molecules are captured as possible, especially in the case of random fragmentation where intra-sequence fragmentation occurs. The beads are then washed and incubated with SβG to bind to the detection probes and label the hybridized "sandwich" complex on the beads (step C in FIG. 9). The beads are then washed again, loaded into arrays of femtoliter wells in the presence of enzyme substrate (resorufin-β-D-galactopyranoside; RGP), and single enzyme-labeled molecules or ensembles of molecules are detected using a single molecule array assay (step D in FIG. 9). The images are then analyzed to determine the average number of enzymes per bead (AEB) as described previously (e.g., see Rissin, D. M., Fournier, D. R., Piech, T., Kan, C. W., Campbell, T. G., Song, L., Chang, L., Rivnak, A. J., Patel, P. P., Provuncher, G. K., Ferrell, E. P., Howes, S. C., Pink, B. A., Minnehan, K. A., Wilson, D. H., Duffy, D. C., Simultaneous detection of single molecules and singulated ensembles of molecules enables immunoassays with broad dynamic range. Anal. Chem. 2011, 83, 2279-2285). Each of the steps in this method is described in more detail below.

In FIG. 9: DNA is first fragmented using specific restriction enzymes or via sonication. The fragmented DNA is then mixed with biotinylated detection probes and melted at an elevated temperature to form single-stranded DNA. The ss-DNA-probe mixture is then incubated with paramagnetic beads that present capture DNA probes. Hybridized capture-DNA-detector complexes form on the beads that are then labeled with an enzyme via biotin-streptavidin interaction. These beads are then loaded into arrays of femtoliter wells, and single DNA fragments are detected using a single molecule array assay.

Fragmentation of Ds-DNA (Step a in FIG. 9).

For fragmentation using enzymatic digestion, restriction enzymes were selected to excise from the target DNA molecule a smaller sequence (<400 bp) that contained the binding sites for capture and detection probes. Fragmentation using restriction enzymes generates precisely-defined sequences of intact ds-DNA with narrow distributions of base-pair length, but requires sequence-specific selection and optimization of enzymes for every target. For physical fragmentation, a highly controlled, focused sonication technology was used. By varying the intensity, frequency, and duration of sonication, it is possible to produce random fragments of ds-DNA of reproducible length. Sonication is a generic approach that generates fragments with a relatively broad distribution of base-pair length and a significant fraction of DNA can undergo intra-target fragmentation.

Figure 10A:
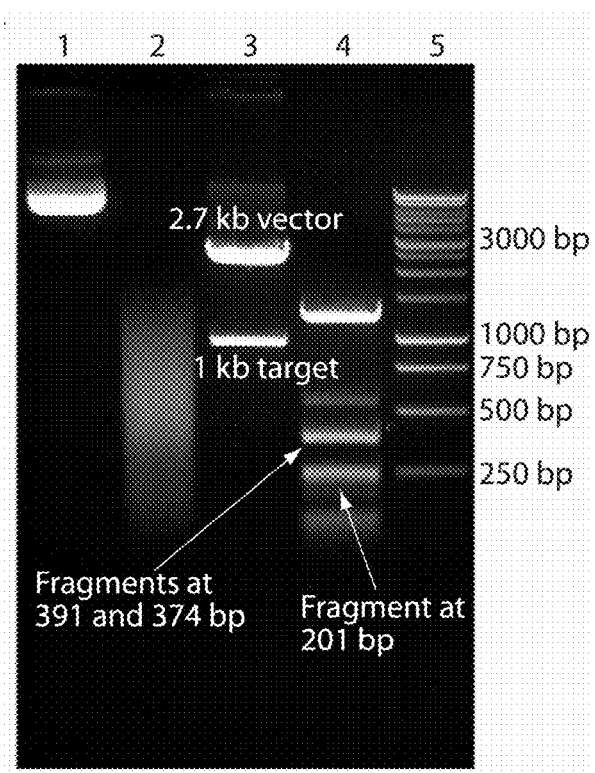
FIG. 10 shows a characterization using gel electrophoresis of fragmentation via sonication and enzymatic digestion of pUC57 plasmid with inserted 966-bp nuc sequence from S. aureus, according to some embodiments.
Figure 10B:
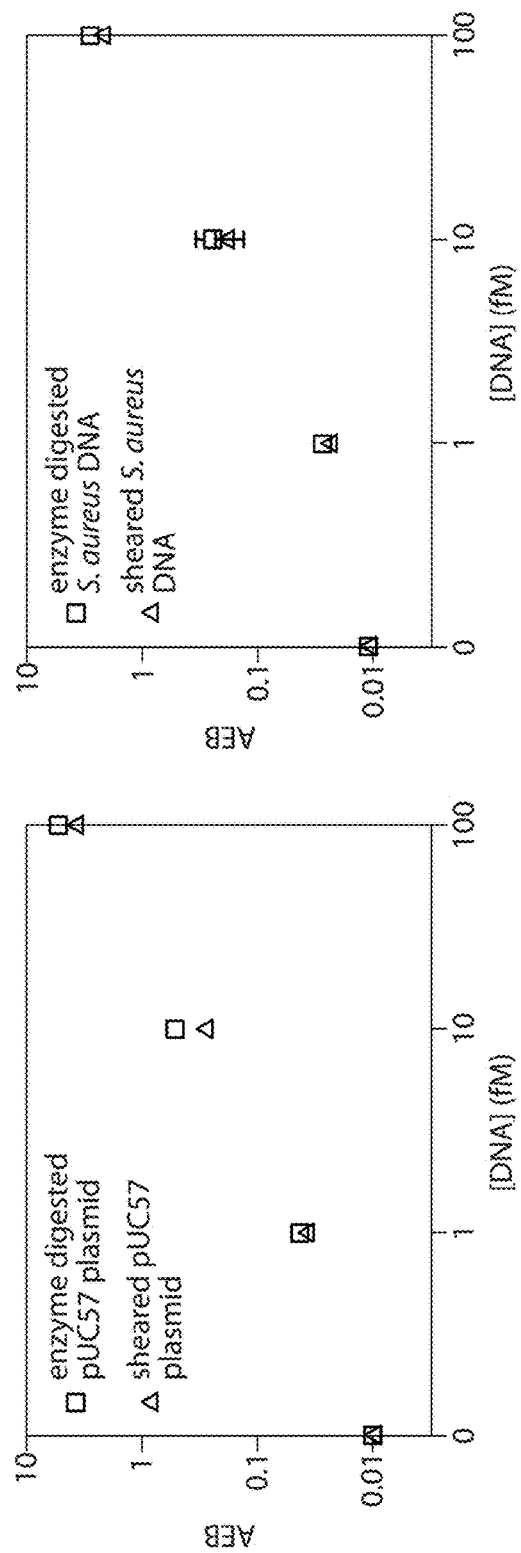

A plasmid construct containing the 966-bp nuc gene from S. aureus (total plasmid size ~3.7 kbp) was created to initially test the two fragmentation approaches. FIG. 10A shows gel electropherograms resulting from fragmenting this plasmid. Both fragmentation methods were highly efficient and very little starting product was observed after fragmentation. While fragmentation was optimized at relatively high concentrations to allow analysis by gel electrophoresis, data generated by the a single molecule array assay showed that it was also efficient at very low concentrations (e.g., see Methods and FIG. 11). Based on these conditions, relatively high concentrations (ng/mL) of both the plasmid and purified genomic DNA from S. aureus (~3 Mbp) was fragmented, diluted these solutions to low concentrations, and detected using the single molecule array assay process shown in FIG. 9. FIG. 10B shows the resulting single molecule array assay data. In general, enzymatic digestion produced single molecule array assay signals that were 10-35% higher than sonication, presumably because of intra-sequence fragmentation using random fragmentation. The use of multiple capture and detection probes (described below), however, reduces the negative impact of random fragmentation. Given the greater complexity of identifying specific restriction enzyme combinations for each target molecule compared to the simplicity of sonication, the latter method may provide improved results as the generic fragmentation method for single molecule array assays. Experiments conducted to optimize sonication showed that distributions centered on fragment sizes that were large enough to contain both capture and detection probes of the target sequence had the highest signals (e.g., see Methods and FIG. 12).

In FIG. 10: Lane 1: Unfragmented pUC57 plasmid with inserted 966-bp nuc sequence; Lane 2: plasmid fragmented via sonication; Lane 3: plasmid digested with EcoRI and XhoI, giving ~1,000 bp product and the vector of pUC57; Lane 4: plasmid digested with EcoRI, XhoI, and AluI, giving three fragments with defined sizes (391, 374, and 201 bp) as indicated, and other fragments digested from the vector by AluI; and, Lane 5: DNA ladder. The conditions used for enzymatic digestion were according to the instruction from the manufacturer (New England Biolab, Inc.); B) single molecule array assay detection of pUC57 plasmid DNA target (left) and genomic DNA of S. aureus (right) fragmented using sonication and restriction enzymes. As with all figures presented here, error bars are shown and represent one standard deviation over triplicate measurements. In cases where error bars are not visible, they are smaller than the symbol. The zero concentration or background signal is plotted on the intercept with the y-axes.

Melting of Fragmented Ds-DNA and Binding to Biotinylated Detection Probes (Step B in FIG. 9).

Figure 13:
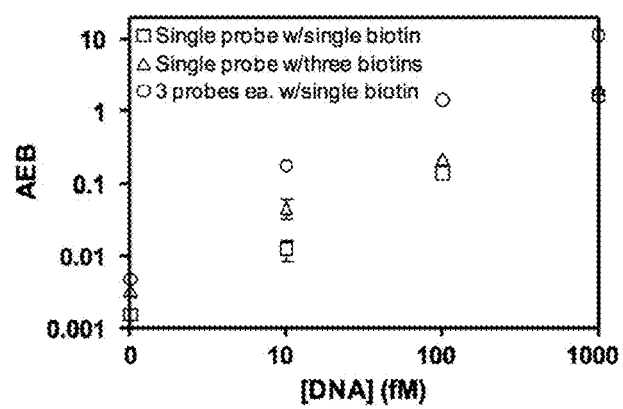
FIG. 13 shows plots of AEB against concentration of plasmid DNA that was fragmented using restriction enzymes, and measured by a single molecule assay using three different approaches to the detection probe, according to some embodiments.

Once ds-DNA was fragmented, the sample was heated at 95° C. to melt the two chains of the duplex apart and minimize secondary structures to enable the binding of ss-DNA to detection and capture probes. To minimize the chance of ss-DNA from rebinding to its complementary strand after melting, the detection probes were combined—which are present at much higher concentrations than the target molecules themselves—with the sample during melting. In some cases, the capture probes were included in the melting step, but this can lead to increased assay backgrounds, possibly due to desorption of blocking proteins from the beads at 95° C. Based on the observation from digital ELISA that having multiple biotin groups on the detection antibody increases the single molecule array assay signal, two strategies were tested for labeling the target DNA with multiple biotins: the use of a single detection probe with multiple biotins, and multiple detection probes each with a single biotin. FIG. 13 shows the single molecule array assay signals from these two approaches compared to a single detection probe containing a single biotin. The multiple probes with single biotins resulted in improvements in sensitivity, greater than the fold-increase in the number of biotins; the single probe with multiple biotins resulted in only modest increases in single molecule array assay signals. Therefore, the use of multiple probes with single biotins may have reduced any steric hindrance for the enzyme labels to bind to the detection probes, and the labeling efficiency by enzyme may not be purely determined by "biotin concentration". Further experiments using >3 probes (FIG. 14) and branched DNA probes presenting very large numbers of biotin groups (data not shown) did not significantly increase single molecule array assay signals.

In FIG. 13: Plot of AEB against concentration of plasmid DNA that was fragmented using restriction enzymes, and measured by single molecule array assay using three different approaches to the detection probe. The same capture beads were used for all three conditions, and the hybridized complex was formed using the same total probe concentrations of: a single detection probe labeled with a single biotin (squares); a single detection probe labeled with three biotins (triangles); or a mixture of three detection probes each labeled with a single biotin (circles). These data were obtained using a single capture probe and multiple detection probes for a 152-bp fragment of the nuc gene from S. aureus inserted into plasmid (Table 1).

Figure 14:
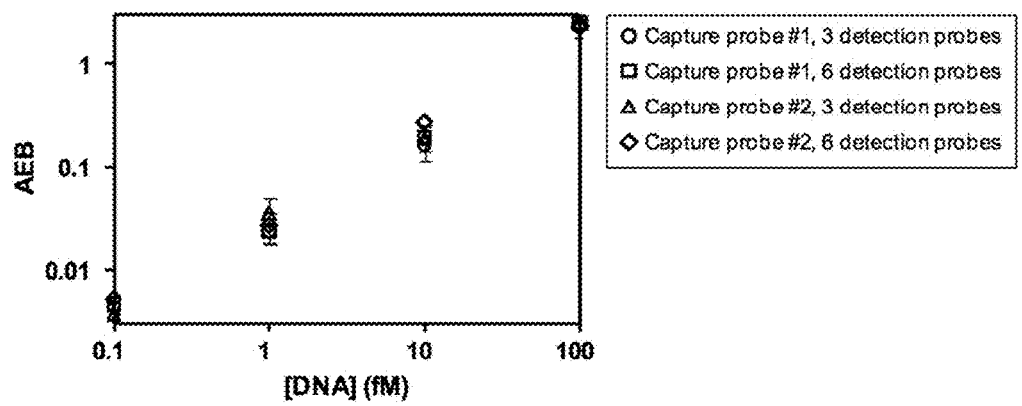
FIG. 14 shows plots of AEB against concentration of plasmid DNA, fragmented using restriction enzymes, and measured by a single molecule assay using different combinations of capture and detection probes, according to some embodiments.

In FIG. 14: Plots of AEB against concentration of plasmid DNA, fragmented using restriction enzymes, and measured by single molecule array assay using different combinations of capture and detection probes. Two different capture probes were tested, and the signals using 3 or 6 detection probes pair with each capture probe were evaluated. The single molecule array assay signals for 3 and 6 detection probes were almost identical. Capture and detection probes were designed for the 966-bp nuc target sequence from S. aureus that was inserted into plasmid (Tables 2 and 3). Single capture beads (S. au Cap-1 or S. au Cap-2) were used for capturing the digested target molecules. For capture bead S. au Cap-1, detection probes S. au Det-1, 2, and 3 or S. au Det-1, 2, 3, 4, 5, and 6 were used; for capture bead S. au Cap-2, detection probes S. au Det-7, 8, and 9 or S. au Det-7, 8, 9, 10, 11, and 12 were used.

Hybridization to Capture Beads and Enzyme Labeling of Captured Ss-DNA (Step C in FIG. 9).

Figure 15:
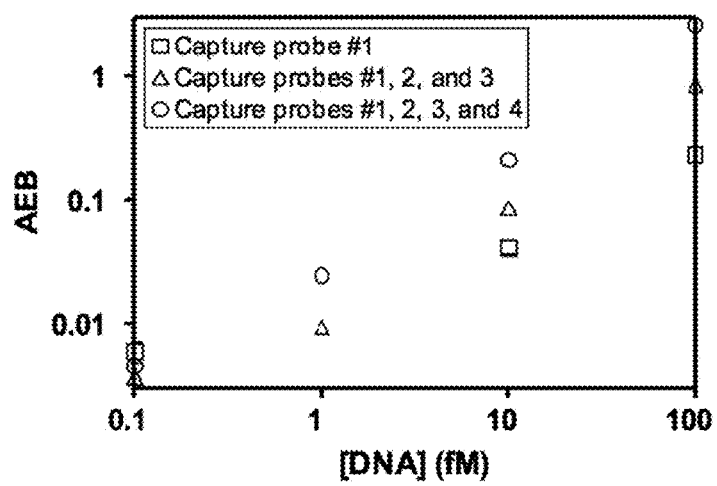
FIG. 15 shows plots of AEB against concentration of genomic DNA that was purified from S. aureus, fragmented using sonication, and measured by a single molecule assay using three different combinations of capture probes, according to some embodiments.

To increase the efficiency of capturing the target DNA—especially for sonicated DNA that undergoes intra-target fragmentation—the use of multiple capture beads was investigated. This approach essentially makes multiple short DNA sequences available for each target within a single molecule of DNA, and FIG. 15 shows that it provides a multiplicative increase in signal. In some cases, the signal did not increase linearly with the number of subpopulations of capture beads used, presumably because of differing binding affinities of different pairs of capture and detection probes. This approach is fruitful, but may be offset by potential reductions in specificity by using multiple capture probes. Special care, therefore, was taken to ensure that each capture probe set was specific for the target organism.

Figure 16:
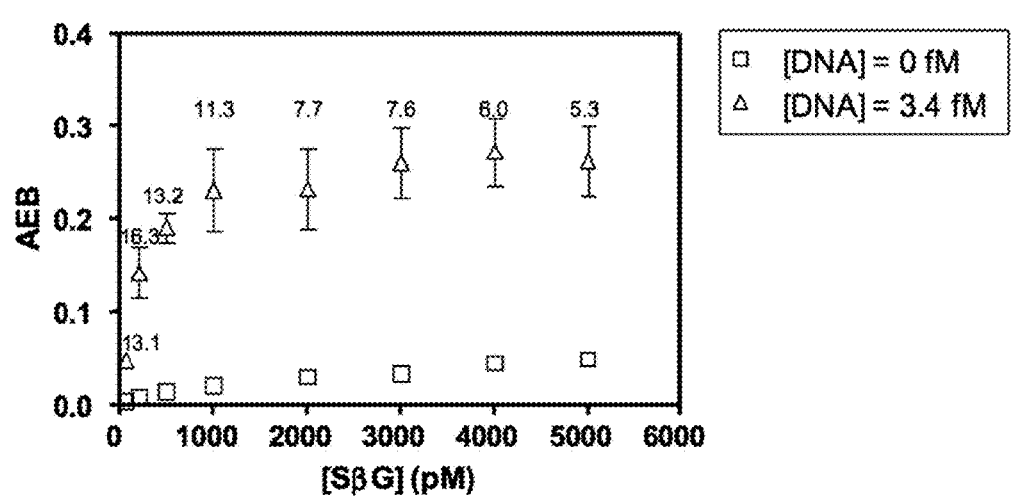
FIG. 16 show plots of AEB against concentration of streptavidin-beta-galactosidase (SβG) enzyme conjugate for plasmid DNA, fragmented using restriction enzymes, and measured by a single molecule assay at DNA concentrations of 3.4 fM (triangles) and 0 fM (squares), according to some embodiments.

Another way to increase single molecule array assay signals is to increase the efficiency of labeling with the enzyme conjugate SβG. While specific signals increase with greater labeling efficiency, the benefits may be offset by increases in background due to non-specific binding of enzyme conjugate to the beads in the absence of specifically bound target DNA. FIG. 16 shows the specific and background single molecule array assay signals as a function of [SβG]; a SβG concentration of 200 pM produced the best signal-to-background ratio for the single molecule array DNA assay described in this example. As the units of the measurement are average enzymes per bead and the number of beads in the assay is known, it is possible to determine the number of molecules captured and labeled in these experiments, and determine the overall efficiency of the single molecule array DNA assay. Based on the "saturated" AEB signals in FIG. 16 using 500,000 beads, the maximum capture and labeling efficiency was calculated to be ~50%. These data indicate that the capture and detection efficiency of single DNA molecules is high using the described single molecule array assay, and that sensitivity may be limited by the non-specific background from enzyme binding to beads in the absence of target rather than the intrinsic sensitivity to single molecules.

In FIG. 16: Plots of AEB against concentration of SβG enzyme conjugate for plasmid DNA, fragmented using restriction enzymes, and measured by single molecule array assay at DNA concentrations of 3.4 fM (triangles) and 0 fM (squares). The signal-to-background ratios (i.e., the ratio of AEB for DNA at 3.4 fM and 0 fM) are indicated above the symbol for the 3.4 fM data; the highest signal-to-background ratio (16.3) was observed at [SβG]=200 pM. These data were obtained using a single capture probe and multiple detection probes for a 152 bp fragment of nuc from S. aureus inserted into plasmid (Table 1).

Analytical Sensitivity of a Single Molecule Array Assay to ds-DNA.

Figure 17:
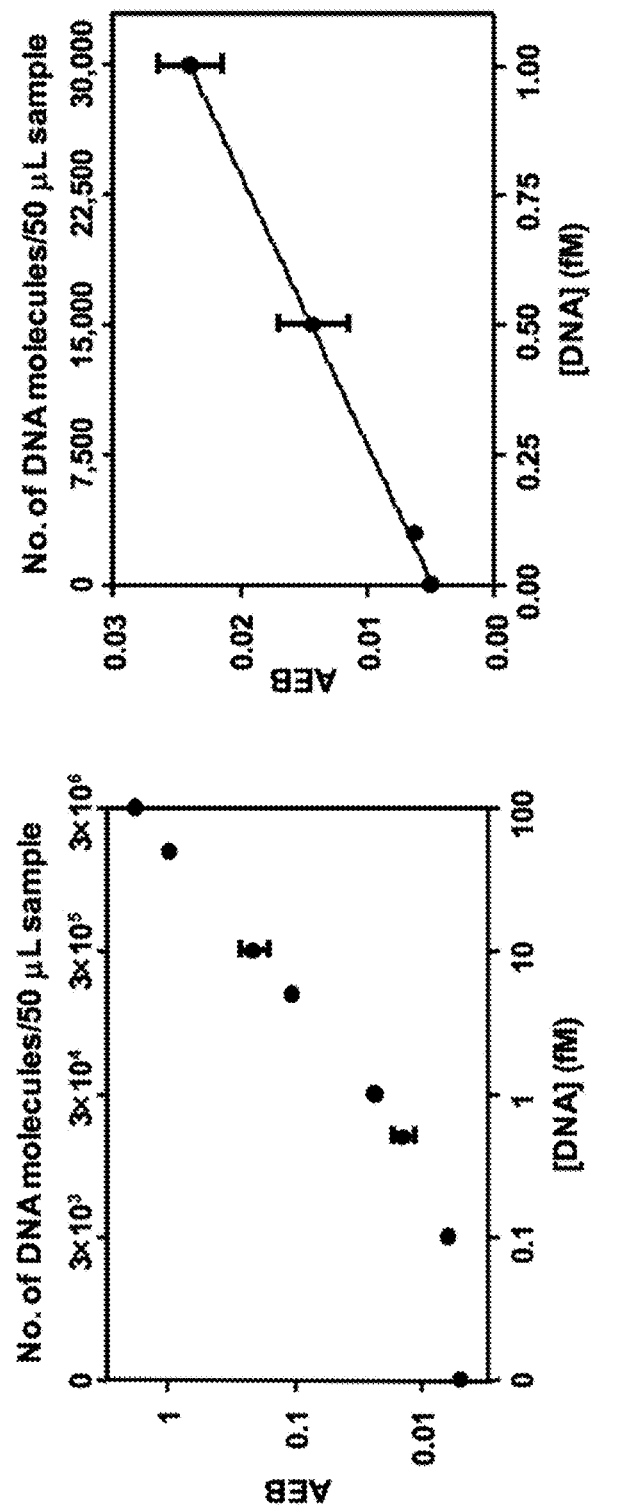
FIG. 17 shows plots of AEB against concentration of genomic DNA that was purified from S. aureus, fragmented using sonication, and measured by a single molecule assay using four subpopulations of different capture probes, according to some embodiments.
Figure 18:
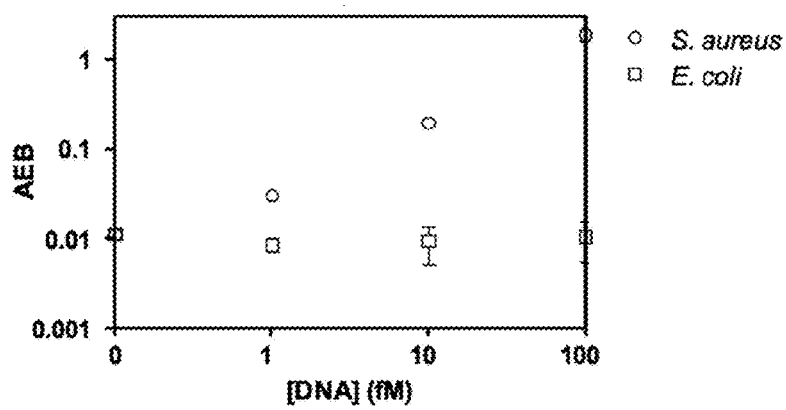
FIG. 18 shows plots of AEB against concentration of DNA that was purified from S. aureus (circles) or E. coli (squares), fragmented using sonication to yield a fragment distribution centered on 800 bp, and detected using a single molecule assay, according to some embodiments.

Based on the optimized single molecule array assay DNA assay described, calibration curves were generated for genomic DNA purified from S. aureus spiked into buffer and fragmented via sonication to determine the LOD; FIG. 17 shows a typical calibration curve. The LOD—determined by interpolating the concentration at signals that are three times the standard deviation above background—in this run was 0.04 fM, or 1,200 molecules of genomic DNA in a 50 μL sample (that is subsequently diluted 2-fold in hybridization buffer for testing in the single molecule array assay). Over eight such calibration curves, the LODs ranged from 0.004-0.16 fM (mean=0.07 fM), or 120-4,800 molecules (mean=2,100 molecules) of DNA per 50 µL sample, depending on the coefficient of variation (CV) of the background (0.2-14%). As a preliminary test for cross-reactivity with other bacteria, DNA from *Escherichia coli* (*E. coli* K-12, ATCC No. 29425) up to 1 pM was spiked and no increase was observed in the single molecule array assay signal above the background AEB. FIG. 18 shows calibration curves run for DNA from *S. aureus* and *E. coli* that demonstrate the specificity of the assay for *S. aureus*.

In FIG. 17: Plots of AEB against concentration of genomic DNA that was purified from *S. aureus*, fragmented using sonication, and measured by single molecule array assay using four subpopulations of different capture probes (Table 2). The data are plotted in log-log space across the concentration range tested (left), and in linear-linear space at subfemtomolar concentrations (right). 125,000 beads presenting each capture probe were used, for a total of 500,000 beads per 100 uL (microliter) test solution. 15 detection probes, each with biotin at the 3' end and each at 0.5 nM, were used (Table 3). The LOD in this experiment was 0.04 fM, or 1,200 DNA molecules per 50 uL sample.

In FIG. 18: Plots of AEB against concentration of DNA that was purified from *S. aureus* (circles) or *E. coli* (squares), fragmented using sonication to yield a fragment distribution centered on 800 bp, and detected using a single molecule array assay. These data were obtained using 4 capture and multiple detection probes for the nuc sequence in the genomic DNA of *S. aureus* (Tables 2 and 3).

To further compare the sensitivity of the methods, a direct comparison of a single molecule array assay with real time PCR (RT-PCR) was performed using the same gene target and DNA samples. Table 4 shows the design of the primers and probes using RT-PCR to detect nuc in *S. aureus*, and Table 5 shows the data from a representative RT-PCR run. The LODs of several RT-PCR experiments were 0.5-1 fM, corresponding to 1,200-2,400 molecules of DNA per 4 µL sample. Further optimization of the choice of primers and thermocycling conditions may result in improvements in the sensitivity of the RT-PCR assay. That said, as an initial comparison under comparable conditions, the sensitivity of the described single molecule array assay compares favorably to an unoptimized RT-PCR assay.

Detection of *S. aureus* in Whole Blood and River Water Using a Single Molecule Array Assay.

To demonstrate the potential use of the single molecule array DNA assay for clinical testing and environmental monitoring, single molecule array assays for the detection of *S. aureus* bacteria in human whole blood and river water were developed. The sensitive detection of *S. aureus* in blood is important in diagnosing bloodstream infections, allowing for early treatment of sepsis that causes 6% of deaths in the US. The presence of coliform bacteria in environmental water is indicative of fecal contamination of drinking water, and sensitive detection of these bacteria is needed as an alternative to culture methods that can take 1-2 days to perform.

Figure 19A:
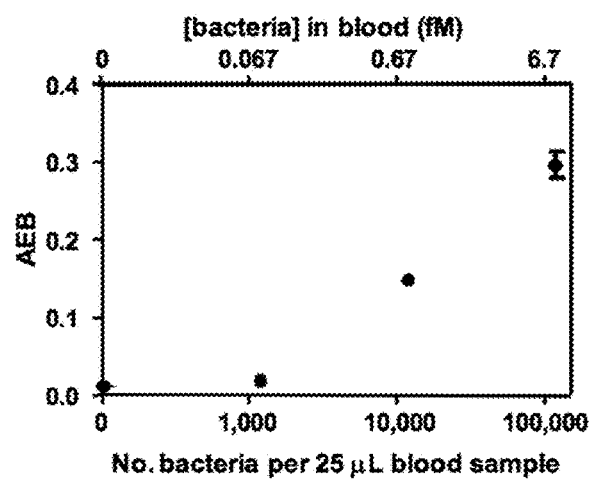
FIG. 19 shows plots of AEB against number of S. aureus bacteria that were spiked into: A) 25 uL whole blood from a human, and, B) 50 uL of water from the Charles River, and then detected using the a single molecule DNA assay, according to some embodiments.

For detection of bacteria in whole blood, a commercially-available purification kit was used to remove the large excess of human DNA while retaining the purified bacterial DNA (see Experimental Section). FIG. 19A shows data obtained from samples in which *S. aureus* bacteria were spiked at different concentrations into whole blood and then detected using the single molecule array assay. Over nine experiments, the average LOD was 1,100 bacteria per 25 µL of whole blood—ranging from 396 to 2,870 bacteria per sample—equivalent to 0.074 fM (range 0.026 to 0.19 fM). In some cases, a short blood culture period (~1 h based on a doubling time of 24 min for *S. aureus*) may be employed for all clinical samples to be detected, enabling a methods that require 24-48 hours.

Figure 19B:
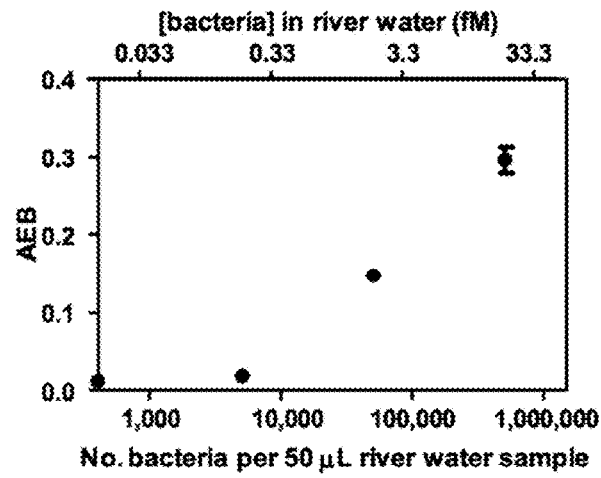

For detection in river water (FIG. 19B), no additional sample preparation steps were performed to the process shown in FIG. 9, except a centrifugation step to remove particulates after sonication. The LOD for bacteria spiked into water from the Charles River was 1,300 bacteria per 50 µL sample, or 0.042 fM. Concentrations of >500 cfu/mL represent unsatisfactory levels of bacteria in river water; converting cfu/mL to [DNA] this level would correspond to 0.83 fM of genomic DNA, making the described single molecule array assay a suitable technology for earlier and faster detection of contamination during a sewage runoff event.

In FIG. 19: Plots of AEB against number of *S. aureus* bacteria that were spiked into: A) 25 uL whole blood from a human, and, B) 50 uL of water from the Charles River, and then detected using the single molecule array DNA assay. For A), 25 uL of whole blood was diluted 2-fold in PBS, and bacterial DNA was extracted using a purification kit that removed human DNA; the purified DNA was then detected as in FIG. 1 using sonication to fragment and a further 2-fold dilution in hybridization buffer to 100 uL. In B), bacteria in 50 uL of river water were detected as outlined in FIG. 1 with an additional centrifugation after sonication, i.e., with no DNA extraction. In both cases, 125,000 beads each presenting 4 capture probes were used (Table 2), for a total of 500,000 beads per 100 uL test solution. 15 detection probes, each with biotin at the 3' end and each at 0.5 nM, were used (Table 3). The LODs in these experiments were: A) 0.026 fM, or 396 DNA molecules per 25 uL of whole blood sample; and, B) 0.042 fM, or 1,271 DNA molecules per 50 uL sample of river water.

Conclusions

These examples indicate that the described single molecule array assays may be employed for the sensitive detection of genomic DNA in complex samples. The process of DNA fragmentation, melting, capture, and labeling is highly efficient, making the described single molecule array assays a highly sensitive DNA assay. The use of both multiple detection probes with single biotins to ensure efficient enzyme labeling, and the use of multiple capture probes to efficiently capture fragmented DNA were important developments in generating a highly sensitive assay.

The described single molecule array DNA assay represents a complementary approach to methods based on amplification using polymerases, such as PCR, and can be employed in situations where PCR is deficient. For example, the single molecule array assays were shown to directly detect low concentrations of DNA in river water without purification, in contrast to amplification methods that require purified DNA to avoid inhibition by interfering substances. The described single molecule array assays also directly measure the target molecules without molecular replication so is less prone than PCR to false positive signals from non-target molecules. The described single molecule array assays also have the benefits of assay simplicity and automation offered by a binding assay. Furthermore, the sensitivities of the assays developed here indicate that the described single molecule array assays would be suitable for measuring bacteria in river water to detect fecal contamination and for the rapid detection of bloodstream infections.

Additional Experimental Details:

Sequence Information for Target DNA Molecules in Single Molecule Array Assays.

Three forms of DNA were tested in this work: plasmid with a short sequence (152 bp) from the nuc gene of *Staphylococcus aureus* (*S. aureus*) inserted into it; plasmid with the entire nuc gene (966 bp) from *S. aureus* inserted; and, genomic DNA from *S. aureus*, either purified or tested directly in the bacteria. The sequences of the target, capture, and detection probe sequences for the three forms of DNA are provided below.

152-Bp Gene Fragment Target in Plasmid.

For initial proof of concept, a 152-bp long sequence was inserted into pcDNA 3.1(−) plasmids as target. The sequence of the inserted 152-bp target was:

```
                                            (SEQ ID NO: 1)
5' TCAGAGAATTC AACTAAAAAG AAAGAGGTGT

TAGTTATGAC AGAATACTTA TTAAGTGCTG GCATATGTAT

GGCAATTGTT TCAATATTAC TTATAGGGAT GGCTATCAGT

AATGTTTCGA AAGGGCAATA CGCAAAGAGG GGATCCAATCA 3'
```

The sequences of the capture and detection probes used to detect the 152 bp sequence in plasmid are provided in Table 1.

966-Bp Gene Target in Plasmid and Genomic DNA.

To detect genomic DNA from *S. aureus* using a single molecule array assay, capture and detection probes for the nuc gene from *S. aureus* were designed. This sequence was also cloned into pUC57-Kan plasmids. The sequence of this gene target and cloned amplicon is as follows:

Materials.

DNA capture and detection probes were obtained from Integrated DNA Technologies. Saline-sodium citrate (SSC), 1-ethyl-3-(3-dimethylaminopropyl) carbodiimide (EDC), N-hydroxysuccinimide (NHS), and solutions of 10% BSA were all obtained from Thermo Scientific. Ultrapure distilled water, ethylenediaminetetraacetic acid (EDTA), and pre-cast agarose gels were purchased from Life Technologies. Tween-20, Triton 100-X, Tris (hydroxymethyl) aminomethane, and 2-(N-morpholino) ethanesulfonic acid (MES) were from Sigma. Dextran sulfate (50% solution) was purchased from Millipore. 2.7-μm-diam., carboxyl-functionalized paramagnetic beads were obtained from Agilent Technologies. All restriction enzymes were purchased from New England Biolabs. The other materials used to perform the single molecule array assays have been described previously (e.g., see Rissin, D. M., Kan, C. W., Campbell, T. G., Howes, S. C., Fournier, D. R., Song, L., Piech, T., Patel, P. P., Chang, L., Rivnak, A. J., Ferrell, E. P., Randall, J. D., Provuncher, G. K., Walt, D. R., Duffy, D. C. Single-molecule enzyme-linked immunosorbent assay detects serum proteins at sub-femtomolar concentrations. Nat. Biotechnol. 2010, 28, 595-599).

Preparation of Capture Beads Presenting DNA Sequences.

500 μL of paramagnetic beads (containing approximately $1.5 \times 10^9$ beads) were first washed with 0.01 M NaOH three times, followed by distilled water for three times. To activate the beads, solutions of 500 μL of 50 mg/mL NHS and 500 μL of 50 mg/mL EDC were prepared freshly in 25 mM MES buffer (pH 6.0), added to the bead pellets, mixed, and incubated for 30 min at room temperature. After activation, the beads were washed twice with cold MES buffer (25 mM,

```
                                                           (SEQ ID NO: 2)
  1    TGTCTCGATA TGATAGTCTG CAACGATTCA TGTTGTAGGC TATTTAATTT TACAAATAAG

61    GCTAAATATA TAAGTTCTGA CACCTAAAAT ATAGAAAATA CATAAAAGTA AGTATAGTTA

121    TTTTATTATA ATTATTAAAT TTTTATTAAT TAATTGTAAA AATGTAGAAT TATAATTAAT

181    TAACGTTTAA TATTAAAATT AACTAAAAAG AAAGAGGTGT TAGTTATGAC AGAATACTTA

241    TTAAGTGCTG GCATATGTAT GGCAATTGTT TCAATATTAC TTATAGGGAT GGCTATCAGT

301    AATGTTTCGA AAGGGCAATA CGCAAAGAGG TTTTTCTTTT TCGCTACTAG TTGCTTAGTG

361    TTAACTTTAG TTGTAGTTTC AAGTCTAAGT AGCTCAGCAA ATGCATCACA AACAGATAAC

421    GGCGTAAATA GAAGTGGTTC TGAAGATCCA ACAGTATATA GTGCAACTTC AACTAAAAAA

481    TTACATAAAG AACCTGCGAC TTTAATTAAA GCGATTGATG GTGATACGGT TAAATTAATG

541    TACAAAGGTC AACCAATGAC ATTCAGACTA TTATTGGTTG ATACACCTGA AACAAAGCAT

601    CCTAAAAAAG GTGTAGAGAA ATATGGTCCT GAAGCAAGTG CATTTACGAA AAAAATGGTA

661    GAAAATGCAA AGAAAATTGA AGTCGAGTTT GACAAAGGTC AAAGAACTGA TAAATATGGA

721    CGTGGCTTAG CGTATATTTA TGCTGATGGA AAAATGGTAA ACGAAGCTTT AGTTCGTCAA

781    GGCTTGGCTA AAGTTGCTTA TGTTTACAAA CCTAACAATA CACATGAACA ACATTTAAGA

841    AAAAGTGAAG CACAAGCGAA AAAAGAGAAA TTAAATATTT GGAGCGAAGA CAACGCTGAT

901    TCAGGTCAAT AATGCTCATT GTAAAGTGT CACTGCTGCT AGTGGCACTT TTATAATTTT

961    TAGATC
```

All capture and detection probes used to detect this sequence in genomic DNA and plasmids are provided in Tables 2 and 3, respectively.

pH 5.0). The capture DNA probes modified with amino groups at 5' end were diluted in a solution containing 50 mM phosphate buffer, 0.5 M NaCl and 0.1% Tween-20 (pH 7.4), and added to the activated beads. The beads were incubated with the DNA probes for 3 h at room temperature and washed with PBS and 1% Tween-20 (pH 7.4). The remaining activated carboxyl groups were then quenched by incubating the beads with 100 mM Tris-HCl (pH 7.4) for 1 h, followed by blocking with 1% BSA in PBS for 1 h. The beads were then washed three times with PBS and 1% Tween-20 (pH 7.4) and stored in the bead storage buffer (50 mM Tris-HCl, 150 mM NaCl, 10 mM EDTA, 0.1% Tween-20, and 1% BSA) at 4° C.

Detection Using Real-Time PCR.

Detection of the nuc gene from *S. aureus* was performed using the Taqman Real-Time PCR assay (Life Technologies). Genomic DNA isolated from *S. aureus* was serially diluted and used as template in RT-PCR reactions containing 1× Taqman Universal PCR Master Mix (Life Technologies), 1× Taqman Exogenous Internal Positive Control (Life Technologies), 200 nM of forward and reverse primers, and 200 nM of fluorescent probes. The sample volume was 4 µL and the total reaction volume was 20 µL. Reactions were performed on Applied Biosystems 7900HT fast Real-Time PCR system. Samples were subjected to an initial denaturing period of 5 min at 95° C., followed by 40 cycles of 15 s melting at 95° C., followed by 1 min annealing and extension at 60° C.

Optimization of Fragmentation.

Figure 11:
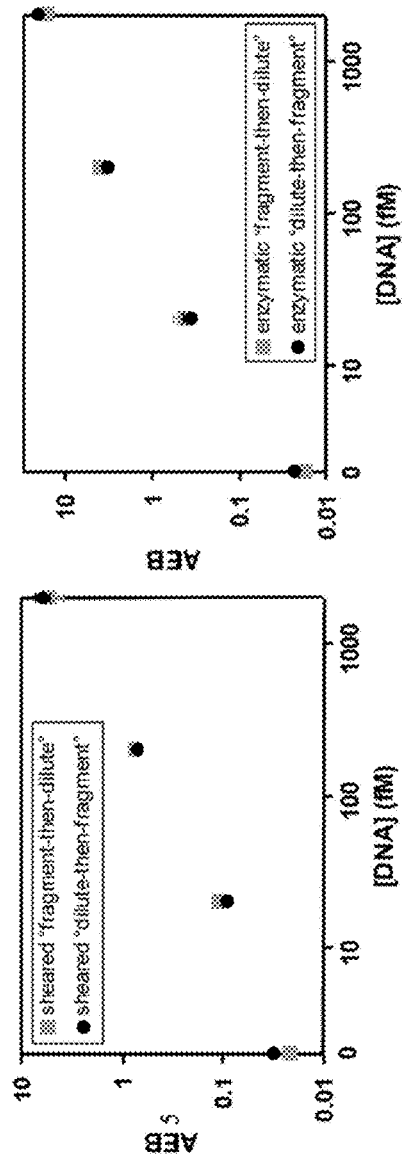
FIG. 11 shows plots of AEB against concentration of plasmid DNA that was fragmented using sonication (left) and restriction enzymes (right), according to some embodiments.

The fragmentation conditions were optimized at relatively high concentrations of ds-DNA (~ng/mL) because gel methods used to characterize the size distribution of fragments are not sensitive at fg/mL levels. These fragmented samples were diluted and a single molecule array assay was used to show high sensitivity at low concentrations of fragments ("fragment-then-dilute") as shown in FIG. 10B. In some embodiments, in a real analytical situation, fragmentation may be efficient at low concentrations, i.e., "dilute-then-fragment" has to work as well as "fragment-then-dilute". Thus, the same fragmentation conditions were applied to DNA samples that were first diluted down to subfemtomolar concentrations. FIG. 11 shows the single molecule array assay data comparing a DNA target tested at femtomolar concentrations by "fragment-then-dilute" and "dilute-then-fragment" approaches; the equivalence in the signal for molecules fragmented at high and low concentrations indicates that that both fragmentation methods are also efficient across the dynamic range.

In FIG. 11: plots of AEB against concentration of plasmid DNA that was fragmented using sonication (left) and restriction enzymes (right), according to a non-limiting embodiment. In both cases, the samples were either fragmented at high concentrations and then diluted before testing ("fragment-then-dilute", squares), or diluted to the concentrations to be tested and fragmented ("dilute-then-fragment", circles). The signals for the two approaches indicate that fragmentation is efficient at low concentrations as well as high. These data were obtained using a single capture probe and multiple detection probes for a 152 bp fragment from nuc in *S. aureus* inserted into plasmid (Table 1).

The effect on the signal produced by the assays on the size of the fragment produced by different fragmentation conditions was examined. For plasmid DNA detected using a single capture sequence over a relatively short sequence (152 bp; Table 1), there was a strong dependence on fragment size, with the strongest signals observed at 200 bp (data not shown). For genomic DNA detected using multiple capture and detection sequences that span a larger sequence (966 bp, Tables 2 and 3), capture efficiency is relatively insensitive to the size of the random fragment produced by sonication (FIG. 12), but fragments close to the length of the target sequence that are covered by both capture and detection probes had the highest signals. The capture and detection probes used to detect the target gene fragment in the genomic DNA of *S. aureus* span ~1,000 bp, and sheared fragments that are 800-1,000 bp long gave higher signals (FIG. 12).

Figure 12:
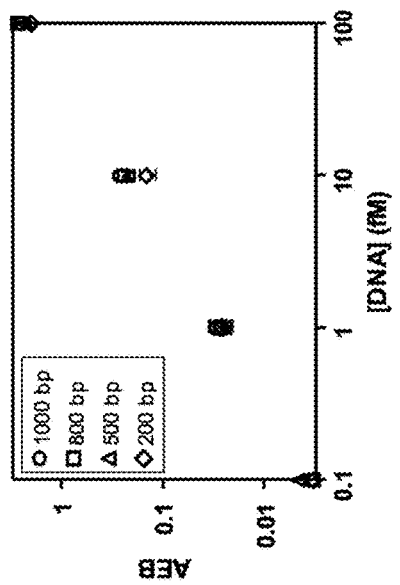
FIG. 12 shows plots of AEB against concentration of DNA that was purified from S. aureus and fragmented using sonication to yield a fragment distribution centered on: 1000 bp (circles); 800 bp (squared); 500 bp (triangles); and, 200 bp (inverted triangles), according to some embodiments.

In FIG. 12: Plots of AEB against concentration of DNA that was purified from *S. aureus* and fragmented using sonication to yield a fragment distribution centered on: 1000 bp (circles); 800 bp (squared); 500 bp (triangles); and, 200 bp (inverted triangles). These data were obtained using multiple capture and detection probes list in Tables 2 and 3, for the 966-bp nuc sequence in the genomic DNA of *S. aureus*.

TABLE 1

Capture and detection probes for the target sequence (152 bp) from nuc that was cloned into pcDNA 3.1 (-) plasmids.

| Probe name | Sequences (5'-3') | Length (bp) | $T_m$ (° C.) | Position in the target sequence | Modification |
|---|---|---|---|---|---|
| Capture 1 | GAAAGGGCAATACGCAAAGAGG (SEQ ID NO: 3) | 22 | 56.6 | 120 | 5'-Amino-C12 |
| Detector 1 | AAAGAAAGAGGTGTTAGTTATGAC (SEQ ID NO: 4) | 24 | 50.8 | 18 | 3'-Biotin-TEG |
| Detector 2 | TAAGTGCTGGCATATGTATGGC (SEQ ID NO: 5) | 22 | 55.1 | 53 | 3'-Biotin-TEG |
| Detector 3 | AGGGATGGCTATCAGTAATGTT (SEQ ID NO: 6) | 22 | 53.4 | 96 | 3'-Biotin-TEG |

TABLE 1-continued

Capture and detection probes for the target sequence (152 bp) from nuc that was cloned into pcDNA 3.1 (-) plasmids.

| Probe name | Sequences (5'-3') | Length (bp) | $T_m$ (° C.) | Position in the target sequence | Modification |
|---|---|---|---|---|---|
| Detector with multiple biotins* | AAAG AAAGAGGT(b)GT T(b)AGTTAT(b)GAC (SEQ ID NO: 7) | 24 | 52.2 | 18 | Multiple biotins |

*Detection probe that was labeled with multiple biotins (b) at the indicated positions along the sequence.

TABLE 2

Capture sequences for detecting the 966 bp sequence from the nuc gene in the genomic DNA of S. aureus and the plasmid construct.

| Probe name | Sequences (5'-3') | Length (bp) | $T_m$ (° C.) | Position in gene | Modification |
|---|---|---|---|---|---|
| S. au. Cap-1 | TGTCTCGATATGATA GTCTGCAACGATTC (SEQ ID NO: 8) | 29 | 60.2 | 1 | 5'-Amino-C12 |
| S. au. Cap-2 | CTCAGCAAATGCATC ACAAACAGATAA (SEQ ID NO: 9) | 27 | 58.1 | 393 | 5'-Amino-C12 |
| S. au. Cap-3 | AACAGATAACGGCGT AAATAGAAGTGGT (SEQ ID NO: 10) | 28 | 59.9 | 411 | 5'-Amino-C12 |
| S. au. Cap-4 | AAGGCTTGGCTAAAG TTGCTTATGTTT (SEQ ID NO: 11) | 27 | 59.3 | 779 | 5'-Amino-C12 |

TABLE 3

Detection sequences for detecting the 966 bp sequence of the nuc gene in the genomic DNA of S. aureus and the plasmid construct.

| Probe name | Sequences (5'-3') | Length (bp) | $T_m$ (° C.) | Position in gene | Modification |
|---|---|---|---|---|---|
| S. au. Det-1 | TTACAAATAAGGCTAAA TATATAAGTTCTGACAC C (SEQ ID NO: 12) | 35 | 58.5 | 50 | 3'-Biotin-TEG |
| S. au. Det-2 | AGAAAATACATAAAAGT AAGTATAGTTATTTTAT TATAATTATTAAATTT (SEQ ID NO: 13) | 50 | 57.4 | 93 | 3'-Biotin-TEG |
| S. au. Det-3 | CTGGCATATGTATGGCA ATTGTTTCAA (SEQ ID NO: 14) | 27 | 58.1 | 248 | 3'-Biotin-TEG |
| S. au. Det-4 | ACTTATAGGGATGGCTA TCAGTAATGTTTCG (SEQ ID NO: 15) | 31 | 60.3 | 279 | 3'-Biotin-TEG |
| S. au. Det-5 | AGGGCAATACGCAAAGA GGTTT (SEQ ID NO: 16) | 22 | 56.9 | 312 | 3'-Biotin-TEG |
| S. au. Det-6 | TTCGCTACTAGTTGCTT AGTGTTAACTT (SEQ ID NO: 17) | 28 | 58.1 | 340 | 3'-Biotin-TEG |
| S. au. Det-7 | AGATCCAACAGTATATA GTGCAACTTCAACT (SEQ ID NO: 18) | 31 | 60.1 | 444 | 3'-Biotin-TEG |
| S. au. Det-8 | AAAGCGATTGATGGTGA TACGGTTAAATTAA (SEQ ID NO: 19) | 31 | 59.9 | 508 | 3'-Biotin-TEG |

TABLE 3-continued

Detection sequences for detecting the 966 bp sequence of the nuc gene in the genomic DNA of S. aureus and the plasmid construct.

| Probe name | Sequences (5'-3') | Length (bp) | $T_m$ (°C.) | Position in gene | Modification |
|---|---|---|---|---|---|
| S. au. Det-9 | GTTGATACACCTGAAAC AAAGCATCCTAAA (SEQ ID NO: 20) | 30 | 60.0 | 577 | 3'-Biotin-TEG |
| S. au. Det-10 | GGTGTAGAGAAATATGG TCCTGAAGCAA (SEQ ID NO: 21) | 28 | 59.9 | 610 | 3'-Biotin-TEG |
| S. au. Det-11 | AATGGTAGAAAATGCAA AGAAAATTGAAGTCG (SEQ ID NO: 22) | 32 | 60.1 | 654 | 3'-Biotin-TEG |
| S. au. Det-12 | ACAAAGGTCAAAGAACT GATAAATATGGACG (SEQ ID NO: 23) | 31 | 59.9 | 692 | 3'-Biotin-TEG |
| S. au. Det-13 | AAACCTAACAATACACA TGAACAACATTTAAGAA A (SEQ ID NO: 24) | 35 | 59.7 | 808 | 3'-Biotin-TEG |
| S. au. Det-14 | ACGCTGATTCAGGTCAA TAATGCTCA (SEQ ID NO: 25) | 26 | 59.8 | 893 | 3'-Biotin-TEG |
| S. au. Det-15 | GTGTCACTGCTGCTAGT GGCAC (SEQ ID NO: 26) | 22 | 60.1 | 927 | 3'-Biotin-TEG |

TABLE 4

Primers and probe for detecting the nuc gene in S. aureus using the real-time polymerase chain reaction (RT-PCR) Taqman assay.

| Oligo name | Sequence |
|---|---|
| Forward Primer | GATACACCTGAAACAAAGCATCC (SEQ ID NO: 27) |
| Reverse Primer | GCCACGTCCATATTTATCAGTTC (SEQ ID NO: 28) |
| Probe | FAM-TGGTCCTGAAGCAAGTGCA TTTACGA-TAMRA (SEQ ID NO: 29) |

TABLE 5

RT-PCR detection of the nuc gene using RT-PCR Taqman assay. 4 μL of sample containing the target DNA (purified genomic DNA from S. aureus) was tested using RT-PCR with a total volume of 20 μL, including an internal positive control nucleic acid.

| Concentration of target DNA (fM) | $C_t$ of Internal Positive Control target | $C_t$ of target DNA | $\Delta C_t$ |
|---|---|---|---|
| 780 (control) | 31.580614 | 20.931849 | −10.648765 |
| 780 (control) | 32.96846 | 23.411776 | −9.556684 |
| 780 (control) | 30.643192 | 20.743279 | −9.899913 |
| 0 | 29.608555 | Not detected | Not determined |
| 0 | 29.800558 | Not detected | Not determined |
| 0 | 29.002045 | Not detected | Not determined |
| 0.001 | 29.050919 | Not detected | Not determined |
| 0.001 | 28.818737 | Not detected | Not determined |
| 0.001 | 28.890617 | Not detected | Not determined |
| 0.001 | 28.647667 | Not detected | Not determined |
| 0.001 | 28.445324 | Not detected | Not determined |
| 0.005 | 29.74572 | Not detected | Not determined |
| 0.005 | 29.107756 | Not detected | Not determined |
| 0.005 | 28.920626 | Not detected | Not determined |
| 0.005 | 28.299974 | Not detected | Not determined |
| 0.005 | 28.511072 | Not detected | Not determined |
| 0.005 | 28.439665 | Not detected | Not determined |
| 0.01 | 29.188345 | Not detected | Not determined |
| 0.01 | 28.835217 | Not detected | Not determined |
| 0.01 | 28.689434 | Not detected | Not determined |
| 0.01 | 28.497839 | Not detected | Not determined |
| 0.01 | 28.643997 | Not detected | Not determined |
| 0.01 | 34.54042 | Not detected | Not determined |
| 0.05 | 28.489883 | Not detected | Not determined |
| 0.05 | 28.53511 | Not detected | Not determined |
| 0.05 | 28.471455 | Not detected | Not determined |
| 0.1 | 28.40064 | Not detected | Not determined |
| 0.1 | 28.483795 | Not detected | Not determined |
| 0.1 | 28.567057 | Not detected | Not determined |
| 0.5 | 27.895206 | Not detected | Not determined |
| 0.5 | 28.692696 | Not detected | Not determined |
| 0.5 | 28.167421 | Not detected | Not determined |
| 1 | 29.027088 | 30.944057 | 1.916969 |
| 1 | 31.221546 | Not detected | Not determined |
| 1 | 28.675608 | 30.486494 | 1.810886 |
| 5 | 28.953087 | 29.147697 | 0.19461 |
| 5 | 29.858126 | 30.308714 | 0.450588 |
| 5 | 28.41846 | 28.127844 | −0.290616 |

TABLE 5-continued

RT-PCR detection of the nuc gene using RT-PCR Taqman assay. 4 μL of sample containing the target DNA (purified genomic DNA from *S. aureus*) was tested using RT-PCR with a total volume of 20 μL, including an internal positive control nucleic acid.

| Concentration of target DNA (fM) | $C_t$ of Internal Positive Control target | $C_t$ of target DNA | $\Delta C_t$ |
|---|---|---|---|
| 10 | 28.888987 | 27.609077 | −1.27991 |
| 10 | 29.995506 | 29.493462 | −0.502044 |
| 10 | 28.296907 | 27.19254 | −1.104367 |
| 50 | 29.486958 | 25.244225 | −4.242733 |
| 50 | 28.267817 | 25.072395 | −3.195422 |
| 50 | 29.014967 | 25.017838 | −3.997129 |
| 100 | 29.12121 | 24.259422 | −4.861788 |
| 100 | 29.002642 | 24.232346 | −4.770296 |
| 100 | 29.455605 | 25.293764 | −4.161841 |

Example 2

The following example describes the preparation and optimization of capture and detection probes for the detection of nine genes from three bacteria.

Two sets of probes, capture and detection probes, were designed for each of nine target genes that included the tuf, fnbA, dfrB genes from *S. aureus*, stx1, stx2, flich7, eae genes from *E. coli*, and cpa, pfoA genes from *C. perfringens*. For each target gene, several capture objects (e.g., beads) were prepared, each presenting a different type of capture probe that targeted at different binding sites along its target gene. For each targeted binding site, multiple biotinylated detection probes were prepared spanning a contiguous sequence. The contiguous sequence was usually downstream of the binding site of capture probe. A non-limiting example of designed capture and detection probes is shown in Table 6 for the stx1 gene from *E. coli*.

TABLE 6

Summary of designed capture and detection probes for the stx1 gene (GI: 215072) from *E. coli*.

| Sequence Length | Quality | Rating score | Probe Sequence | Position | Length | Tm | GC % | Probe assignment |
|---|---|---|---|---|---|---|---|---|
| 1,499 | Best | 87 | GGCGTGGAGGATGTCAAGAATATAGTTAT (SEQ ID NO: 30) | 105 | 29 | 60 | 41.4 | Cpt 1 |
| 1,499 | Best | 79.1 | TGGTGCTCAAGGAGTATTGTGTAATATGAA (SEQ ID NO: 31) | 138 | 30 | 60 | 36.7 | Det 1 |
| 1,499 | Best | 85 | TCAGTTAATGTGGTGGCGAAGGAATT (SEQ ID NO: 32) | 211 | 26 | 60 | 42.3 | Det 2 |
| 1,499 | Good | 62.6 | TGCAAAGACGTATGTAGATTCGCTGA (SEQ ID NO: 33) | 255 | 26 | 59.6 | 42.3 | Det 3 |
| 1,499 | Good | 69.8 | AGGTACTCCATTACAGACTATTTCATCAGG (SEQ ID NO: 34) | 300 | 30 | 59.5 | 40 | Det 4 |
| 1,499 | Best | 77.1 | TCCAGGTACAACAGCGGTTACATTG (SEQ ID NO: 35) | 528 | 25 | 59.9 | 48 | Cpt 2 |
| 1,499 | Good | 62.8 | CGTGTTGCAGGGATCAGTCGTAC (SEQ ID NO: 36) | 583 | 23 | 60 | 56.5 | Det 5 |
| 1,499 | Best | 87.5 | AATCGCCATTCGTTGACTACTTCTTATCT (SEQ ID NO: 37) | 619 | 29 | 60.1 | 37.9 | Det 6 |
| 1,499 | Good | 66.1 | TTAATGTCGCATAGTGGAACCTCAC (SEQ ID NO: 38) | 652 | 25 | 57.8 | 44 | Det 7 |
| 1,499 | Best | 81.1 | GCAGTCTGTGGCAAGAGCGATG (SEQ ID NO: 39) | 681 | 22 | 60.4 | 59.1 | Det 8 |
| 1,499 | Best | 83.8 | GGCGTTCTTATGTAATGACTGCTGAAG (SEQ ID NO: 40) | 788 | 27 | 59.6 | 44.4 | Cpt 3 |
| 1,499 | Best | 87.1 | GGTTGAGTAGCGTCCTGCCTGA (SEQ ID NO: 41) | 842 | 22 | 60.3 | 59.1 | Det 9 |

TABLE 6-continued

Summary of designed capture and detection probes for the stx1 gene (GI: 215072) from *E. coli*.

| Sequence Length | Quality | Rating score | Probe Sequence | Position | Length | Tm | GC % | Probe assignment |
|---|---|---|---|---|---|---|---|---|
| 1,499 | Best | 78.3 | GACAAGACTCTGTTC GTGTAGGAAGAAT (SEQ ID NO: 42) | 872 | 28 | 59.9 | 42.9 | Det 10 |
| 1,499 | Good | 74.7 | GGAAGCGTGGCATTA ATACTGAATTGTC (SEQ ID NO: 43) | 928 | 28 | 60.3 | 42.9 | Det 11 |
| 1,499 | Good | 74.8 | ATCTGATGAGTTTCC TTCTATGTGTCCG (SEQ ID NO: 44) | 987 | 28 | 59.8 | 42.9 | Det 12 |
| 1,499 | Best | 87.5 | AATCTTCAGTCTCTT CTTCTCAGTGCG (SEQ ID NO: 45) | 1,282 | 27 | 59.9 | 44.4 | Cpt 4 |
| 1,499 | Good | 57.1 | GTGGGTGATAAAGAA TTATTTACCAACAGA (SEQ ID NO: 46) | 1,249 | 30 | 57.8 | 33.3 | Det 13 |
| 1,499 | Good | 52 | TTCGTTGACTCAGAA TAGCTCAGT (SEQ ID NO: 47) | 1,382 | 24 | 56.3 | 41.7 | Det 14 |
| 1,499 | Good | 73.4 | AAATAGCAGGCGGAG ATTCATAAATGTTAA (SEQ ID NO: 48) | 1,408 | 30 | 59.3 | 33.3 | Det 15 |
| 1,499 | Best | 81.4 | CATCTCAATTCAGTC AGTTGTTGCCG (SEQ ID NO: 49) | 1,441 | 26 | 59.9 | 46.2 | Det 16 |

Figure 20A:
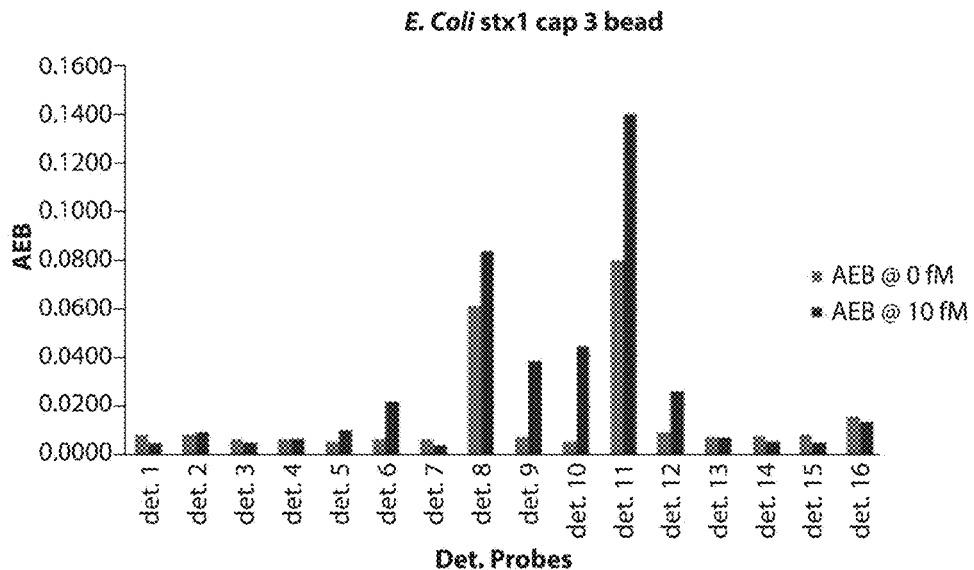
FIG. 20 shows results A) relating to the screening of E. Coli stx1 capture bead-3 with each individual detection probes (16 probes in total) for background interactions and signal responses using a single molecule assay, and B) signal to background ratios (S/B) from each detection probe paired with capture bead-3 at 10 fM of targets (B), according to some embodiments.
Figure 20B:
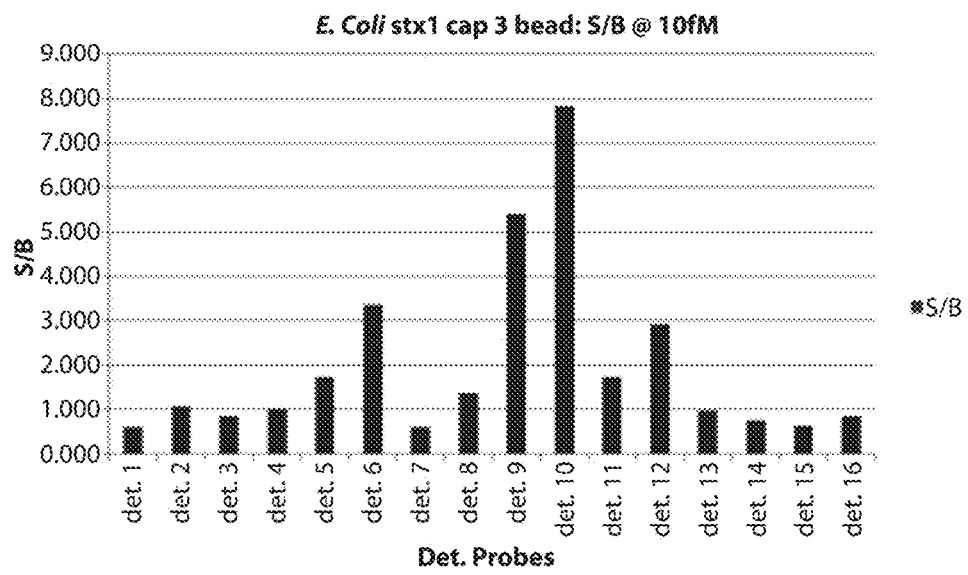

To optimize the single molecule assay for each target gene, the prepared capture beads were first screened with each detection probes individually to determine whether there were any interactions that could lead to non-specific backgrounds in the assay. While capture and detection probes were been tested for heterodimer using software, they could still cross react with each other in the absence of target analytes to give a high assay background. Such elevated background from cross reactions between detection and capture probes could affect detection sensitivity of the assay. As a result, any probes that gave high assay background from initial screening were excluded from use, and remaining capture and detection probes were then further examined for signal responses in the presence of target analytes. Probe pairs that gave no responses or low signals were also excluded for further optimization. FIG. 20 shows an example of high background from capture and detection probe interactions for the Stx1 gene from *E. coli* and different signal responses from screening.

In FIG. 20: Screening of *E. coli* stx1 capture bead-3 with each individual detection probes (16 probes in total) for background interactions and signal responses using a single molecule array assay (A). High background signals were seen from detection probes 7 and 11 and these two probes were excluded from use as detection probes for capture bead-3; Signal to background ratios (S/B) from each detection probe paired with capture bead-3 at 10 fM of targets (B). Based on screening of background and signals, the detection probes (6, 9, 10, and 12) that gave low background and relatively high S/B ratios were chosen for further assay optimization for capture bead-3.

Figure 21A:
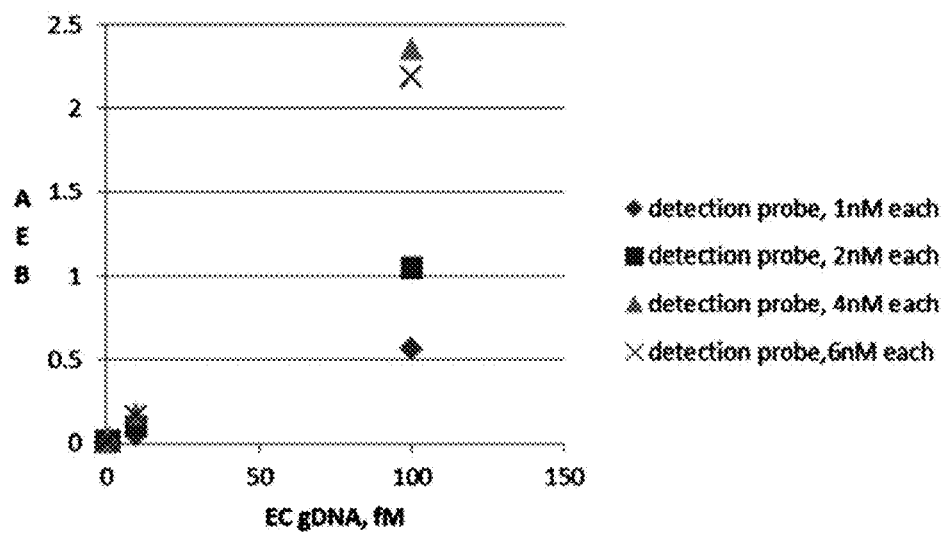
FIG. 21 shows results a) relating to the variation of detection probe concentrations for E. Coli stx1 gene, and b) relating to the S/B ratio observed using a concentration of 4 nM for detection probes, according to some embodiments.
Figure 21B:
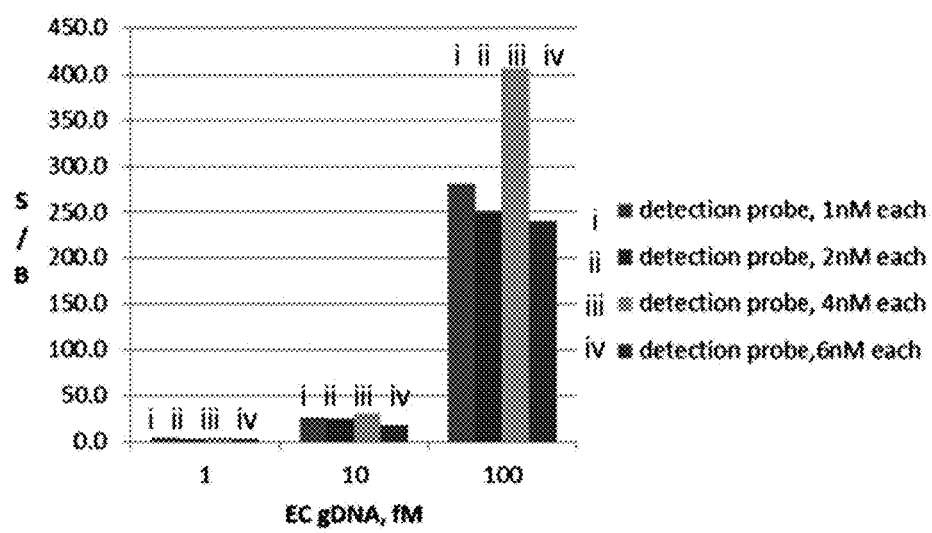

Next, other assay conditions, for example the concentrations of detection probes and enzyme conjugate (Streptavidin-beta-galactosidase, or SbG), were optimized for each selected combination of capture and detection probes from the initial screening of background and signals. FIG. 21 shows the increase of signal responses upon increasing the concentration of detection probes. Generally, the conditions that give high signals and low background, thus the best S/B, were chosen for each target gene in an attempt to achieve the best sensitivity. Table 7 summarized the analytical sensitivity for nine target genes using each optimized capture and detection probes and single molecule array assay conditions.

In FIG. 21: Optimization of detection probe concentrations for *E. coli* stx1 gene, capture bead-1. Four different concentrations (1, 2, 4, and 6 nM) were used for each individual detection probe used for capture bead-1. Signals increased upon increasing the concentration of detection probes and reached plateau at 6 nM (A); the best S/B ratio was seen at a concentration of 4 nM for detection probes, which was chosen as the optimal condition for *E. Coli* stx1 gene, capture bead-1 (B).

TABLE 7

Summary of analytical sensitivity for nine target genes from three bacteria.

| Bacteria | Target genes | Analytical LOD, fM | Analytical LOD, molecules/100 μl |
|---|---|---|---|
| *S. aureus* | Tuf | 0.067 | 4000 |
| | fnbA | 0.059 | 3540 |
| | dfrB | 0.083 | 4960 |

TABLE 7-continued

Summary of analytical sensitivity for nine target genes from three bacteria.

| Bacteria | Target genes | Analytical LOD, fM | Analytical LOD, molecules/100 µl |
|---|---|---|---|
| E. Coli | stx1 | 0.066 | 3936 |
|  | stx2 | 0.036 | 2160 |
|  | flich7 | 0.07 | 4373 |
|  | eae | 0.06 | 3300 |
| C. perfringens | cpa | 0.05 | 2940 |
|  | pfoA | 0.07 | 4308 |

Note:
LOD was calculated using 3 × SD above background signal; the number presented in Table 7 was a mean of multiple runs for each target gene.

Example 3

The following example describes an assay for detection of an RNA virus from Sendai virus with a sensitivity of less than 0.1 fM (or 6000 molecules per 100 µl) target concentration. Sendai virus is a negative sense, single-stranded RNA virus that belongs to the family of Paramyxoviridae with a genome size about 15.3 kb encoding six proteins. Since some of the Viral particles might have truncated genome from N-terminus, the C-terminus L protein was chosen as the target gene for detection. Four capture probes and sixteen detection probes were initially designed, and after screening of background and signals (e.g., as described in Example 2) for each capture bead with all detection probes, one of the capture beads gave the best sensitivity when combined with a pool of all 16 detection probes. The sample of Sendai virus was purchased from Charles River Laboratory, and genomic viral RNA was then extracted and purified using a Qiagen kit following manufacturer's instructions. The purified RNA was quantified using a Bioanalyzer and used as standards during assay development.

Figure 22A:
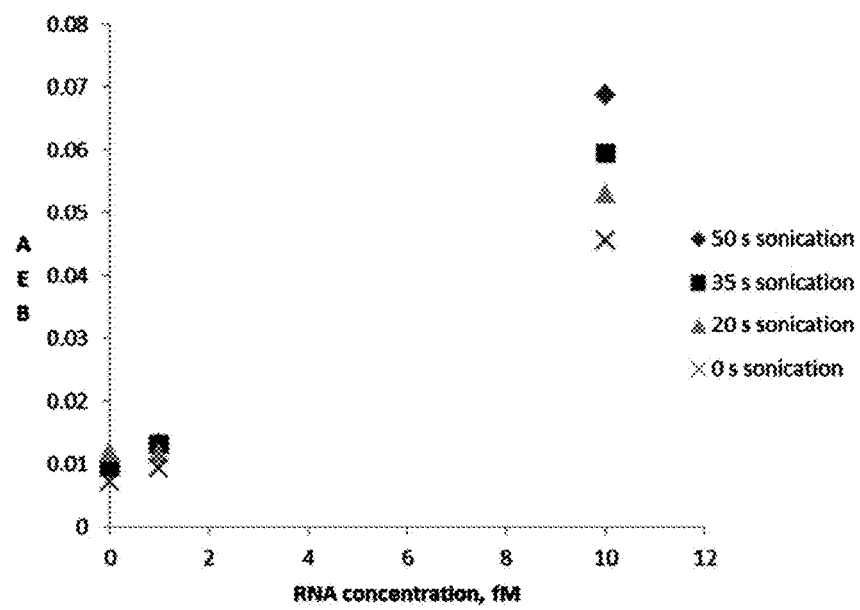
FIG. 22 shows A) a comparison of dose responses of purified RNA at different shearing conditions vs. no fragmentation under the same assay conditions, and B) comparison of pre-assay treatment of RNA samples at two different temperatures for signals, according to some embodiments.
Figure 22B:
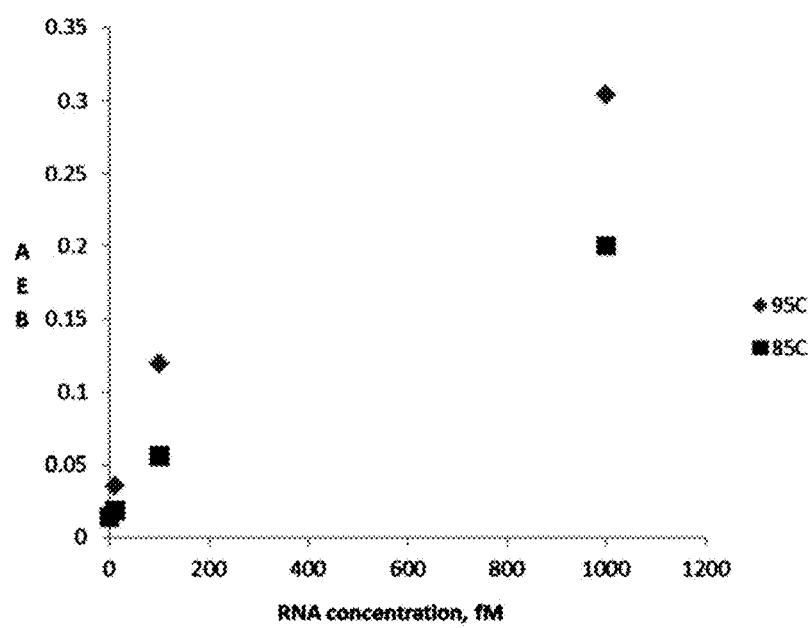

To optimize the detection of viral RNA, no fragmentation vs. fragmentation of the genomic RNA at various sizes was compared. Fragments of the viral RNA at different sizes were obtained by using different sonication time using Covaris AFA technology. FIG. 22A shows the dose-responses of the purified RNA at different shearing conditions. Fragmented RNA gave better signals to non-fragmented genomic RNA, and an optimal condition for sonication was 50 s that generated RNA fragments in the range of 200 to 1000 bp giving the best dose-responses. While the genomic RNA is single-stranded where denaturing is not necessary, heat treatment at 95° C. for 5 min of the fragmented RNA pre-hybridization seemed beneficial for enhanced signals as shown in FIG. 22B, may be due to reduced steric hindrance from secondary structures.

In FIG. 22: Comparison of dose responses of purified RNA at different shearing conditions vs. no fragmentation under the same assay conditions (A); comparison of pre-assay treatment of RNA samples at two different temperatures (85 vs. 95° C.) for signals (B).

Since RNA is very easily degraded that would negatively affect detection sensitivity, one of the challenges developing a single molecule array RNA assay is to maintain the integrity of RNA samples during detection.

To keep RNA intact during the course of assay, a non-protein Rnase inhibitor was included into all buffers during each assay step before the final wash of capture beads with PBS. Significant improvement of signals was observed when including Rnase inhibitor in the assay buffers. Temperature used for hybridization was also optimized for RNA detection. Three different temperatures were tried, and a temperature at 55° C. seemed optimal for RNA hybridization that gave the highest assay signals.

After optimization as described above for selection of capture and detection probes for the target gene, sample preparation, and assay conditions, multiple tests were performed under the optimized conditions for detection of purified viral RNA from Sendai virus. The sensitivity from each run was calculated as shown in Table 8, and an average LOD of 0.05 fM (or 2845 RNA molecules per 100 µl) was obtained using the described single molecule array RNA assays.

TABLE 8

Summary of analytical sensitivity from detection of purified viral RNA from Sendai virus.

| | purified RNA from Sendai virus | |
|---|---|---|
| # of run | LOD, fM | LOD, RNA molecules/100 ul |
| 1 | 0.06 | 3600 |
| 2 | 0.06 | 3600 |
| 3 | 0.087 | 5220 |
| 4 | 0.098 | 5880 |
| 5 | 0.061 | 3660 |
| 6 | 0.059 | 3540 |
| 7 | 0.076 | 4560 |
| 8 | 0.01 | 600 |
| 9 | 0.008 | 480 |
| 10 | 0.004 | 240 |
| 11 | 0.022 | 1320 |
| 12 | 0.024 | 1440 |
| Average | 0.047 | 2845 |

Note:
LOD was calculated using 3 × SD above background signal.

Example 4

The following example describes an alternative denaturing process using pH instead of heat treatment, wherein, in some cases, better efficiency for genomic DNA detection was observed.

Figure 23:
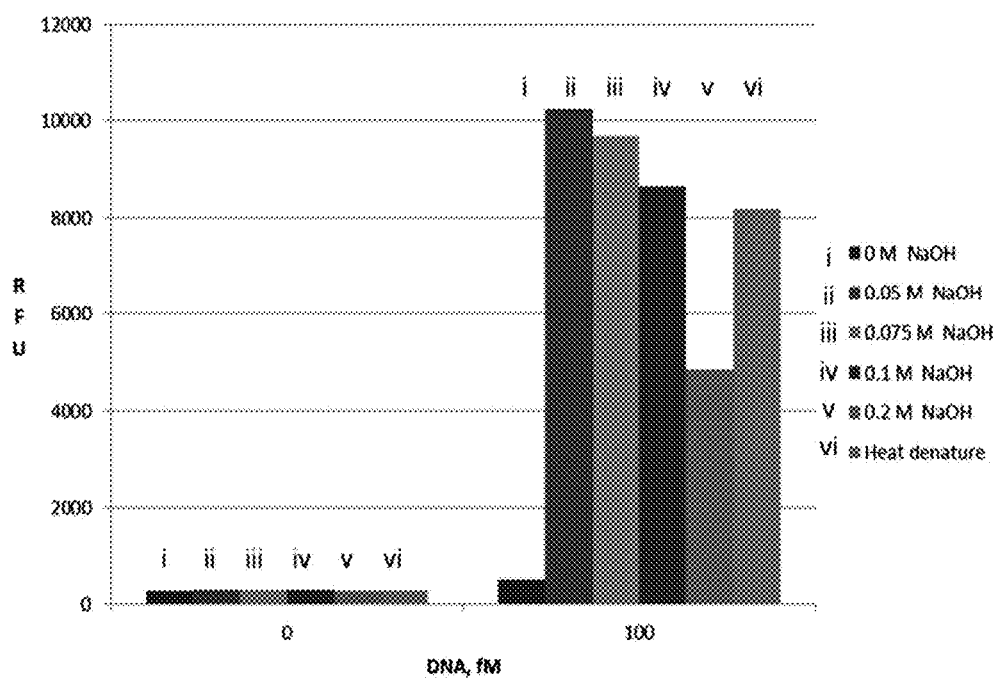
FIG. 23 shows results relating to the denaturing of DNA targets (E. coli) using NaOH at different concentrations (15 min incubation) followed by neutralization with HCl, compared to heat treating, according to some embodiments.

An approach based on incubation with a liquid rather than heat-treatment for denaturing DNA targets prior to hybridization was tested to make assay automation easier (e.g., when analyzing the sample using a SIMOA HD-1 analyzer, commercially available from Quanterix Corporation, Lexington, Mass.). This approach involved treating DNA samples at low pH by adding concentrated NaOH, followed by neutralizing the denatured samples with HCl. To examine denaturing efficiency, different concentrations of NaOH were first added to DNA samples for denaturing, and the denatured DNA samples were detected using a bead based assay. For comparison, comparable DNA samples were also denatured using heat treatment. FIG. 23 shows signal responses from all samples that were denatured under different conditions. For denaturing with low pH, DNA target treated with a final concentration of 0.05M NaOH gave the highest signals. The decreased signals from DNA targets treated with higher NaOH concentrations may be due to hydrolysis of the DNA targets under the conditions with extreme pH. At sufficiently low concentrations, treatment with NaOH gave better denaturing efficiency compared to heat treatment. Signals to background ratios were similar under all different conditions for denaturing. Next, different incubation times (e.g., 2, 10, and 15 minutes) for denaturing with NaOH were evaluated. Incubation of DNA targets with 0.05 M NaOH for 2 min was sufficient for denaturing as it gave similar signals to denaturing the DNA targets with longer incubation times. However, as will be understood by those of ordinary skill in the art, conditions when using low pH for DNA denaturing could be sample dependent. As a result, the concentration of NaOH used and the incubation time for other DNA or RNA molecules interest may be investigated to obtain the best denaturing efficiency, highest S/B, which can improve the assay sensitivity.

In FIG. 23: Denaturing of DNA targets (*E. coli*) using NaOH at different concentrations (15 min incubation) followed by neutralization with HCl, compared to heat treating the same sample at 96° C. for 5 min prior to DNA hybridization. All denatured DNA were detected using bulk response from the bead based assay (capture and detection probes for stx2 gene).

Example 5

The following example describes an assay which includes the step of target amplification (PCR).

In order to evaluate the sensitivity of a DNA assay when combined with PCR for target amplification prior to hybridization, purified genomic DNA from *S. aureus* was used as the target of interest for detection. Specific PCR primers were designed targeting to the nuc gene from *S. aureus* for amplification. Genomic DNA from *S. aureus* was first diluted to different concentrations (0, 10, 50, 100, 500, and 1000 copies per 100 µl), and amplified using PCR with 10 cycles for replication, followed by detection using the described single molecule array assay under the optimized conditions for the nuc gene. As a control for specificity, genomic DNA (1000 copies per 100 µl) from *E. coli* was also included for testing. As demonstrated in Table 9, 1000 copies per 100 µl of *S. aureus* DNA were readily detectable after 10 cycles of PCR, with a signal-to-background (S/B) of 26. At 10 fixed PCR cycles, PCR in combination with the described single molecule array assay had a limit of detection (LOD) of 10-50 copies of target genomic DNA per 100 µl. Genomic DNA from a non-target organism (*E. coli*) did not give any signals after PCR in combination with the described single molecule array assay. A study of signals as a function of number of PCR cycles indicated that >6 cycles were needed to detect 1000 copies per 100 µL (S/B=2.8) when using the described single molecule array assay coupled with PCR.

TABLE 9

Signals generated from detection of target genomic DNA from
*S. aureus* using the described single molecule array assay
after several cycles of PCR amplification.

| number of cycles | target concentration, copies/100 ul, from S. au | AEB | SD | CV | S/N |
| --- | --- | --- | --- | --- | --- |
| 10 | 0 | 0.0076 | 0.0001 | 2% | |
| 10 | 10 | 0.0099 | 0.0006 | 6% | 1.3 |
| 10 | 50 | 0.0181 | 0.0030 | 17% | 2.4 |
| 10 | 100 | 0.0340 | 0.0059 | 17% | 4.5 |
| 10 | 500 | 0.0876 | 0.0070 | 8% | 11.6 |
| 10 | 1000 | 0.1967 | 0.0363 | 18% | 26.0 |
| 10 | 1000 (from *E coli*) | 0.0077 | 0.0013 | 16% | 1.0 |

Example 6

The following example described an assay, wherein multiple DNA target analytes are analyzed.

Distinct fluorescent beads (e.g., capture objects) were prepared by coupling magnetic beads with different fluorescent dyes individually, each at various levels. Fluorescent dyes used for bead encoding produced fluorescent products at different emission wavelengths with no overlapping and did not interfere with the channel of resorufin, a product converted from the enzyme substrate, RGP, by SbG for signal generation. For each dye, various levels of dyes were conjugated onto magnetic beads, thus the fluorescence intensities generated from each level were different. As a result, encoded beads with different levels of the same fluorescent dye could also be distinguished from each other. For development of a 10-plex DNA assay, ten subpopulations of such fluorescent beads were first prepared using four different dyes (three levels for channel 647, three levels for channel 700, three levels for channel 750, and one level for channel 488), and tested on the SIMOA™ HD-1 analyzer (commercially available from Quanterix Corporation, Lexington, Mass.) for evaluation of fluorescence. Each subpopulation of these fluorescent beads was then used to prepare capture beads for each of ten target genes using the chosen probes from previous studies during the development of single-plex assays. These fluorescent capture beads were tested individually using the corresponding single-plex assay to demonstrate LODs comparable to those generated previously using capture beads with no fluorescent dyes.

Figure 24:
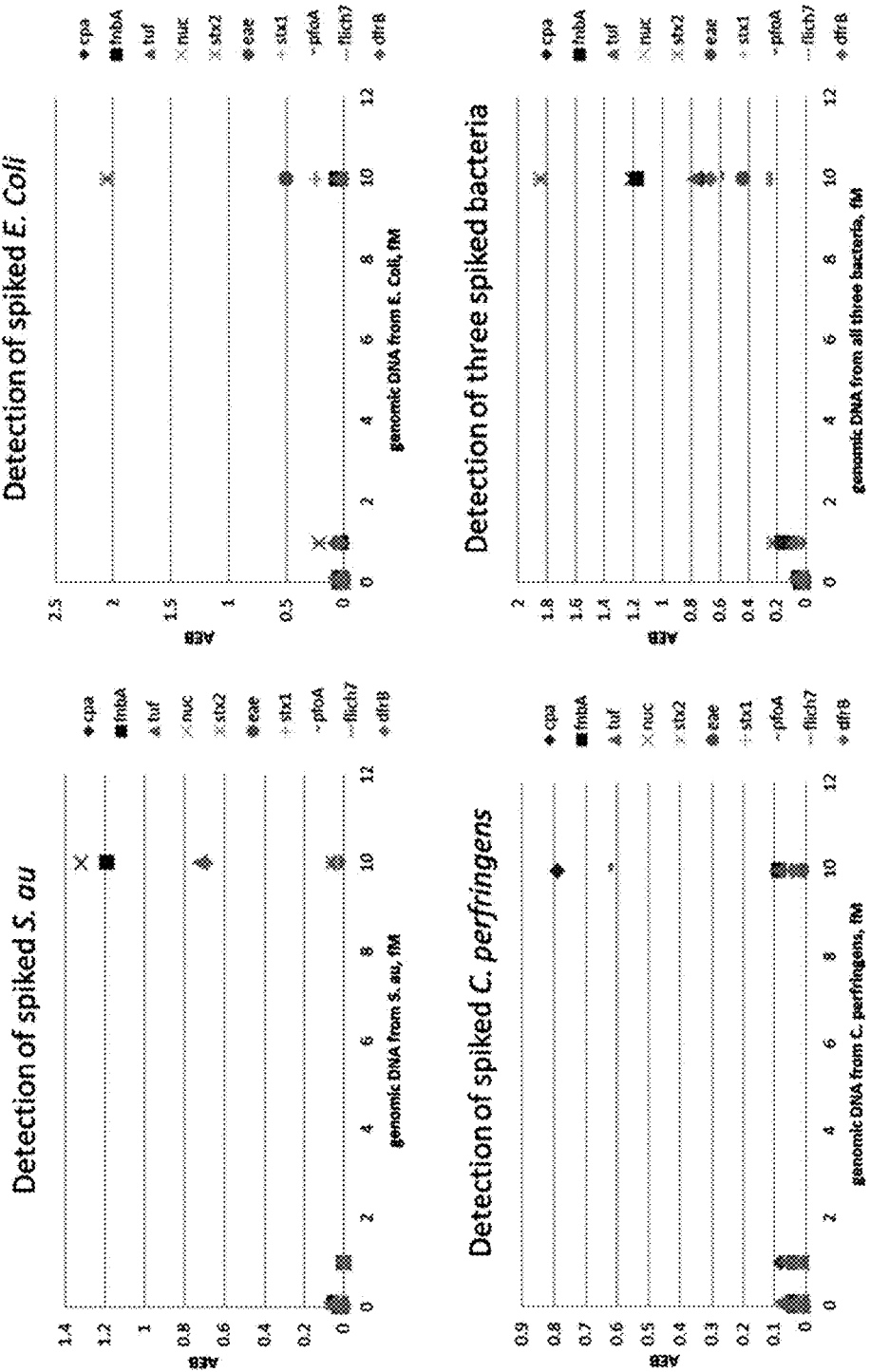
FIG. 24 shows results relating to the detection of spiked DNA from S. aureus, E. coli or C. perfringens individually and spiked DNA from all three bacteria using a 10-plex a single molecule assay DNA assay, according to some embodiments.

One challenge associated for developing a multiplex DNA assay is to avoid or minimize interactions from reagents, such as cross reactions between probes (e.g., capture probes and/or detection probes) from non-specific targets. For this purpose, capture bead comprising capture probes for each target gene were tested against non-specific detection probes from the rest of nine target genes in the absence of analytes for non-specific signals; probes that had cross reactions giving elevated background signals cannot be used together in the 10-plex DNA assay. For target genes with tested probes not compatible with the rest of genes, alternative probes from initial screening during the development of single-plex assay were screened again as described above for cross reactions. After screening, only the capture beads and detection probes giving no cross reactions with the probes from non-target genes were pooled and used for the multiplex DNA assay. FIG. 24 shows data for the 10-plex DNA assay generated on the SIMOA™ HD-1 Analzyer. In this assay, equal amounts of 10 fluorescent subpopulations of capture beads were mixed and selected detection probes for each target genes were pooled at optimized concentrations respectively. The target DNA from *S. aureus*, *E. coli*, or *C. perfringens* were individually spiked into buffers for detection, or all three were spiked together into buffers for detection using the 10-plex DNA assay. When individual target DNA was spiked into buffers, only the target genes from the corresponding bacterium gave dose responses with varying extent, while the non-target genes gave no signals. When all three targets DNA were spiked into buffers, every target gene included in the 10-plex assay gave dose-responses to the spiked targets. Most of the target genes demonstrated LODs close to or less than 0.1 fM in this initial run.

In FIG. 24: Detection of spiked DNA from *S. aureus*, *E. coli* or *C. perfringens* individually and spiked DNA from all three bacteria using a 10-plex single molecule array DNA assay as described.

Example 7

Figure 25:
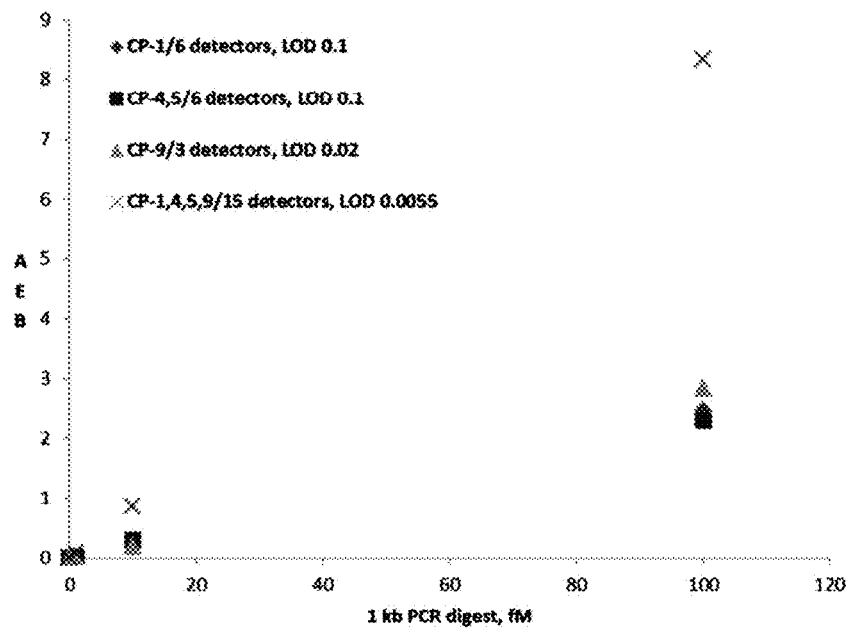
FIG. 25 shows a non-limiting result of a comparison an assay of using four capture probes (CP) compared to use of a single probe for detecting a PCR product from a gene, according to some embodiments.
Figure 26:
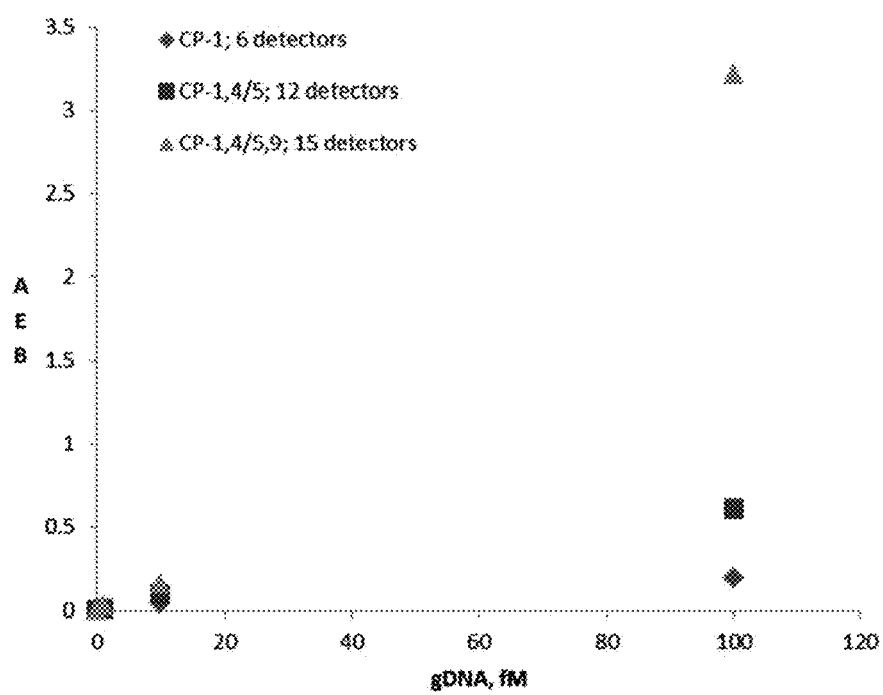
FIG. 26 shows a non-limiting comparison of as assay using one, two, and four capture probes (CP) compared to use a single probe for detecting genomic DNA from S. aureus, according to some embodiments.

FIG. 25 shows a non-limiting result of a comparison of using four capture probes (CP) compared to a single probe for detecting a PCR product from a gene. Note that CP 4 and 5 are closely aligned in the sequence. Similarly, FIG. 26 shows a non-limiting comparison of using one, two, and four capture probes (CP) compared to a single probe for detecting genomic DNA from S. aureus.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an", as used herein in the specification and in the claims, unless clearly indicated to the contrary, should be understood to mean "at least one".

In the claims, as well as in the specification above, all transitional phrases such as "comprising", "including", "carrying", "having", "containing", "involving", "holding", and the like are to be understood to be open-ended, i.e., to mean including but not limited to. Only the transitional phrases "consisting of" and "consisting essentially of" shall be closed or semi-closed transitional phrases, respectively.

The invention claimed is:

1. A method for determining a measure of the concentration of DNA or RNA molecules in a sample, comprising:
   fragmenting DNA or RNA from the sample to form fragmented DNA or RNA sequences;
   exposing the fragmented DNA or RNA sequences to at least a first type of binding ligand and a second type of binding ligand, wherein at least a portion of the fragmented DNA or RNA associates with at least one of the first type of binding ligand, at least a portion of the fragmented DNA or RNA associates with at least one of the second type of binding ligand, and at least a portion of the fragmented DNA or RNA associates with at least one of the first type of binding ligand and the second type of binding ligand, wherein the first type of binding ligand comprises a first nucleic acid sequence complimentary to a first portion of a sequence contained in the DNA or RNA and second type of binding ligand comprises a second nucleic acid sequence complimentary to a second portion of a sequence contained in the DNA or RNA, wherein the first nucleic acid sequence and the second nucleic acid sequence are different; and
   analyzing a portion of the sample from the exposing step to determine a total number of fragmented DNA or RNA sequences associated with (i) the first type of binding ligand, and (ii) the second type of binding ligand, and (iii) both the first type of binding ligand and the second type of binding ligand; wherein the first type of binding ligand and the second type of binding ligand produce substantially similar signals; and
   determining a measure of the concentration of the DNA or RNA molecules in the sample based on the total number of fragmented DNA or RNA sequences determined in the analyzing step.

2. The method of claim 1, wherein the first type of binding ligand and the second type of binding ligand produce signals comprising emission of electromagnetic energy differing in wavelength by not more than 50 nm.

3. The method of claim 1, wherein the first type of binding ligand and the second type of binding ligand produce indistinguishable signals.

4. The method of claim 1, wherein the exposing further comprises:
   spatially segregating at least a portion of the DNA or RNA fragments into a plurality of separate locations.

5. The method claim 4, wherein the number of fragmented DNA or RNA sequences is determined by determining the number of locations containing a DNA or RNA fragment.

6. The method of claim 4, wherein the plurality of locations comprises a plurality of reaction vessels.

7. The method of claim 6, wherein the average volume of the plurality of reaction vessels is between about 10 attoliters and about 100 picoliters.

8. The method of claim 6, wherein the average volume of the plurality of reaction vessels is between about 1 femtoliter and about 1 picoliter.

9. The method of claim 4, wherein following the spatially segregating step, the locations are exposed to precursor labeling agent.

10. The method of claim 9, wherein the precursor labeling agent is converted to a labeling agent upon exposure to a secondary binding ligand.

11. The method claim 10, wherein the number of locations comprising a fragmented DNA or RNA sequence is determined by determining the number of locations containing a secondary binding ligand.

12. The method of claim 10, wherein the number of locations comprising a fragmented DNA or RNA sequence is determined by determining the number of locations containing a labeling agent.

13. The method of claim 10, wherein the precursor labeling agent is a enzymatic substrate.

14. The method of claim 1, wherein each of the least one of the first type of binding ligand and each of the at least one second type of binding ligand comprise a moiety which is capable of binding a secondary binding ligand.

15. The method of claim 14, wherein the moiety comprises biotin.

16. The method of claim 1, wherein each of the least one first type of binding ligand and each of the at least one second type of binding ligand comprise a single moiety which is capable of binding a secondary binding ligand.

17. The method of claim 1, further comprising exposing the fragmented DNA or RNA sequences associated with at least one of the first type of binding ligand, at least one of the second type of binding ligand, or at least one of the first type of binding ligand and at least one of the second type of binding ligand to a plurality of secondary binding ligands, wherein a portion of each of the first type of binding ligands and the second type of binding ligands associated with the DNA or RNA sequences associates with a secondary binding ligand.

18. The method of claim 17, wherein the secondary binding ligand comprises an enzymatic component.

19. The method of claim 17, further comprising exposing the fragmented DNA or RNA sequences to a third type of binding ligand, wherein at least a portion of the fragmented DNA or RNA associates with one, two, or all three of the first type of binding ligand, the second type of binding ligand, or the third type of binding ligand, wherein the third type of binding ligand comprises a third nucleic acid sequence complimentary to a third portion of a sequence contained in the DNA or RNA, wherein the first, second, and third nucleic acid sequences are different.

20. The method of claim 1, wherein the first type of binding ligand and the second type of binding ligand each produce signals comprising emission of electromagnetic energy differing from each other in wavelength by not more than 10 nm.

21. The method of claim 1, wherein the method further comprises immobilizing the DNA or RNA fragments with respect to a plurality of capture objects such that at least some of the capture objects associate with at least one DNA or RNA fragment and a statistically significant fraction of the capture objects do not associate with any DNA or RNA fragments.

22. The method of claim 21, wherein the immobilizing is carried out prior to the exposing step.

23. The method of claim 21, wherein a portion of the capture objects subjected to the immobilizing step are spatially segregated into a plurality of separate locations.

24. The method of claim 21, wherein the plurality of capture objects comprises a plurality of beads.

25. The method of claim 21, wherein each capture object includes a binding surface having affinity of at least one DNA or RNA fragment.

* * * * *

SEQUENCE LISTING

```
<160> NUMBER OF SEQ ID NOS: 55

<210> SEQ ID NO 1
<211> LENGTH: 152
<212> TYPE: DNA
<213> ORGANISM: Staphylococcus aureus

<400> SEQUENCE: 1
tcagagaatt caactaaaaa gaaagaggtg ttagttatga cagaatactt attaagtgct      60
ggcatatgta tggcaattgt ttcaatatta cttataggga tggctatcag taatgtttcg     120
aaagggcaat acgcaaagag gggatccaat ca                                    152

<210> SEQ ID NO 2
<211> LENGTH: 966
<212> TYPE: DNA
<213> ORGANISM: Staphylococcus aureus

<400> SEQUENCE: 2
tgtctcgata tgatagtctg caacgattca tgttgtaggc tatttaattt tacaaataag      60
gctaaatata taagttctga cacctaaaat atagaaaata cataaaagta agtatagtta     120
ttttattata attattaaat ttttattaat taattgtaaa aatgtagaat tataattaat     180
taacgtttaa tattaaaatt aactaaaaag aaagaggtgt tagttatgac agaatactta     240
ttaagtgctg gcatatgtat ggcaattgtt tcaatattac ttatagggat ggctatcagt     300
aatgtttcga aagggcaata cgcaaagagg tttttctttt tcgctactag ttgcttagtg     360
ttaactttag ttgtagtttc aagtctaagt agctcagcaa atgcatcaca aacagataac     420
ggcgtaaata gaagtggttc tgaagatcca acagtatata gtgcaacttc aactaaaaaa     480
ttacataaag aacctgcgac tttaattaaa gcgattgatg gtgatacggt taaattaatg     540
tacaaaggtc aaccaatgac attcagacta ttattggttg atacacctga aacaaagcat     600
cctaaaaaag gtgtagagaa atatggtcct gaagcaagtg catttacgaa aaaaatggta     660
gaaaatgcaa agaaaattga agtcgagttt gacaaaggtc aaagaactga taaatatgga     720
cgtggcttag cgtatattta tgctgatgga aaaatggtaa acgaagcttt agttcgtcaa     780
ggcttggcta aagttgctta tgtttacaaa cctaacaata cacatgaaca acatttaaga     840
```

```
aaaagtgaag cacaagcgaa aaaagagaaa ttaaatattt ggagcgaaga caacgctgat    900
tcaggtcaat aatgctcatt gtaaaagtgt cactgctgct agtggcactt ttataatttt    960
tagatc                                                                966
```

<210> SEQ ID NO 3
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 3

```
gaagggcaa tacgcaaaga gg                                                22
```

<210> SEQ ID NO 4
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 4

```
aaagaaagag gtgttagtta tgac                                             24
```

<210> SEQ ID NO 5
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 5

```
taagtgctgg catatgtatg gc                                               22
```

<210> SEQ ID NO 6
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 6

```
agggatggct atcagtaatg tt                                               22
```

<210> SEQ ID NO 7
<211> LENGTH: 24
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (13)..(13)
<223> OTHER INFORMATION: biotinylation
<220> FEATURE:
<221> NAME/KEY: misc_feature
<222> LOCATION: (16)..(16)
<223> OTHER INFORMATION: biotinylation
<220> FEATURE:
<221> NAME/KEY: misc_feature
<222> LOCATION: (22)..(22)
<223> OTHER INFORMATION: biotinylation

<400> SEQUENCE: 7

```
aaagaaagag gtgttagtta tgac                                             24
```

<210> SEQ ID NO 8
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 8
tgtctcgata tgatagtctg caacgattc                              29

<210> SEQ ID NO 9
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 9
ctcagcaaat gcatcacaaa cagataa                                27

<210> SEQ ID NO 10
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 10
aacagataac ggcgtaaata gaagtggt                               28

<210> SEQ ID NO 11
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 11
aaggcttggc taaagttgct tatgttt                                27

<210> SEQ ID NO 12
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 12
ttacaaataa ggctaaatat ataagttctg acacc                       35

<210> SEQ ID NO 13
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 13
agaaaataca taaagtaag tatagttatt ttattataat tattaaattt        50

<210> SEQ ID NO 14
<211> LENGTH: 27
<212> TYPE: DNA
<213> ORGANISM: Artificial Sequence
<220> FEATURE:
<223> OTHER INFORMATION: Synthetic Polynucleotide

```
<400> SEQUENCE: 14
ctggcatatg tatggcaatt gtttcaa                                          27

<210> SEQ ID NO 15
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 15
acttataggg atggctatca gtaatgtttc g                                     31

<210> SEQ ID NO 16
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 16
agggcaatac gcaaagaggt tt                                               22

<210> SEQ ID NO 17
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 17
ttcgctacta gttgcttagt gttaactt                                         28

<210> SEQ ID NO 18
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 18
agatccaaca gtatatagtg caacttcaac t                                     31

<210> SEQ ID NO 19
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 19
aaagcgattg atggtgatac ggttaaatta a                                     31

<210> SEQ ID NO 20
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 20
gttgatacac ctgaaacaaa gcatcctaaa                                       30

<210> SEQ ID NO 21
```

```
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 21
ggtgtagaga aatatggtcc tgaagcaa                                          28

<210> SEQ ID NO 22
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 22
aatggtagaa aatgcaaaga aaattgaagt cg                                     32

<210> SEQ ID NO 23
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 23
acaaaggtca agaactgat aaatatggac g                                       31

<210> SEQ ID NO 24
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 24
aaacctaaca atacacatga acaacattta agaaa                                  35

<210> SEQ ID NO 25
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 25
acgctgattc aggtcaataa tgctca                                            26

<210> SEQ ID NO 26
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 26
gtgtcactgc tgctagtggc ac                                                22

<210> SEQ ID NO 27
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 27
```

```
gatacacctg aaacaaagca tcc                                              23
```

<210> SEQ ID NO 28
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 28

```
gccacgtcca tatttatcag ttc                                              23
```

<210> SEQ ID NO 29
<211> LENGTH: 26
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Attached to FAM
<220> FEATURE:
<221> NAME/KEY: misc_feature
<222> LOCATION: (29)..(29)
<223> OTHER INFORMATION: Attached to TAMRA

<400> SEQUENCE: 29

```
tggtcctgaa gcaagtgcat ttacga                                           26
```

<210> SEQ ID NO 30
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 30

```
ggcgtggagg atgtcaagaa tatagttat                                        29
```

<210> SEQ ID NO 31
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 31

```
tggtgctcaa ggagtattgt gtaatatgaa                                       30
```

<210> SEQ ID NO 32
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 32

```
tcagttaatg tggtggcgaa ggaatt                                           26
```

<210> SEQ ID NO 33
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 33
tgcaaagacg tatgtagatt cgctga                                          26

<210> SEQ ID NO 34
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 34
aggtactcca ttacagacta tttcatcagg                                      30

<210> SEQ ID NO 35
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 35
tccaggtaca acagcggtta cattg                                           25

<210> SEQ ID NO 36
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 36
cgtgttgcag ggatcagtcg tac                                             23

<210> SEQ ID NO 37
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 37
aatcgccatt cgttgactac ttcttatct                                       29

<210> SEQ ID NO 38
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 38
ttaatgtcgc atagtggaac ctcac                                           25

<210> SEQ ID NO 39
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 39
gcagtctgtg gcaagagcga tg                                              22

<210> SEQ ID NO 40
<211> LENGTH: 27

```
<212> TYPE: DNA
<213> ORGANISM: Artificial Sequence
<220> FEATURE:
<223> OTHER INFORMATION: Synthetic Polynucleotide

<400> SEQUENCE: 40
ggcgttctta tgtaatgact gctgaag                                          27

<210> SEQ ID NO 41
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 41
ggttgagtag cgtcctgcct ga                                               22

<210> SEQ ID NO 42
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 42
gacaagactc tgttcgtgta ggaagaat                                         28

<210> SEQ ID NO 43
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 43
ggaagcgtgg cattaatact gaattgtc                                         28

<210> SEQ ID NO 44
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 44
atctgatgag tttccttcta tgtgtccg                                         28

<210> SEQ ID NO 45
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 45
aatcttcagt ctcttcttct cagtgcg                                          27

<210> SEQ ID NO 46
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 46
```

```
gtgggtgata aagaattatt taccaacaga                                        30

<210> SEQ ID NO 47
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 47
ttcgttgact cagaatagct cagt                                              24

<210> SEQ ID NO 48
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 48
aaatagcagg cggagattca taaatgttaa                                        30

<210> SEQ ID NO 49
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 49
catctcaatt cagtcagttg ttgccg                                            26

<210> SEQ ID NO 50
<211> LENGTH: 966
<212> TYPE: DNA
<213> ORGANISM: Staphylococcus aureus

<400> SEQUENCE: 50
tgtctcgata tgatagtctg caacgattca tgttgtaggc tatttaattt tacaaataag       60
gctaaatata taagttctga caccctaaaat atagaaaata cataaaagta agtatagtta     120
ttttattata attattaaat ttttattaat taattgtaaa aatgtagaat tataattaat      180
taacgtttaa tattaaaatt aactaaaaag aaagaggtgt tagttatgac agaatactta      240
ttaagtgctg gcatatgtat ggcaattgtt tcaatattac ttatagggat ggctatcagt      300
aatgtttcga aagggcaata cgcaaagagg ttttttcttt tcgctactag ttgcttagtg      360
ttaactttag ttgtagtttc aagtctaagt agctcagcaa atgcatcaca aacagataac      420
ggcgtaaata gaagtggttc tgaagatcca acagtatata gtgcaacttc aactaaaaaa      480
ttacataaag aacctgcgac tttaattaaa gcgattgatg gtgatacggt taaattaatg      540
tacaaaggtc aaccaatgac attcagacta ttattggttg atacacctga acaaagcat       600
cctaaaaaag gtgtagagaa atatggtcct gaagcaagtg catttacgaa aaaaatggta      660
gaaaatgcaa agaaaattga agtcgagttt gacaaaggtc aaagaactga taaatatgga      720
cgtggcttag cgtatattta tgctgatgga aaaatggtaa acgaagcttt agttcgtcaa      780
ggcttggcta agttgctta tgtttacaaa cctaacaata cacatgaaca acatttaaga      840
aaaagtgaag cacaagcgaa aaaagagaaa ttaaatattt ggagcgaaga caacgctgat      900
tcaggtcaat aatgctcatt gtaaaagtgt cactgctgct agtggcactt ttataatttt      960
tagatc                                                                966
```

<210> SEQ ID NO 51
<211> LENGTH: 24
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: biotinylation

<400> SEQUENCE: 51
aaagaaagag gtgttagtta tgac                                    24

<210> SEQ ID NO 52
<211> LENGTH: 22
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: biotinylation

<400> SEQUENCE: 52
taagtgctgg catatgtatg gc                                      22

<210> SEQ ID NO 53
<211> LENGTH: 22
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: biotinylation

<400> SEQUENCE: 53
agggatggct atcagtaatg tt                                      22

<210> SEQ ID NO 54
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 54
gaaagggcaa tacgcaaaga gg                                      22

<210> SEQ ID NO 55
<211> LENGTH: 152
<212> TYPE: DNA
<213> ORGANISM: Artificial Sequence
<220> FEATURE:
<223> OTHER INFORMATION: Synthetic Polynucleotide

<400> SEQUENCE: 55
tgattggatc ccctctttgc gtattgccct ttcgaaacat tactgatagc catccctata    60
agtaatattg aaacaattgc catacatatg ccagcactta ataagtattc tgtcataacg   120
aacacctctt tctttttagt tgaattctct ga                                 152